US012592298B2

(12) United States Patent
Parnaby et al.

(10) Patent No.: US 12,592,298 B2
(45) Date of Patent: Mar. 31, 2026

(54) HARDWARE EXECUTION AND ACCELERATION OF ARTIFICIAL INTELLIGENCE-BASED BASE CALLER

(71) Applicant: Illumina, Inc., San Diego, CA (US)

(72) Inventors: Gavin Derek Parnaby, Laguna Niguel, CA (US); Mark David Hahm, Hartland, WI (US); Andrew Christopher Du Preez, Poway, CA (US); Jason Edward Cosky, San Diego, CA (US); John S. Vieceli, Encinitas, CA (US); Andrew Dodge Heiberg, San Diego, CA (US); Gery Vessere, Oakland, CA (US)

(73) Assignee: Illumina, Inc., San Diego, CA (US)

( * ) Notice: Subject to any disclaimer, the term of this patent is extended or adjusted under 35 U.S.C. 154(b) by 1336 days.

(21) Appl. No.: 17/176,147

(22) Filed: Feb. 15, 2021

(65) Prior Publication Data

US 2021/0265015 A1     Aug. 26, 2021

Related U.S. Application Data

(60) Provisional application No. 63/072,032, filed on Aug. 28, 2020, provisional application No. 62/979,411, filed on Feb. 20, 2020, provisional application No. 62/979,412, filed on Feb. 20, 2020, provisional application No. 62/979,399, filed on Feb. 20, 2020, provisional application No. 62/979,385, filed on Feb. 20, 2020.

(51) Int. Cl.
| | |
|---|---|
| *G16B 30/20* | (2019.01) |
| *C12Q 1/6869* | (2018.01) |
| *G06N 3/04* | (2023.01) |
| *G06N 3/08* | (2023.01) |
| *G16B 40/10* | (2019.01) |

(52) U.S. Cl.
CPC .............. *G16B 30/20* (2019.02); *G06N 3/04* (2013.01); *G06N 3/08* (2013.01); *G16B 40/10* (2019.02); *C12Q 1/6869* (2013.01)

(58) Field of Classification Search
CPC .......... G16B 30/20; G16B 40/10; G06N 3/04; G06N 3/08; C12Q 1/6869
See application file for complete search history.

(56) References Cited

U.S. PATENT DOCUMENTS

| | | | |
|---|---|---|---|
| 5,641,658 A | 6/1997 | Adams et al. | |
| 6,090,592 A | 7/2000 | Adams et al. | |
| 7,057,026 B2 | 6/2006 | Barnes et al. | |
| 7,115,400 B1 * | 10/2006 | Adessi ................. | C12Q 1/6874 435/6.12 |
| 7,211,414 B2 | 5/2007 | Hardin et al. | |
| 7,315,019 B2 | 1/2008 | Turner et al. | |

| | | | |
|---|---|---|---|
| 7,329,492 B2 | 2/2008 | Hardin et al. | |
| 7,405,281 B2 | 7/2008 | Xu et al. | |
| 7,427,673 B2 | 9/2008 | Balasubramanian et al. | |
| 7,541,444 B2 | 6/2009 | Milton et al. | |
| 7,566,537 B2 | 7/2009 | Balasubramanian et al. | |
| 7,592,435 B2 | 9/2009 | Milton et al. | |
| 8,182,993 B2 | 5/2012 | Tomaney et al. | |
| 8,241,573 B2 | 8/2012 | Banerjee et al. | |
| 8,392,126 B2 | 3/2013 | Mann | |
| 8,401,258 B2 | 3/2013 | Hargrove et al. | |
| 8,407,012 B2 | 3/2013 | Erlich et al. | |
| 8,594,439 B2 | 11/2013 | Staelin et al. | |
| 8,725,425 B2 | 5/2014 | Heiner et al. | |
| 8,795,971 B2 | 8/2014 | Kersey et al. | |
| 8,965,076 B2 | 2/2015 | Garcia et al. | |
| 9,279,154 B2 | 3/2016 | Previte et al. | |
| 9,453,258 B2 | 9/2016 | Kain et al. | |
| 9,708,656 B2 | 7/2017 | Turner et al. | |

(Continued)

FOREIGN PATENT DOCUMENTS

| | | |
|---|---|---|
| CA | 2894317 A1 | 12/2016 |
| CA | 3104851 A1 | 11/2020 |

(Continued)

OTHER PUBLICATIONS

Chakradhar, Srimat T. et al. A dynamically configurable coprocessor for convolutional neural networks. Proceedings of the 37th annual international symposium on Computer architecture (2010): 247-257 (Year: 2010).*

Boza V, Brejov B, Vina T (2017) DeepNano: Deep recurrent neural networks for base calling in MinION nanopore reads. PLOS ONE 12(6): e0178751. (Year: 2017).*

Huang, Neng et al. An attention-based neural network basecaller for Oxford Nanopore sequencing data. 2019 IEEE International Conference on Bioinformatics and Biomedicine (BIBM) (2019): 390-394. (Year: 2019).*

Kircher, Martin et al. Improved base calling for the Illumina Genome Analyzer using machine learning strategies. Genome biology vol. 10,8 (2009): R83. (Year: 2009).*

(Continued)

*Primary Examiner* — Olivia M. Wise
*Assistant Examiner* — Keenan Neil Anderson-Fears
(74) *Attorney, Agent, or Firm* — Keller Preece PLLC

(57) ABSTRACT

A system for analysis of base call sensor output has memory accessible by the runtime program storing tile data including sensor data for a tile from sensing cycles of a base calling operation. A neural network processor having access to the memory is configured to execute runs of a neural network using trained parameters to produce classification data for sensing cycles. A run of the neural network operates on a sequence of N arrays of tile data from respective sensing cycles of N sensing cycles, including a subject cycle, to produce the classification data for the subject cycle. Data flow logic moves tile data and the trained parameters from the memory to the neural network processor for runs of the neural network using input units including data for spatially aligned patches of the N arrays from respective sensing cycles of N sensing cycles.

20 Claims, 22 Drawing Sheets
(4 of 22 Drawing Sheet(s) Filed in Color)

(56)                 References Cited

U.S. PATENT DOCUMENTS

| | | |
|---|---|---|
| 10,023,911 B2 | 7/2018 | Tomaney et al. |
| 10,068,054 B2 | 9/2018 | Van Rooyen et al. |
| 10,152,776 B2 | 12/2018 | Langlois et al. |
| 10,168,438 B2 | 1/2019 | Dennis et al. |
| 10,241,075 B2 | 3/2019 | Davey et al. |
| 10,354,747 B1 | 7/2019 | DePristo et al. |
| 10,423,861 B2 | 9/2019 | Gao et al. |
| 10,491,239 B1 | 11/2019 | Hubara |
| 10,527,549 B2 | 1/2020 | Rebetez et al. |
| 10,540,591 B2 | 1/2020 | Gao et al. |
| 10,619,195 B2 | 4/2020 | Lamb et al. |
| 10,648,027 B2 | 5/2020 | Mannion et al. |
| 10,711,299 B2 | 7/2020 | Rothberg et al. |
| 10,713,794 B1 | 7/2020 | He et al. |
| 10,740,880 B2 | 8/2020 | Paik et al. |
| 10,740,883 B2 | 8/2020 | Zerfass et al. |
| 10,755,810 B2 | 8/2020 | Buckler et al. |
| 10,963,673 B2 | 3/2021 | Schaumberg et al. |
| 11,138,496 B2 | 10/2021 | Seth |
| 2002/0055100 A1 | 5/2002 | Kawashima et al. |
| 2003/0062485 A1 | 4/2003 | Fernandez et al. |
| 2004/0002090 A1 | 1/2004 | Mayer et al. |
| 2004/0096853 A1 | 5/2004 | Mayer |
| 2006/0014151 A1 | 1/2006 | Ogura et al. |
| 2006/0040297 A1 | 2/2006 | Leamon et al. |
| 2006/0064248 A1 | 3/2006 | Saidi et al. |
| 2006/0188901 A1 | 8/2006 | Barnes et al. |
| 2006/0240439 A1 | 10/2006 | Smith et al. |
| 2006/0269130 A1 | 11/2006 | Maroy et al. |
| 2007/0128624 A1 | 6/2007 | Gormley et al. |
| 2007/0166705 A1 | 7/2007 | Milton et al. |
| 2008/0009420 A1 | 1/2008 | Schroth et al. |
| 2008/0234136 A1 | 9/2008 | Drmanac et al. |
| 2008/0242560 A1 | 10/2008 | Gunderson et al. |
| 2009/0081775 A1 | 3/2009 | Hodneland et al. |
| 2010/0046830 A1 | 2/2010 | Wang et al. |
| 2010/0111370 A1 | 5/2010 | Black et al. |
| 2010/0157086 A1 | 6/2010 | Segale et al. |
| 2011/0059865 A1 | 3/2011 | Smith et al. |
| 2011/0065607 A1 | 3/2011 | Kersey et al. |
| 2011/0281736 A1 | 11/2011 | Drmanac et al. |
| 2011/0286628 A1 | 11/2011 | Goncalves et al. |
| 2011/0295902 A1 | 12/2011 | Mande et al. |
| 2012/0015825 A1 | 1/2012 | Zhong et al. |
| 2012/0020537 A1 | 1/2012 | Garcia et al. |
| 2013/0059740 A1 | 3/2013 | Drmanac et al. |
| 2013/0079232 A1 | 3/2013 | Kain et al. |
| 2013/0124100 A1 | 5/2013 | Drmanac et al. |
| 2013/0188866 A1 | 7/2013 | Obrador et al. |
| 2013/0250407 A1 | 9/2013 | Schaffer et al. |
| 2014/0051588 A9 | 2/2014 | Drmanac et al. |
| 2014/0152801 A1 | 6/2014 | Fine et al. |
| 2015/0079596 A1 | 3/2015 | Eltoukhy et al. |
| 2015/0117784 A1 | 4/2015 | Lin et al. |
| 2015/0169824 A1 | 6/2015 | Kermani et al. |
| 2016/0042511 A1 | 2/2016 | Chukka et al. |
| 2016/0078272 A1 | 3/2016 | Hammoud |
| 2016/0110498 A1 | 4/2016 | Bruand et al. |
| 2016/0196479 A1 | 7/2016 | Chertok et al. |
| 2016/0350914 A1 | 12/2016 | Champlin et al. |
| 2016/0356715 A1 | 12/2016 | Zhong et al. |
| 2016/0357903 A1 | 12/2016 | Shendure et al. |
| 2016/0371431 A1 | 12/2016 | Haque et al. |
| 2017/0044601 A1 | 2/2017 | Crnogorac et al. |
| 2017/0098032 A1 | 4/2017 | Desai et al. |
| 2017/0116520 A1 | 4/2017 | Min et al. |
| 2017/0161545 A1 | 6/2017 | Champlin et al. |
| 2017/0169313 A1 | 6/2017 | Choi et al. |
| 2017/0249421 A1 | 8/2017 | Eberle et al. |
| 2017/0249744 A1 | 8/2017 | Wang et al. |
| 2017/0362634 A1 | 12/2017 | Ota et al. |
| 2018/0075279 A1 | 3/2018 | Gertych et al. |
| 2018/0107927 A1 | 4/2018 | Frey |
| 2018/0114337 A1 | 4/2018 | Li et al. |
| 2018/0189613 A1 | 7/2018 | Wolf et al. |
| 2018/0195953 A1 | 7/2018 | Langlois et al. |
| 2018/0201992 A1 | 7/2018 | Wu et al. |
| 2018/0211001 A1 | 7/2018 | Gopalan et al. |
| 2018/0274023 A1 | 9/2018 | Belitz et al. |
| 2018/0305751 A1 | 10/2018 | Vermaas et al. |
| 2018/0322327 A1 | 11/2018 | Smith et al. |
| 2018/0330824 A1 | 11/2018 | Athey |
| 2018/0334711 A1 | 11/2018 | Kelley et al. |
| 2018/0334712 A1 | 11/2018 | Singer et al. |
| 2018/0340234 A1 | 11/2018 | Scafe et al. |
| 2019/0034586 A1 | 1/2019 | Pirrotte et al. |
| 2019/0080450 A1 | 3/2019 | Arar et al. |
| 2019/0107642 A1 | 4/2019 | Farhadi Nia et al. |
| 2019/0114511 A1 | 4/2019 | Gao et al. |
| 2019/0114544 A1 | 4/2019 | Sundaram et al. |
| 2019/0156915 A1 | 5/2019 | Zhang et al. |
| 2019/0164010 A1 | 5/2019 | Ma et al. |
| 2019/0170680 A1 | 6/2019 | Sikora et al. |
| 2019/0180153 A1 | 6/2019 | Buckler et al. |
| 2019/0213473 A1 | 7/2019 | Dutta et al. |
| 2019/0237160 A1 | 8/2019 | Rothberg et al. |
| 2019/0237163 A1 | 8/2019 | Wang et al. |
| 2019/0244348 A1 | 8/2019 | Buckler et al. |
| 2019/0266491 A1 | 8/2019 | Gao et al. |
| 2019/0272638 A1 | 9/2019 | Mouton et al. |
| 2019/0318806 A1 | 10/2019 | Wise et al. |
| 2019/0332118 A1 | 10/2019 | Wang et al. |
| 2019/0392578 A1 | 12/2019 | Chukka et al. |
| 2020/0027002 A1 | 1/2020 | Hickson et al. |
| 2020/0054306 A1 | 2/2020 | Mehanian et al. |
| 2020/0057838 A1 | 2/2020 | Yekhanin et al. |
| 2020/0065675 A1 | 2/2020 | Sundaram et al. |
| 2020/0125947 A1 | 4/2020 | Park et al. |
| 2020/0176082 A1 | 6/2020 | Massingham |
| 2020/0193597 A1 | 6/2020 | Fan et al. |
| 2020/0226368 A1 | 7/2020 | Bakalo et al. |
| 2020/0256856 A1 | 8/2020 | Chou et al. |
| 2020/0302223 A1 | 9/2020 | Dutta et al. |
| 2020/0302224 A1 | 9/2020 | Jaganathan et al. |
| 2020/0302297 A1 | 9/2020 | Jaganathan et al. |
| 2020/0302603 A1 | 9/2020 | Barnes et al. |
| 2020/0303039 A1 | 9/2020 | Pratt et al. |
| 2020/0320294 A1 | 10/2020 | Mangal et al. |
| 2020/0342955 A1 | 10/2020 | Guo et al. |
| 2020/0364565 A1 | 11/2020 | Kostem |
| 2020/0388029 A1 | 12/2020 | Saltz et al. |
| 2021/0027462 A1 | 1/2021 | Bredno et al. |
| 2021/0056287 A1 | 2/2021 | Schaumburg et al. |
| 2021/0072391 A1 | 3/2021 | Li et al. |
| 2021/0089827 A1 | 3/2021 | Kumagai et al. |
| 2021/0115490 A1 | 4/2021 | Embree et al. |
| 2021/0390278 A1 | 12/2021 | Van Leeuwen et al. |

FOREIGN PATENT DOCUMENTS

| | | |
|---|---|---|
| CN | 110223281 A | 9/2019 |
| CN | 110245685 A | 9/2019 |
| EP | 3130681 A1 | 2/2017 |
| EP | 3373238 A1 | 9/2018 |
| JP | 2007199397 A | 8/2007 |
| NL | 2023310 B1 | 9/2020 |
| NL | 2023311 B1 | 9/2020 |
| NL | 2023312 B1 | 9/2020 |
| NL | 2023314 B1 | 9/2020 |
| NL | 2023316 B1 | 9/2020 |
| RU | 2706960 C1 | 11/2019 |
| WO | 9106678 A1 | 5/1991 |
| WO | 2004018497 A2 | 3/2004 |
| WO | 2005065814 A1 | 7/2005 |
| WO | 2006064199 A1 | 6/2006 |
| WO | 2007010251 A2 | 1/2007 |
| WO | 2007123744 A2 | 11/2007 |
| WO | 2008154317 A1 | 12/2008 |
| WO | 2012058096 A1 | 5/2012 |
| WO | 2014142921 A1 | 9/2014 |
| WO | 2015084985 A2 | 6/2015 |
| WO | 2016145516 A1 | 9/2016 |
| WO | 2016201564 A1 | 12/2016 |
| WO | 2017184997 A1 | 10/2017 |

(56) References Cited

FOREIGN PATENT DOCUMENTS

| WO | 2018129314 A1 | 7/2018 |
| WO | 2018165099 A1 | 9/2018 |
| WO | 2018203084 A1 | 11/2018 |
| WO | 2019027767 A1 | 2/2019 |
| WO | 2019028047 A1 | 2/2019 |
| WO | 2019055856 A1 | 3/2019 |
| WO | 2019079166 A1 | 4/2019 |
| WO | 2019079182 A1 | 4/2019 |
| WO | 2019079202 A1 | 4/2019 |
| WO | 2019090251 A2 | 5/2019 |
| WO | 2019136284 A1 | 7/2019 |
| WO | 2019136388 A1 | 7/2019 |
| WO | 2019140402 A1 | 7/2019 |
| WO | 2019147904 A1 | 8/2019 |
| WO | 2020014280 A1 | 1/2020 |
| WO | 2020123552 A1 | 6/2020 |

OTHER PUBLICATIONS

Chandel, Ruchika, and Gaurav Gupta. "Image filtering algorithms and techniques: A review." International Journal of Advanced Research in Computer Science and Software Engineering 3.10 (2013) (Year: 2013).*

Min, et. al., "Deep Learning in Bioinformatics", Jun. 19, 2016, 46pgs.

Jiminez et. al., DeepSite—protein binding site predictor using 3D CNNs, dated Oct. 1, 2017, 7 pages.

Pu et. al., "DeepDrug3D: Classification of ligand-binding pockets in proteins with a convolutional neural network", dated Feb. 4, 2019, 23 pages.

Adam, "Deep learning, 3D technology to improve structure modeling for protein interactions, create better drugs", dated Jan. 9, 2020, 4 pages.

Varela, "Ligvoxel: A Deep Learning Pharmacore-Field Predictor", dated Mar. 19, 2019, 5 pages.

Li et. al., "Predicting changes in protein thermostability upon mutation with deep 3D convolutional neural networks", dated Feb. 28, 2020, 21 pages.

Raschka et. al., "Machine Learning and AI-based approaches for bioactive ligand discovery and GPCR-ligand recognition", dated Jun. 6, 2020, 33 pages.

Morrone et. al., "Combining docking pose rank and structure with deep learning improves protein-ligand binding mode prediction", dated Oct. 7, 2019, 13 pages.

Li, "Machine Learning Methods for Medical and Biological Image Computing", dated Summer 2016, 113 pages.

Rivera et. al., "A Deep Learning Approach to Protein Structure Prediction", dated Apr. 24, 2019, 22 pages.

Aritake et. al., "Single-molecule localization by voxel-wise regression using convolutional neural network", dated Nov. 3, 2020, 11 pages.

Townshend et. al., "End-to-End Learning on 3D Protein Structure for Interface Prediction", dated 2019, 10 pages.

Amidi et. al., "EnzyNet: enzyme classification using 3D convolutional neural networks on spatial representation", dated Jul. 25, 2017, 18 pages.

Luna, "Machine Learning in structural biology and chemoinformatics", dated 2019, 106 pages.

Anonymous, "Transferrable end-to-end learning for protein interface prediction", dated 2019, 12 pages.

Dias et. al., "Artificial intelligence in clinical and genomic diagnostics", dated 2019, 12 pages.

Luna et. al., "A Deep-Learning Approach toward Rational Molecular Docking Protocol Selection", dated May 27, 2020, 12 pages.

Li et. al., "DeepAtom: A Framework for Protein-Ligand Binding Affinity Prediction", dated 2019, 8 pages.

Zhang et. al., "Template-based prediction of protein structure with deep learning", dated Jun. 2, 2020, 16 pages.

Wallach et. al., AtomNet: A Deep Convolutional Neural Network for Bioactivity Prediction in Structure-based Drug Discovery, dated Oct. 10, 2015, 11 pages.

Illumina, Two-Channel SBS Sequencing Technology, 2016, 2 pages.

Illumina, Low-diversity sequencing on the Illumina HiSeq Platform, 2014, 2 pages.

Hedegaard, An introduction to "Next Generation" DNA Sequencing, dated Nov. 26, 2017, 63 pages.

Jordan , An overview of semantic image segmentation, dated May 21, 2018, 28 pages retrieved on Jul. 21, 2021. Retrieved from the internet [URL: https://www.jeremyjordan.me/semantic-segmentation/ ].

Lanchantin, Deep Motif Dashboard: Visualizing and Understanding Genomic Sequences Using Deep Neural Networks, Oct. 18, 2016, 11 pages.

Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/].

James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].

Townley, Illumina Primary and Secondary Analysis, Illumina UK, 2010, 33 pages.

Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa ].

Bowen, Nanotechnology for a Genomic Revolution, Illumina, dated Dec. 14, 2016, 40 pages.

Han, Deconvolutions in Convolutional Neural Networks, Postech Computer Vision Lab, 2015, 20 pages.

Illumina, Illumina's Genotyping Data Normalization Methods, 2006, 6 pages.

Illumina, Quality Scores for Next-Generation Sequencing—Assessing sequencing accuracy using Phred quality scoring, 2011, 2 pages.

Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].

Illumina, An Introduction to Next-Generation Sequencing Technology, 2017, 16 pages.

Belanovic, Library of Parameterized Hardware Modules for Floating-Point Arithmetic with an Example Application, Northeastern University, Boston, MA, May 2002, 83 pages.

Massingham, Base Calling: methods, problems and alternatives, EMBL Advanced Course in Analysis of Short Read Sequencing Data, Jun. 8, 2009-Jun. 10, 2009, 84 pages.

Thoma, A Survey of Semantic Segmentation, dated May 11, 2016, 16 pages.

Rodriguez-Ezpeleta, Bioinformatics for High Throughput Sequencing, Springer, 2012, 266 pages.

Illumina, Optimizing Cluster Density on Illumina Sequencing Systems, 2016, 12 pages.

Boza et. al., DeepNano: Deep recurrent neural networks for base calling in MinION nanopore reads, PLOS ONE, dated Jun. 5, 2017, 13 pages.

Kircher, Understanding and Improving high-throughput sequencing data production and analysis, Leipzig University, 2011, 216 pages.

Lutteropp, Error-Profile-Aware Correction of Next Generation Sequencing Reads, Karlsruhe Institute of Technology, dated Mar. 31, 2017, 96 pages.

Illumina, HCS 1.4/RTA 1.12 Theory of Operation, 2010, 32 pages.

Cacho, Base-Calling of High-throughput Sequencing Data Using a Random Effects Mixture Model, UC Riverside, Dec. 2016, 102 pages.

Zhou et. al., Incorporating Side-Channel Information into Convolutional Neural Networks for Robotic Tasks, 2017, 7 pages.

Linder, Modeling the intronic regulation of Alternative Splicing using Deep Convolutional Neural Nets, KTH Institute of Technology, dated Jun. 14, 2015, 53 pages.

(56) References Cited

OTHER PUBLICATIONS

Bentley et al., Accurate Whole Human Genome Sequencing using Reversible Terminator Chemistry, Nature, Nov. 2008, 21 pages.
Ilumina, Calculating Percent Passing Filter for Patterned and Nonpatterned Flow Cells, 2017, 2 pages.
Fritzilas, An Overview of Illumina's Sequencing Technology and its Applications, University of Primorska, dated Mar. 4, 2011, 47 pages.
Stenson, P. D. et al. The Human Gene Mutation Database—building a comprehensive mutation repository for clinical and molecular genetics, diagnostic testing and personalized genomic medicine. Hum. Genet. 133, 1-9 (2014).
Alipanahi, et. al., "Predicting the Sequence Specificities of DNA and RNA Binding Proteins by Deep Learning", Aug. 2015, 9pgs.
Angermueller, et. al., "Accurate Prediction of Single Cell DNA Methylation States Using Deep Learning", Apr. 11, 2017, 13pgs.
Ching, et. al., "Opportunities and Obstacles for Deep Learning in Biology and Medicine", Jan. 19, 2018, 123pgs.
Ching, et. al., "Opportunities and Obstacles for Deep Learning in Biology and Medicine", May 26, 2017, 47pgs.
Gu, et. al., "Recent Advances in Convolutional Neural Networks", Jan. 5, 2017, 37pgs.
Leung, et. al., "Deep learning of the tissue regulated splicing code", 2014, 9pgs.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
Macarthur, D. G. et al. Guidelines for investigating causality of sequence variants in human disease. Nature 508, 469-476 (2014).
Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755 (2011).
Rehm, H. L. Evolving health care through personal genomics. Nat. Rev. Genet. 18, 259-267 (2017).
Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project—300 genomes from 142 diverse populations. Nature 538, 201-206 (2016).
Genomes Project Consortium. et al. A global reference for human genetic variation. Nature 526, 68-74 (2015).
Liu, X., Jian, X. & Boerwinkle, E. dbNSFP—a lightweight database of human nonsynonymous SNPs and their functional predictions. Human. Mutat. 32, 894-899 (2011).
Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).
Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158(2017).

Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
De Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP—the NCBI database of genetic variation. Nucleic Acids Res. 29, 308-211 (2001).
Schrago, C. G., & Russo, C. A. Timing the origin of New World monkeys. Mol. Biol. Evol. 20, 1620-1625 (2003).
Landrum, M. J. et al. ClinVar—public archive of interpretations of clinically relevant variants. Nucleic Acids Res. 44, D862-868 (2016).
Brandon, E. P., Idzerda, R. L. & McKnight, G. S. Targeting the mouse genome—a compendium of knockouts (Part II). Curr. Biol. 5, 758-765 (1995).
Lieschke, J. G. & Currie, P. D. Animal models of human disease— zebrafish swim into view. Nat. Rev. Genet. 8, 353-367 (2007).
Sittig, L. J. et al. Genetic background limits generalizability of genotype—phenotype relationships. Neuron 91, 1253-1259 (2016).
Bazykin, G. A. et al. Extensive parallelism in protein evolution. Biol. Direct 2, 20, 13 pages (2007).
Ng, P. C., & Henikoff, S. Predicting deleterious amino acid substitutions. Genome Res. 11, 863-874 (2001).
Adzhubei, I. A. et al. A method and server for predicting damaging missense mutations. Nat. Methods 7, 248-249 (2010).
Chun, S. & Fay, J. C. Identification of deleterious mutations within three human genomes. Genome Res. 19, 1553-1561 (2009).
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations—application to cancer genomics. Nucleic Acids Res. 39, e118 (2011), 14pgs.
Dong, C. et al. Comparison and integration of deleteriousness prediction methods for nonsynonymous SNVs in whole exome sequencing studies. Hum. Mol. Genet. 24, 2125-2137 (2015).
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels. PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].
Illumina, Reducing Whole-Genome Data Storage Footprint, Illumina Whitepaper, 2010-2014, 4 pages.
Badrinarayanan et. al., SegNet: A Deep Convolutional Encoder-Decoder Architecture for Image Segmentation, dated Oct. 10, 2016, 14 pages.
Li et. al., CS231 Lecture 13 Segmentation and Attention, Stanford University, dated Feb. 24, 2016, 133 pages.
Whiteford et. al., Swift: Primary data analysis for the Illumina Solexa sequencing platform, Bioinformatics, vol. 25, No. 17, 2009, pp. 2194-2199, 7 pages.
Schilling, The Effect of Batch Normalization on Deep Convolutional Neural Networks, KTH Royal Institute of Technology, 2016, 113 pages.

(56)         References Cited

OTHER PUBLICATIONS

Tutorial Image Segmentation, BoofCV, 6 pages, retrieved on Jul. 23, 2021. Retrieved from [URL: https://boofcv.org/index.php?title= Tutorial_Image_Segmentation ].

Illumina, Understanding Illumina Quality Scores, dated Apr. 23, 2014, 2 pages.

Yue et al., Deep Learning for Genomics: A Concise Overview, dated May 8, 2018, 40 pages.

Zhang et al., Estimating Phred scores of Illumina base calls by logistic regression and sparse modeling, Bio Med Central Bioinformatics, 2017, 14 pages.

Renaud et al., freelbis: an efficient base caller with calibrated quality scores for Illumina sequencers, dated Mar. 6, 2013, 2 pages.

Kircher, Improving data quality of the Illumina Genome Analyzer platform, Max Planck Institute for Evolutionary Anthropology, dated Oct. 24, 2009, 46 pages.

Mitra et. al., Strategies for Achieving High Sequencing Accuracy for Low Diversity Samples and Avoiding Sample Bleeding Using Illumina Platform, PLOS One, published Apr. 10, 2015, 21 pages.

Datta et. al., Statistical Analyses of Next Generation Sequence Data: A Partial Overview, Journal of Proteomics and Bioinformatics, vol. 3, Issue 6, 2010, 8 pages.

Erlich et. al., Alta-Cyclic: a self-optimizing base-caller for next generation sequencing, Nature Methods, Aug. 2008, 7 pages.

Kao et. al., Algorithms for Next-Generation High-Throughput Sequencing Technologies, University of California, Berkeley, 2011, 106 pages.

Kircher et. al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].

Teng et. al., Chiron: translating nanopore raw signal directly into nucleotide sequence using deep learning, GigaScience, 7, 2018, 9 pages.

Ratkovic, Deep Learning Model for Base Calling of MinION Nanopore Reads, dated Jun. 2017, 48 pages.

Teng et. al., Chiron: translating nanopore raw signal directly into nucleotide sequence using deep learning, dated Aug. 23, 2017, 10 pages.

Stoiber et. al., BasecRAWller: Streaming Nanopore Basecalling Directly from Raw Signal, dated May 1, 2017, 15 pages.

Li et. al., DeepSimulator: a deep simulator for Nanopore sequencing, Bioinformatics 34(17), 2018, pp. 2899-2908, 10 pages.

Wick et. al., Performance of neural network basecalling tools for Oxford Nanopore sequencing, dated Feb. 7, 2019, 14 pages.

Ledergerber et. al., Base-calling for next-generation sequencing platforms, Briefings in Bioinformatics vol. 12, No. 5, pp. 489-497, dated Jan. 18, 2011, 9 pages.

Sheikh et. al., Chapter 5 Base-Calling for Bioinformaticians, 2012, 17 pages.

Kriseman et. al., BING: Biomedical informatics pipeline for Next Generation Sequencing, Journal of Biomedical Informatics, vol. 43, 2010, pp. 428-434, 7 pages.

Das et. al., Model-based sequential base calling for Illumina sequencing, IEEE, 2010, 4 pages.

Shamaiah et. al., Base calling error rates in next-generation DNA sequencing, IEEE Statistical Signal Processing Workshop, 2012, 4 pages.

Wolowski, High-quality, high-throughput measurement of protein-DNA binding using HiTS-FLIP, Ludwig Maxmilian University, 2016, 251 pages.

Bravo et. al., Model-Based Quality Assessment and Base-Calling for Second-Generation Sequencing Data, Biometrics, 2009, 10 pages.

Illumina, RTA Theory of Operation, 2009, 8 pages.

Dash et. al., Artificial Intelligence and Evolutionary Computations in Engineering Systems, Advances in Intelligent Systems and Computing, vol. 1056, Springer 2020, 781 pages.

Ahmed, SIGNET: A Neural Network Architecture for Predicting Protein-Protein Interactions, The University of Western Ontario, dated May 7, 2017, 84 pages.

Deepa J, Development of Fully Automated Image Analysis Method for High Density cDNA and array CGH Microarray based genomic studies, Cochin University of Science and Technology, Mar. 2013, 232 pages.

Zhang et. al., Nanopore basecalling from a perspective of instance segmentation, BMC Bioinformatics, 2020, 9 pages.

Kao et. al., naiveBayesCall: An Efficient Model-Based Base-Calling Algorithm for High-Throughput Sequencing, Journal of Computational Biology, dated Mar. 2011, 16 pages.

Wick et. al., Performance of neural network basecalling tools for Oxford Nanopore sequencing, Genome Biology, 2019, 10 pages.

Baek et. al., LncRNAnet: long non-coding RNA identification using deep learning, Bioinformatics, vol. 34 (22), 2018, pp. 3889-3897, 9 pages.

Evans et. al., Estimating Change-Points in Biological Sequences via the Cross-Entropy Method, dated Sep. 20, 2010, 17 pages.

Shen et. al., ParticleCall: A particle filter for base calling in next-generation sequencing systems, BMC Bioinformatics, 2012, 10 pages.

Peresini et. al., Nanopore Base Calling on the Edge, dated Nov. 9, 2020, 15 pages.

Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.

Wang et. al., DeepDNA: a hybrid convolutional and recurrent neural network for compressing human mitochondrial genomes, IEEE International Conference on Bioinformatics and Biomedicine, 2018, 5 pages.

PCT/US2020/024092, International Preliminary Report on Patentability (IPRP), dated Jun. 30, 2021, 30 pages.

PCT/US2020/024091 International Preliminary Report and Patentability (IPRP), dated Jun. 30, 2021, 32 pages.

PCT/US2020/024088 International Preliminary Report on Patentability (IPRP), dated Jun. 30, 2021, 35 pages.

PCT/US2020/024087 International Preliminary Report on Patentability (IPRP), dated Jun. 30, 2021, 26 pages.

PCT/US2021/018917 Internation Search Report and Written Opinion, dated Jul. 1, 2021, 15 pages.

Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].

PCT/US2020/033281, Second Article 34 Amendment Letter in response to Second Written Opinion, dated Jul. 10, 2021, 4 pages.

Albrecht et. al., Deep learning for single-molecule science, Nanotechnology (28), dated 2017, 423001, 11 pages.

MiSEQ: Imaging and Base Calling: Illumina, Inc. Online Training Course, dated Jan. 1, 2013 [retrieved on Jul. 13, 2020] , Retrieved from <URL: https://support.illumina.com/training.html >, 13 pages.

MiSEQ: Imaging and Base Calling Script, retrieved on [Jun. 14, 2021], Retrieved from the internet <URL: https://support.illumina.com/content/dam/illumina-support/courses/MiSeq_Imaging_and_Base_Calling/story_content/external_files/ MiSeq%20Imaging%20and%20Base%20Calling%20Script.pdf >.

PCT/US2020/024087 PCT Direct Letter, dated Mar. 21, 2020, 5 pages.

PCT/US2020/024087 International Search Report and Written Opinion, dated Aug. 28, 2020, 24 pages.

PCT/US2020/024087 Article 34 Amendment, filed Mar. 21, 2020, 7 pages.

PCT/US2020/024087 Second Written Opinion, dated Apr. 7, 2021, 12 pages.

PCT/US2020/024087 Article 34 Letter Response to Second Written Opinion, dated May 7, 2021, 7 pages.

Zhao et. al., Object detection with Deep Learning: A Review, dated Jul. 15, 2018, 22 pages.

Lee et. al., Fast Object Localization Using a CNN Feature Map Based Multi-Scale Search, dated Apr. 12, 2016, 16 pages.

(56) References Cited

OTHER PUBLICATIONS

PCT/US2020/24088 PCT Direct Letter, filed Mar. 21, 2020, 4 pages.

PCT/US2020/024088 Article 34 Letter in response to Second Written Opinion, dated May 28, 2021, 9 pages.

PCT/US2020/024088 Second Written Opinion, dated Apr. 20, 2021, 17 pages.

PCT/US2020/024088 International Search Report and Written Opinion, dated Sep. 7, 2020, 29 pages.

PCT/US2020/024088 Article 34 Letter in Response to Written Opinion, dated Mar. 9, 2021, 11 pages.

PCT/US2020/024088 Partial Search Report and Invitation to Pay Fees, dated Jul. 8, 2020, 22 pages.

Misiunas et. al., QuipuNet: convolutional neural network for single-molecule nanopore sensing, dated May 30, 2018, 7 pages.

Boza et. al., Deep Recurrent Neural Networks for Base Calling in MinION Nanopore Reads, dated Mar. 30, 2016, 12 pages.

Kao et. al., BayesCall: A model-based base-calling algorithm for high-throughput short-read sequencing, Genome Research (19), pp. 1884-1895, dated 2009.

Rang et. al., From squiggle to basepair: computational approaches for improving nanopore sequencing read accuracy, Genome Biology 2018, (19), 30.

Wang et. al., An adaptive decorrelation method removes Illumina DNA base-calling errors caused by crosstalk between adjacent clusters, Scientific Reports, published Feb. 20, 2017, 11 pages.

Cacho et. al., A comparison of Base Calling Algorithms for Illumina Sequencing Technology, dated Oct. 5, 2015, Briefings in Bioinformatics 2016 (17), 786-795.

PCT/US2020/024091 PCT Direct Letter, dated Mar. 21, 2020, 5 pages.

PCT/US2020/024091 Partial Search Report and Invitation to Pay Fee, dated Jul. 3, 2020, 17 pages.

PCT/US2020/024091 International Search Report and Written Opinion, dated Oct. 23, 2020, 24 pages.

PCT/US2020/024091 Article 34 Letter in Reponse to International Search Report and Written Opinion, filed Mar. 8, 2021, 10 pages.

PCT/US2020/024091 Second Article 34 Amendment Letter, dated Mar. 22, 2021, 10 pages.

PCT/US2020/024091 Written Opinion of the International Preliminary Examining Authority (Second Written Opinon), dated Apr. 20, 2021, 14 pages.

PCT/US2020/024091 Second Article 34 Amendment in response to Second Written Opinion, dated May 30, 2021, 9 pages.

Luo et. al., G-softmax: Improving Intra-class Compactness and Inter-class Separability of Features, dated Apr. 8, 2019, 15 pages.

Luo et. al., A multi-task convolutional deep neural network for variant calling in single molecule sequencing, Nature Communications (10), No. 1, dated Mar. 1, 2019.

Kingma et. al., Adam: A method for Stochastic Optimization, ICLR 2015, dated Jul. 23, 2015.

Luo et. al., Skyhawk: An Artificial Neural Network-based discriminator for reviewing clinically significant genomic variants, dated Jan. 28, 2019, 8 pages.

MiSEQ: Imaging and Base Calling: Illumina, Inc. Online Training Course, colored version, [retrieved on Oct. 11, 2020], Retrieved from <URL: https://support.illumina.com/training.html >, 9 pages.

PCT/US2020/024092 PCT Direct Letter, dated Mar. 21, 2020, 5 pages.

PCT/US2020/024092 Partial Search Report and Invitation to Pay Fees, dated Sep. 11, 2020, 22 pages.

PCT/US2020/024092 International Search Report and Written Opinion, dated Nov. 2, 2020, 24 pages.

PCT/US2020/024092 Article 34 Amendment in Response to International Search Report and Written Opinion, dated Mar. 4, 20221, 7 pages.

PCT/US2020/024092 Second Written Opinion dated Apr. 7, 2021, 13 pages.

PCT/US2020/024092 Article 34 Amendment Response to Second Written Opinion, dated May 7, 2021, 10 pages.

PCT/US2021/018910—Partial Search Report and Invitation to Pay Fees dated May 31, 2021, 14 pgs.

PCT/US2020/033280 International Search Report and Written Opinion, dated Jul. 22, 2020, 18 pages.

PCT/US2020/033280 Article 34 Amendment, dated Apr. 19, 2021, 10 pages.

PCT/US2020/033281 International Search Report and Written Opinion, dated Aug. 14, 2020, 15 pages.

Kircher et. al., Improved base-calling for the Illumina Genome Analyzer using Machine Learning Strategies, Genome Biology, published Aug. 14, 2009, 9 pages.

PCT/US2020/033281 Second Written Opinion, dated May 10, 2021, 8 pages.

Angermueller, Christof, et. al., Deep learning for computational biology, Molecular Systems Biology, dated Jun. 6, 2016, 16 pages.

PCT/US2021/018258 International Search Report and Written Opinion, dated May 26, 2021, 17 pages.

Smith et. al., Barcoding and demultiplexing Oxford nanopore native RNA sequencing reads with deep residual learning, bioRxiv, dated Dec. 5, 2019, 18 pages.

PCT/US2021/018910 Partial Search Report and Invitation to pay fee, dated May 31, 2021, 14 pages.

Chen, C., Khaleel, S.S., Huang, H., & Wu, C.H. (2014). Software for pre-processing Illumina next-generation sequencing short read sequences. Source code for Biology and medicine, 9, 1-11. (Year: 2014).

PCT/US2021/018422 International Search Report and Written Opinion, dated Jun. 10, 2021, 12 pages.

Aggarwal, Neural Networks and Deep Learning: A Textbook, Springer, dated Aug. 26, 2018, 512 pages.

Wang et. al., Deep Neural Network Approximation for Custom Hardware: Where We've Been, Where We're Going, Cornell University, dated Jan. 21, 2019, 37 pages.

Lavin et. al., Fast Algorithms for Convolutional Neural Networks, dated Nov. 10, 2015, 9 pages.

Liu et. al., A Uniform Architecture Design for Accelerating 2D and 3D CNNs on FPGAs, published Jan. 7, 2019, 19 pages.

PCT/US2021/018427 International Search Report and Written Opinion, dated Jun. 1, 2021, 15 pages.

PCT/US2021/018913 International Search Report and Written Opinion, dated Jun. 10, 2021, 11 pages.

Zeng et. al., Causalcall: Nanopore Basecalling Using a Temporal Convolutional Network, dated Jan. 20, 2020, 11 pages.

PCT/US2021/018915 International Search Report and Written Opinion, dated Jun. 15, 2021, 13 pages.

Kwon et. al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.

Sze et. al., Efficient Processing of Deep Neural Networks: A Tutorial and Survey, Cornell University Library, dated Mar. 27, 2017, 21 pages.

Sundaram, L. et. al., "Predicitng the clinical impact of human mutation with deep neural networks", Nat. Genet. 50, 1161-1170 (2018).

Jaganathan, K. et. al., "Predicting splicing from primary sequence with deep learning", Cell 176, 535-548, (2019).

Kircher, Martin, et al. "A general framework for estimating the relative pathogenicity of human genetic variants." Nature genetics 46.3 (2014): 310. (Year:2014).

Henikoff, S. & Henikoff, J. G. Amino acid substitution matrices from protein blocks. Proc. Natl. Acad. Sci. USA 89, 10915-10919 (1992).

Li, W. H., Wu, C. I. & Luo, C. C. Nonrandomness of point mutation as reflected in nucleotide substitutions in pseudogenes and its evolutionary implications. J. Molec. Evol. 21, 58-71 (1984).

Grantham, R. Amino acid difference formula to help explain protein evolution. Science 185, 862-864 (1974).

LeCun, Y., Botlou, L., Bengio, Y., & Haffner, P. Gradient based learning applied to document recognition. Proc. IEEE 86, 2278-2324 (1998).

(56)  References Cited

OTHER PUBLICATIONS

Vissers, L. E., Gilissen, C., & Veltman, J. A. Genetic studies in intellectual disability and related disorders. Nat. Rev. Genet. 17, 9-18 (2016).

Neale, B. M. et al. Patterns and rates of exonic de novo mutations in autism spectrum disorders. Nature 485, 242-245 (2012).

Sanders, S. J. et al. De novo mutations revealed by whole-exome sequencing are strongly associated with autism. Nature 485, 237-241 (2012).

De Rubeis, S. et al. Synaptic, transcriptional and chromatin genes disrupted in autism. Nature 515, 209-215 (2014).

Deciphering Developmental Disorders Study. Large-scale discovery of novel genetic causes of developmental disorders. Nature 519, 223-228 (2015).

Deciphering Developmental Disorders Study. Prevalence and architecture of de novo mutations in developmental disorders. Nature 542, 433-438 (2017).

Iossifov, I. et al. The contribution of de novo coding mutations to autism spectrum disorder. Nature 515, 216-221 (2014).

Zhu, X. Need, A. C., Petrovski, S. & Goldstein, D. B. One gene, many neuropsychiatric disorders: lessons from Mendelian diseases. Nat. Neurosci. 17, 773-781, (2014).

Leffler, E. M. et al. Revisiting an old riddle: what determines genetic diversity levels within species? PLoS Biol. 10, e1001388 (2012), 9pages.

Estrada, A. et al. Impending extinction crisis of the world's primates—why primates matter. Sc. Adv. 3, e1600946 (2017), 17 pages.

Kent, W. J. et al. The human genome browser at UCSC. Genome Res. 12, 996-1006 (2002).

Tyner, C. et al. The UCSC Genome Browser database—2017 update. Nucleic Acids Res. 45, D626-D634 (2017).

Kabsch, W., & Sander, C. Dictionary of protein secondary structure—pattern recognition of hydrogen-bonded and geometrical features. Biopolymers 22, 2577-2637 (1983).

Joosten, R. P. et al. A series of PDB related databases for everyday needs. Nucleic Acids Res. 39, 411-419 (2011).

He, K, Zhang, X., Ren, S., & Sun, J. Identity mappings in deep residual networks. in 14th European Conference on Computer Vision—ECCV 2016. ECCV 2016. Lecture Notes in Computer Science, vol. 9908; 630 6, 15 (Springer, Cham, Switzerland; 2016).

Ionita-Laza, I., McCallum, K., Xu, B., & Buxbaum, J. D. A spectral approach integrating functional genomic annotations for coding and noncoding variants. Nat. Genet. 48, 214-220 (2016).

Li, B. et al. Automated inference of molecular mechanisms of disease from amino acid substitutions. Bioinformatics 25, 2744-2750 (2009).

Lu, Q. et al. A statistical framework to predict functional non-coding regions in the human genome through integrated analysis of annotation data. Sci. Rep. 5, 10576 (2015), 13pgs.

Shihab, H. A. et al. Predicting the functional, molecular, and phenotypic consequences of amino acid substitutions using hidden Markov models. Human. Mutat. 34, 57-65 (2013).

Davydov, E. V. et al. Identifying a high fraction of the human genome to be under selective constraint using Gerp++. PLoS Comput. Biol. 6, Dec. 2, 2010, 13 pages.

Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).

Jain, S., White, M., Radivojac, P. Recovering true classifier performance in positive-unlabeled learning. in Proceedings Thirty-First AAAI Conference on Artificial Intelligence. 2066-2072 (AAAI Press, San Francisco; 2017).

De Ligt, J. et al. Diagnostic exome sequencing in persons with severe intellectual disability. N. Engl. J. Med. 367, 1921-1929 (2012).

Iossifov, I. et al. De novo gene disruptions in children on the autistic spectrum. Neuron 74, 285-299 (2012).

O'Roak, B. J. et al. Sporadic autism exomes reveal a highly interconnected protein network of de novo mutations. Nature 485, 246-250 (2012).

Rauch, A. et al. Range of genetic mutations associated with severe non-syndromic sporadic intellectual disability—an exome sequencing study. Lancet 380, 1674-1682 (2012).

Epi, K. C. et al. De novo mutations in epileptic encephalopathies. Nature 501, 217-221 (2013).

EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).

Gilissen, C. et al. Genome sequencing identifies major causes of severe intellectual disability. Nature 511, 344-347 (2014).

Lelieveld, S. H. et al. Meta-analysis of 2,104 trios provides support for 10 new genes for intellectual disability. Nat. Neurosci. 19, 1194-1196 (2016).

Famiglietti, M. L. et al. Genetic variations and diseases in UniProtKB Swiss-Prot—the ins and outs of expert manual curation. Human. Mutat. 35, 927-935 (2014).

Horaitis, O., Talbot, C. C.Jr., Phommarinh, M., Phillips, K. M., & Cotton, R. G. A database of locus-specific databases. Nat. Genet. 39, 425 (2007).

NL 2023311 NL Search Report, dated Mar. 24, 2020, 15 pages.

NL 2023312, NL Search Report, dated Mar. 24, 2020, 22 pages.

NL 2023317, NL Search Report, dated Mar. 24, 2020, 16 pages.

NL 2023316, NL Search Report, dated Mar. 23, 2020, 15 pages.

MX/a/2020/014288 First Office Action, dated Mar. 10, 2021, 2 pages.

MX/a/2020/014288 Response to First Office Action, dated May 5, 2021, 390 pages.

U.S. Appl. No. 16/825,991—Notice of Allowance dated Aug. 5, 2021, 10 pages.

Krishnakumar et al., Systematic and stochastic influences on the performance of the MinION nanopore sequencer across a range of nucleotide bias, Scientific Reports, published Feb. 16, 2018, 13 pages.

Tegfalk, Application of Machine Learning techniques to perform base-calling in next-generation DNA sequencing, KTH Royal Institue of Technology, dated 2020, 53 pages.

U.S. Appl. No. 16/826,168—Office Action dated Aug. 31, 2021, 55 pages.

Kircher-etal_Improved-base-calling-for-the-Illumina-Genome-Analyzer-using-machine-learning-strategies_14August2009_10pages.

Albrecht et al., Deep learning for single molecule science, Nanotechnology, dated Sep. 18, 2017, 11 pages.

U.S. Appl. No. 16/825,987—Office Action (Quayle) dated Oct. 19, 2021, 85 pages.

PCT/US2021047763—International Search Report and Written Opinion, dated Dec. 20, 2021, 11 pages.

PCT/US2021/018422 Second Written Opinion, dated Feb. 4, 2022, 8 pages.

Adriana Romero et. al., FitNets: Hints for Thin Deep Nets, published Mar. 27, 2015, 13 pages.

U.S. Appl. No. 16/874,599—Notice of Allowance dated Dec. 3, 2021, 12 pages.

U.S. Appl. No. 16/825,987—Response to Office Action (Quayle) dated Oct. 19, 2021, filed Jan. 13, 2022, 11 pages.

U.S. Appl. No. 16/825,987—Notice of Allowance, dated Jan. 28, 2022, 12 pages.

U.S. Appl. No. 16/825,987—Supplemental Notice of Allowance, dated Feb. 7, 2022, 8 pages.

U.S. Appl. No. 16/826,168—Response to Office Action dated Aug. 31, 2021, filed Jan. 31, 2022, 15 pages.

CN 2020800036223—Voluntary Amendments, filed May 20, 2021, 26 pages.

EP 20719053.9—Rules 161(2) and 162 Communication, dated Oct. 28, 2021, 3 pages.

IL 279522—Notice Before Acceptance (in Hebrew), dated Aug. 1, 2021, 2 pages.

IL 279522—Response to Notice Before Acceptance dated Aug. 1, 2021, filed Nov. 28, 2021, 3 pages.

(56) References Cited

OTHER PUBLICATIONS

KR 10-2020-7037712—Voluntary Amendments with translation, dated Nov. 9, 2021, 7 pages.
EP 20719052.1—Rules 161(1) and 162 Communication, dated Oct. 28, 2021. 3 pages.
IL 279525—Notice Before Acceptance (in Hebrew), dated Aug. 1, 2021, 2 pages.
IL 279525—Response to Notice Before Acceptance dated Aug. 1, 2021, filed Nov. 28, 2021, 4 pages.
KR 10-2020-7037713—Voluntary Amendments with translation, dated Nov. 9, 2021, 26 pages.
ZA 2020/07998—Notice of Allowance, dated Aug. 12, 2021, 2 pages.
EP 20718112.4—Rules 161(2) and 162 Communication, dated Oct. 28, 2021, 3 pages.
IL 279527—Notice Before Examination (in Hebrew), dated Aug. 1, 2021, 2 pages.
IL 279527—Response to Notice Before Examination dated Aug. 1, 2021, filed Nov. 28, 2021, 3 pages.
KR 10-2021-7003269—Voluntary Amendments with translation, dated Nov. 9, 2021, 7 pages.
ZA 2020/07999—Notice of Allowance, dated Aug. 12, 2021, 2 pages.
EP 20719294.9—Rules 161(1) and 162 Communication, dated Oct. 28, 2021, 3 pages.
IL 281668—Notice Before Examination, dated Oct. 10, 2021, 2 pages.
IL 281668—Response to Notice Before Examination dated Oct. 10, 2021, filed Feb. 8, 2022, 4 pages.
KR 10-2021-7009877—Voluntary Amendments with translation, dated Nov. 9, 2021, 21 pages.
EP 20757979.8—Rules 161(2) and 162 Communication, dated Oct. 28, 2021, 3 pages.
IL 279533—Notice Before Examination, dated Aug. 1, 2021, 2 pages.
IL 279533—Response to Notice Before Examination dated Aug. 1, 2021, filed Nov. 29, 2021, 3 pages.
KR 10-2021-7003270—Voluntary Amendments with translation, dated Nov. 9, 2021, 29 pages.
ZA 2020/08000—Notice of Acceptance, dated Aug. 12, 2021, 2 pages.
Robinson et al., Computational Exome and Genome Analysis—Chapter 3 Illumina Technology, dated 2018, 25 pages.
Wang et. al., An adaptive decorrelation method removes Illumina DNA base-calling errors caused by crosstalk between adjacent clusters—with Supplemental Materials, Scientific Reports, published Feb. 20, 2017, 17 pages.
PCT/US2020/033280—International Preliminary Report on Patentability, dated Jul. 23, 2021, 11 pages.
Pfeiffer et. al., Systematic evaluation of error rates and causes in short samples in next-generation sequencing, Scientific Reports, published Jul. 19, 2018, 14 pages.
PCT/US2020/033281—International Preliminary Report on Patentability, dated Aug. 31, 2021, 10 pages.
Gerencer, T. (Oct. 30, 2019). Parallel Computing And Its Modern Uses I HP® Tech Takes. Www.hp.com. https://www.hp.com/us-en/shop/tech-takes/parallel-computing-and-its-modern-uses (Year: 2019.
Grange, NGS: the basics, Institut Jacques Monod, dated Jun. 26, 2000, 59 pages.
Illumina CMOS Chip and One-Channel SBS Chemistry, Illumina Inc, 2018, 4 pages.
Illumina, GA Bootcamp, Sequencing Module 3 : Overview, Broad Institute, 73 pages, retrieved on Jul. 22, 2021T, Retrieved from [URL: https://www.google.com/search?q=broad+institute+sequencing+module+3 t-overview&client=firefox-b1e&sxsrf-ALeKk02079LD_qrHqvhfFGRnNCUw8Z6QJA%3A1628296030482&ei=XIMNYYHMPi-gS61onoCQ&q=broad+institute+sequencing+module+3roverview&gs_lcp=Cgdnd3Mtd216EAM6BwgjELADECdKBQg6EgExSgQIQRgBUPn9AVj5_QFglZQCaAFwAHgAgAFt.

Mansar, Y. (Feb. 15, 2020). Build powerful lightweight models using knowledge distillation. Medium. https://towardsdatascience.com/build-powerful-light-weight-models-using-knowledge-distillation-on-618f69b569d 9#:-:text=The%20basic%20idea%20behind%20Knowledge,try%20to%20mimic%20the%20Teacher. (Year: 2020).
Massingham et. al., All Your Base: a fast and accurate probabilistic approach to base calling, European Bioinformatics 18 Institute, 22 pages, [retrieved on Jul. 2, 2021], Retrieved from the internet [URL: https://www.ebi.ac.uk/goldman-srv/ AYB/references/ayb.pdf].
NL 2023310 NL Search Report, dated Mar. 5, 2020, 17 pages.
Python Implementation of the color map function for the PASCAL VOC data set.Github,4 pages.retrievedon Jul. 23, 2021. Retrieved from [URL: https://gist.github.com/wllf/a45330adebe573-ed06d450c8419ae ].
Semantic Segmentation Examples—MATLAB and Simulink, 22 pages, (retrieved on Jul. 21, 2021), Retrieved from the Internet [URL: https://www.mathworks.com/help/vision/ug/semantic-segmentation-examples.html ].
Turing. (Feb. 11, 2022). Understanding feed forward neural networks in deep learning. Turing Enterprises Inc. https://www.turing.com/kb/mathematical-formulation-of-feed-forward-neural-network#why-are-neural-networks-used? (Year: 2020).
Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages.
U.S. Appl. No. 16/825,991—Notice of Allowance dated Apr. 19, 2021, 14 pages.
Arpali et al., High-throughput screening of large volumes of whole blood using structured illumination and fluoresecent on-chip imaging, Lab on a Chip, United Kingdom, Royal Society of Chemistry, Sep. 12, 2012, vol. 12, pp. 4968-4971.
Liu et. al., 3D Stacked Many Core Architecture for Biological Sequence Analysis Problems, 2017, Int J Parallel Prog, 45:1420-1460.
Wu et. al., FPGA-Based DNA Basecalling Hardware Acceleration, in Proc. IEEE 61st Int. Midwest Symp. Circuits Syst., Aug. 2018, pp. 1098-1101.
Wu et. al., FPGA-Accelerated 3rd Generation DNA Sequencing, in IEEE Transactions on Biomedical Circuits and Systems, vol. 14, Issue 1, Feb. 2020, pp. 65-74.
Prabhakar et. al., Plasticine: A Reconfigurable Architecture for Parallel Patterns, ISCA '17, Jun. 24-28, 2017, Toronto, ON, Canada.
Lin et. al., Network in Network, in Proc. of ICLR, 2014.
Sifre, Rigid-motion Scattering for Image Classification, Ph.D. thesis, 2014.
Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et. al., ShuffleNet: An Extremely Efficient Convolutional Neural Network for Mobile Devices, 2017.
He et. al., Deep Residual Learning for Image Recognition, in Proc. of CVPR, 2016.
Xie et. al., Aggregated Residual Transformations for Deep Neural Networks, in Proc. of CVPR, 2017.
Howard et. al., Mobilenets: Efficient Convolutional Neural Networks for Mobile Vision Applications, 2017.
Sandler et. al., MobileNetV2: Inverted Residuals and Linear Bottlenecks, 2018.
Qin et. al., FD-MobileNet: Improved MobileNet with a Fast Downsampling Strategy, 2018.
Chen et. al., Rethinking atrous convolution for semantic image segmentation, 2017.
Huang et. al., Speed/accuracy trade-offs for modern convolutional detectors, 2016.
Oord, Dieleman et. al., WAVENET: A Generative Model for Raw Audio, 2016.
Arik et. al., Deep Voice: Real-time Neural Text-to-Speech, 2017.
Yu et. al., Multi-Scale Context Aggregation by Dilated Convolutions, 2016.
He et. al., Deep Residual Learning for Image Recognition, 2015.
Srivastava et. al., Highway Networks, 2015.

(56)          References Cited

OTHER PUBLICATIONS

Huang et. al., Densely Connected Convolutional Networks, 2017.
Szegedy et. al., Going Deeper with Convolutions, 2014.
Ioffe et. al., Batch Normalization Accelerating Deep Network Training by Reducing Internal Covariate Shift, 2015.
Wolterink et. al., Dilated Convolutional Neural Networks for Cardiovascular MR Segmentation in Congenital Heart Disease, 2017.
Piqueras, Autoregressive Model Based on a Deep Convolutional Neural Network for Audio Generation, Tampere University of Technology, 2016.
Wu, Introduction to Convolutional Neural Networks, Nanjing University, 2017.
scikit-image/peak.py at master, Github, retrieved on Jun. 8, 2021, 10 pages, Retrieved from the internet <URL: https://github.com/scikit-image/scikitimage/blob/main/skimage/feature/peak.py>.
3.3.9.11.Watershed and random walker for segmentation, Scipy lecture notes, 2 pages. [retrieved on Jun. 8, 2021] Retrieved from the internet <URL: http:scipy-lectures.org/packages/scikit-image/auto_examples/plot_segmentations.html>.
Mordvintsev et al., Image Segmentation with Watershed Algorithm, Revision 43532856, 2013, 6 pages. [retrieved on Jun. 8, 2021] Retrieved from the Internet <URL: https://opencv-python-tutroals.readthedocs.io/en/latest/py_tutorials/py_imgproc/py_watershed/py_watershed.html>.
Mzur, Watershed.py, Github, 3 pages. [retrieved on Jun. 8, 2021] Retrieved from the internet <URL: https://github.com/mzur/watershed/blob/master/Watershed.py>.
Thakur et. al., A Survey of Image Segmentation Techniques, International Journal of Research in Computer Applications and Robotics, vol. 2, Issue 4, Apr. 2014, p. 158-165.
Long et. al., Fully Convolutional Networks for Semantic Segmentation, IEEE Transactions on Pattern Analysis and Machine Intelligence, vol. 39, Issue 4, Apr. 1, 2017, 12 pages.
Ronneberger et. al., U-net: Convolutional networks for biomedical image segmentation, in International Conference on Medical Image computing and computer assisted intervention, May 18, 2015, 8 pages.
Xie et. al., Microscopy cell counting and detection with fully convolutional regression networks, Computer methods in biomechanics and biomedical engineering, Imaging and Visualization, 6(3), pp. 283-292, 2018.
Xie, Y., et. al., Beyond classification: structured regression for robust cell detection using convolutional neural network, International conference on medical image computing and computer assisted intervention, Oct. 2015, 12 pages.
Snuverink, Deep Learning for Pixelwise Classification of Hyperspectral Images, Master of Science Thesis, Delft University of Technology, Nov. 23, 2017, 128 pages.
Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b >, 2 pages.
Assem, Predicting periodic and chaotic signals using Wavenets, Master of Science thesis, Delft University of Technology, Aug. 18, 2017, pp. 3-38.
Goodfellow et. al., Convolutional Networks, Deep Learning, MIT Press, 2016.
Illumina, "Indexed Sequencing Overview Guide", Document No. 15057455, v. 5, Mar. 2019.
PCT/US2020/024090 International Preliminary Report on Patentability, dated Apr. 13, 2021, 20 pages.
PCT/US2020/024090 Written Opinion of the International Preliminary Examining Authority, dated Dec. 22, 2020, 11 pages.
PCT/US2020/024090 PCT Direct Letter, filed Mar. 21, 2020, 5 pages.
PCT/US2020/024090 International Search Report, dated Aug. 31, 2020, 8 pages.
PCT/US2020/024090 Article 34 Amendment, dated Dec. 4, 2020, 6 pages.

PCT/US2020/024090 Article 34 Amendment, dated Mar. 18, 2021, 3 pages.
U.S. Appl. No. 16/825,987, filed Mar. 20, 2020, U.S. Pat. No. 11,347,965, May 31, 2022.
U.S. Appl. No. 16/825,991, filed Mar. 20, 2020, U.S. Pat. No. 11,210,554, Dec. 28, 2021.
U.S. Appl. No. 16/826,126, filed Mar. 20, 2020, US-2020-0302297-A1, Sep. 24, 2020, Pending.
U.S. Appl. No. 16/826,134, filed Mar. 20, 2020, US-2020-0327377-A1, Oct. 15, 2020, Pending.
U.S. Appl. No. 16/826,168, filed Mar. 21, 2020, US-2020-0302224-A1, Sep. 24, 2020.
U.S. Appl. No. 17/529,222, filed Nov. 17, 2021, US-2022-0147760-A1, May 12, 2022, Pending.
U.S. Appl. No. 17/827,612, filed May 27, 2022, Pending.
U.S. Appl. No. 16/874,633, filed May 14, 2020, US-2020-0364565-A1, Nov. 19, 2020.
U.S. Appl. No. 17/703,975, filed Mar. 24, 2022, Pending.
U.S. Appl. No. 17/175,546, filed Feb. 12, 2021, US-2021-0265009-A1, Aug. 26, 2021, Pending.
U.S. Appl. No. 17/180,542, filed Feb. 19, 2021, US-2021-0265017-A1, Aug. 26, 2021, Pending.
U.S. Appl. No. 17/176,151, filed Feb. 15, 2021, US-2021-0265018-A1, Aug. 26, 2021, Pending.
U.S. Appl. No. 17/411,980, filed Aug. 25, 2021, US-2022-0067489-A1, Mar. 3, 2022, Pending.
U.S. Appl. No. 17/687,551, filed Mar. 4, 2022, Pending.
U.S. Appl. No. 17/687,583, filed Mar. 4, 2022, Pending.
U.S. Appl. No. 17/179,395, filed Feb. 18, 2021, US-2021-0265016-A1, Aug. 26, 2021, Pending.
U.S. Appl. No. 17/180,480, filed Feb. 19, 2021, US-2021-0264266-A1, Aug. 26, 2021, Pending.
U.S. Appl. No. 17/180,513, filed Feb. 19, 2021, US-2021-0264267-A1, Aug. 26, 2021, Pending.
U.S. Appl. No. 17/687,586, filed Mar. 4, 2022, Pending.
U.S. Appl. No. 17/232,056, filed Apr. 15, 2021, Pending.
U.S. Appl. No. 17/468,411, filed Sep. 7, 2021, Pending.
U.S. Appl. No. 17/830,287, filed Jun. 1, 2022, Pending.
U.S. Appl. No. 17/830,316, filed Jun. 1, 2022, Pending.
U.S. Appl. No. 17/839,331, filed Jun. 13, 2022, Pending.
U.S. Appl. No. 17/703,935, filed Mar. 24, 2022, Pending.
U.S. Appl. No. 17/703,958, filed Mar. 24, 2022, Pending.
PCT/US2021/018427, Feb. 17, 2021, Pending.
PCT/US2020/024090, Mar. 21, 2020, WO 2020/191389, Sep. 24, 2020.
PCT/US2020/024087, Mar. 21, 2020, WO 2020/205296, Oct. 8, 2020.
PCT/US2020/024088, Mar. 21, 2020, WO 2020/191387, Sep. 24, 2020.
PCT/US2020/024091, Mar. 21, 2020, WO 2020/191390, Sep. 24, 2020.
PCT/US2020/024091, Mar. 22, 2020, WO 2020/191391, Sep. 24, 2020.
PCT/US2020/033280, May 15, 2020, WO 2020/232409, Nov. 19, 2020.
PCT/US2020/033281, May 15, 2020, WO 2020/232410, Nov. 19, 2020.
PCT/US2021/018258, Feb. 16, 2021, Pending.
PCT/US2021/018910, Feb. 19, 2021, Pending.
PCT/US2021/018422, Feb. 17, 2021, Pending.
PCT/US2021/047763, Aug. 26, 2021, Pending.
PCT/US2022/020460, Mar. 15, 2022, Pending.
PCT/US2022/020462, Mar. 15, 2022, Pending.
PCT/US2021/018913, Feb. 19, 2021, Pending.
PCT/US2021/018915, Feb. 19, 2021, Pending.
PCT/US2021/018917, Feb. 19, 2021, Pending.
PCT/US2022/021814, Mar. 24, 2022, Pending.
PCT/US2022/24911, Apr. 14, 2022, Pending.
PCT/US2022/24913, Apr. 14, 2022, Pending.
PCT/US2022/035564, Jun. 29, 2022, Pending.
PCT/US2022/035567, Jun. 29, 2022, Pending.
PCT/US2022/035847, Jun. 30, 2022, Pending.
PCT/US2022/24916, Apr. 14, 2022, Pending.

(56) References Cited

OTHER PUBLICATIONS

PCT/US2022/24918, Apr. 14, 2022, Pending.
Eraslan, G., Avsec, Ž., Gagneur, J. et al. Deep learning: new computational modelling techniques for genomics. Nature Reviews Genetic 20, 389-403 (2019). https://doi.org/10.1038/s41576-019-0122-6.
Hacteria Wiki, HiSeq2000—Next Level Hacking—Hackteria Wiki, retrieved on Apr. 12, 2021, retrieved from the internet [URL: https://www.hackteria.org/wiki/HiSeq2000_-_Next_Level_Hacking ], 42 pages.
Pei et al., A Topological Measurement for Weighted Protein Inter-action Network, IEEE Computational Systems Bioinformatics Con-ference dated 2005, 11 pages.
Assfalg et al., "3DString, A Feature String Kernel for 3D Object Classification on Voxelized Data", dated Nov. 6, 2006, 10 pages.
Bell, C. J. et al. Comprehensive carrier testing for severe childhood recessive diseases by next generation sequencing. Sci. Transl. Med. 3, Jan. 12, 2011, 28 pages.
Smedley, D. et al. A whole-genome analysis framework for effective identification of pathogenic regulatory variants in mendelian dis-ease. Am. J. Hum. Genet. 99, 595-606 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Hefferman, R. et al. Improving prediction of secondary structure, local backbone angles, and solvent accessible surface area of proteins by iterative deep learning. Sci. Rep. 5, 11476 (2015) 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.
Payandeh, J., Scheuer, T., Zheng, N. & Catterall, W. A. The crystal structure of a voltage-gated sodium channel. Nature 475, 353-358 (2011).
Shen, H. et al. Structure of a eukaryotic voltage-gated sodium channel at near-atomic resolution. Science 355, eaal4326 (2017), 19 pages.
Nakamura, K. et al. Clinical spectrum of SCN2A mutations expand-ing to Ohtahara syndrome. Neurology 81, 992-998 (2013).
Ioannidis, Nilah M., et al., "REVEL—An Ensemble Method for Predicting the Pathogenicity of Rare Missense Variants", Oct. 5, 2016, 9 pages.
Quang Daniel, et. al., "DANN—a deep learning approach for annotating the pathogenicity of genetic variants", Oct. 22, 2014, 3 pages.
Sundaram, et. al., "Predicting the clinical impact of human mutation with deep neural networks", Aug. 2018, 15pgs.
Xiong, et. al., "The human splicing code reveals new insights into the genetic determinants of disease", Jan. 9, 2015, 20pgs.
Yue, et. al., "Deep Learning for Genomics—A Concise Overview from internet", May 8, 2018, 40pgs.
Yuen, et. al., "Genome wide characteristics of de novo mutations in autism", Jun. 1, 2016, 10pgs.
Libbrecht, et. al., "Machine learning in genetics and genomics", Jan. 2, 2017, 30pgs.
Min, et. al., "Deep Learning in Bioinformatics", Jul. 25, 2016, 19 pgs.
Torng, Wen, et al., "3D deep convolutional neural networks for amino acid environment similarity analysis", 2017, 23pages.
Chen, Kathleen M., et. al., "Selene—a PyTorch based deep learning library for sequence level data", Oct. 10, 2018, 15pages.
Grob, C., et. al., "Predicting variant deleteriousness in non human species Applying the CADD approach in mouse", 2018, 11 pages.

Li, et. al., "FoldingZero—Protein Folding from Scratch in Hydro-phobic Polar Model", Dec. 3, 2018, 10 pages.
Rentzsch, et. al.,_"CADD—predicting the deleteriousness of vari-ants throughout the human genome", Oct. 11, 2018, 9 pages.
Zou, etal, "A primer on deep learning in genomics", Nov. 26, 2018, 7pages.
Alberts, Bruce, et al., "Molecular biology of the cell", Sixth Edition, 2015, 3 pages.
PCT/US2018/055840—International Search Report and Written Opinion dated Jan. 25, 2019, 18 pages.
Wei etal_The Role of Balanced Training and Testing Data Sets for Binary Classifiers in Bioinformatics dated Jul. 9, 2013 12 pages.
PCT/US2018/055878—International Search Report and Written Opinion dated Jan. 22, 2019, 20 pages.
PCT/US2018/055881—International Search Report and Written Opinion dated Jan. 25, 2019, 17 pages.
Duggirala, Ravindranath, et.al., "Genome Mapping and Genomics in Human and Non Human Primate", 2015, 306pgs.
Brookes, Anthony J., "The essence of SNPs", 1999, pp. 177-186.
UniProtKB P04217 A1BG Human [retrieved on Mar. 13, 2019 from (www.uniprot.org/uniprot/P04217), 12pages.
Bahar, Protein Actions Principles and Modeling, Chapter 7, 2017 pp. 165-166.
Dunbrack, Roland L., Re Question about your Paper titled "The Role of Balanced Training and Testing Data Sets for Binary Classifiers in Bioinformatics", Message to Sikander Mohammed Khan, Feb. 3, 2019, E-mailm, 3pgs.
DbSNP rs2241788 [Retrieved on Mar. 13, 2019], Retrieved from the Internet<www.ncbi.nlm.nih.gov/snp/rs2241788>, 5 pages.
Wei, et. al., "Prediction of phenotypes of missense mutations in human proteins from biological assemblies", Feb. 2013, 28 pages.
Zhang, Jun, and Bin Liu. "PSFM-DBT—identifying DNA-binding proteins by combing position specific frequency matrix and distance-bigram transformation. "International journal of molecular sciences 18.9 (2017) 1856.
Gao, Tingting, et al. "Identifying translation initiation sites in prokaryotes using support vector machine." Journal of theoretical biology 262.4 (2010) 644-649. (Year 2010).
Bi, Yingtao, et al. "Tree-based position weight matrix approach to model transcription factor binding site profiles." PloS one6.9 (2011) e24210.
Korhonen, Janne H., et al. "Fast motif matching revisited—high-order PWMs, SNPs and indels." Bioinformatics 33.4 (2016) 514-521.
Wong, Sebastien C., et al. "Understanding data augmentation for classification—when to warp?." 2016 international conference on digital image computing—techniques and applications (DICTA). IEEE, 2016.
Chang, Chia-Yun, et al. "Oversampling to overcome overfitting—exploring the relationship between data set composition, molecular descriptors, and predictive modeling methods." Journal of chemical information and modeling 53.4 (2013) 958-971.
Li, Gangmin, and Bei Yao. "Classification of Genetic Mutations for Cancer Treatment with Machine Learning Approaches." Interna-tional Journal of Design, Analysis and Tools for Integrated Circuits and Systems 7.1 (2018) pp. 63-67.
Martin-Navarro, Antonio, et al. "Machine learning classifier for identification of damaging missense mutations exclusive to human mitochondrial DNA-encoded polypeptides." BMC bioinformatics 18.1 (2017) p. 158.
Krizhevsky, Alex, et al., ImageNet Classification with Deep Con-volutional Neural Networks, 2012, 9 Pages.
Geeks for Geeks, "Underfitting and Overfilling in Machine Learn-ing", [retrieved on Aug. 26, 2019]. Retrieved from the Internet <www.geeksforgeeks.org/underfitting-and-overfitting-in-machine-learning/>, 2 pages.
Despois, Julien, "Memorizing is not learning!—6 tricks to prevent overfitting in machine learning", Mar. 20, 2018, 17 pages.
Bhande, Anup What is underfitting and overfitting in machine learning and how to deal with it, Mar. 11, 2018, 10pages.
PCT/US2019031621—International Search Report and Written Opin-ion dated Aug. 7, 2019, 17 pages.

(56) References Cited

OTHER PUBLICATIONS

Carter et al., "Cancer-specific high-throughput annotation of somatic mutations—computational prediction of driver missense mutations," Cancer research 69, No. 16 (2009) pp. 6660-6667.

PCT/US2021/018258—Second Written Opinion, dated Jan. 25, 2022, 11 pages.

PCT/US2021/018910—International Search Report and Written Opinion, dated Aug. 25, 2021, 24 pages.

Puckelwartz et al., Supercomputing for the parallelization of whole genome analysis, Bioinformatics, dated Feb. 12, 2014, pp. 1508-1513, 6 pages.

Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.

PCT/US2021/018910—Article 34 Amendment, filed Dec. 19, 2021, 9 pages.

PCT/US2021/018910—Second Written Opinion, dated Feb. 21, 2022, 17 pages.

PCT/US2021/018422—Article 34 Amendment, dated Dec. 20, 2021, 7 pages.

PCT/US/2021/018427—Second Written Opinion, dated Feb. 4, 2022, 9 pages.

PCT/US/2021/018427—Article 34 Amendment, filed Dec. 19, 2021, 7 pages.

PCT/US2021/018913—Second Written Opinion, dated Feb. 4, 2022, 8 pages.

Ye et al., BlindCall: ultra-fast base-calling of high-throughput sequencing data by blind deconvolution, Bioinformatics, vol. 30, No. 9, dated Jan. 9, 2014, pp. 1214-1219, 6 pages.

Wang et al., Achieving Accurate and Fast Base-calling by a Block model of the Illumina Sequencing Data, Science Direct, vol. 48, No. 28, dated Jan. 1, 2015, pp. 1462-1465, 4 pages.

PCT/US2021/018913—Article 34 Amendment, filed Dec. 19, 2021, 18 pages.

PCT/US2021/018915—Second Written Opinion, dated Feb. 4, 2022, 9 pages.

PCT/US2021/018915—Article 34 Amendment, filed Dec. 19, 2021, 7 pages.

PCT/US2021/018917—Second Written Opinion, dated Feb. 4, 2022, 7 pages.

PCT/US2021/018917—Article 34 Amendment, filed Dec. 19, 2021, 6 pages.

U.S. Appl. No. 17/468,411—Office Action, dated Feb. 24, 2022, 36 pages.

Gao et al., Deep Learning in Protein Structural Modeling and Design, Patterns—CelPress, dated Dec. 11, 2020, 23 pages.

Pejaver et al., Inferring the molecular and phenotypic impact of amino acid variants with MutPred2—with Supplementary Information, Nature Communications, dated 2020, 59 pages.

Pakhrin et al., Deep learning based advances in protein structure prediction, International Journal of Molecular sciences, published May 24, 2021, 30 pages.

Wang et al. Predicting the impacts of mutations on protein-ligand binding affinity based on molecular dynamics simulations and machine learning methods, Computational and Structural Biotechnology Journal 18, dated Feb. 20, 2022, pp. 439-454, 16 pages.

Iqbal et al., Comprehensive characterization of amino acid positions in protein structures reveals molecular effects of missense variants, and supplemental information, PNAS, vol. 117, No. 45, dated Nov. 10, 2020, 35 pages.

Forghani et al., Convolutional Neural Network Based Approach to In Silica Non-Anticipating Prediction of Antigenic Distance for Influenza Virus, Viruses, published Sep. 12, 2020, vol. 12, 20 pages.

Jing et al., Learning from protein structure with geometric vector perceptrons, Arxiv: 2009: 01411v2, dated Dec. 31, 2020, 18 pages.

Anonymous: "NovaSeq 6000—Sequencing System Guide", Feb. 1, 2019 (Feb. 1, 2019), XP055656862, Retrieved from the Internet: URL:https://support.illumina.com/content/dam/illumina-support/documents/documentation/system_documentation/novaseq/novaseq-6000-system-guide-1000000019358-11.pdf [retrieved on Jan. 10, 2020].

Illumina, MiSeq® Reporter Software Guide, Illumina Proprietary, Document #15042295 V05, 52 pages, Jan. 2017.

* cited by examiner

FIG. 14

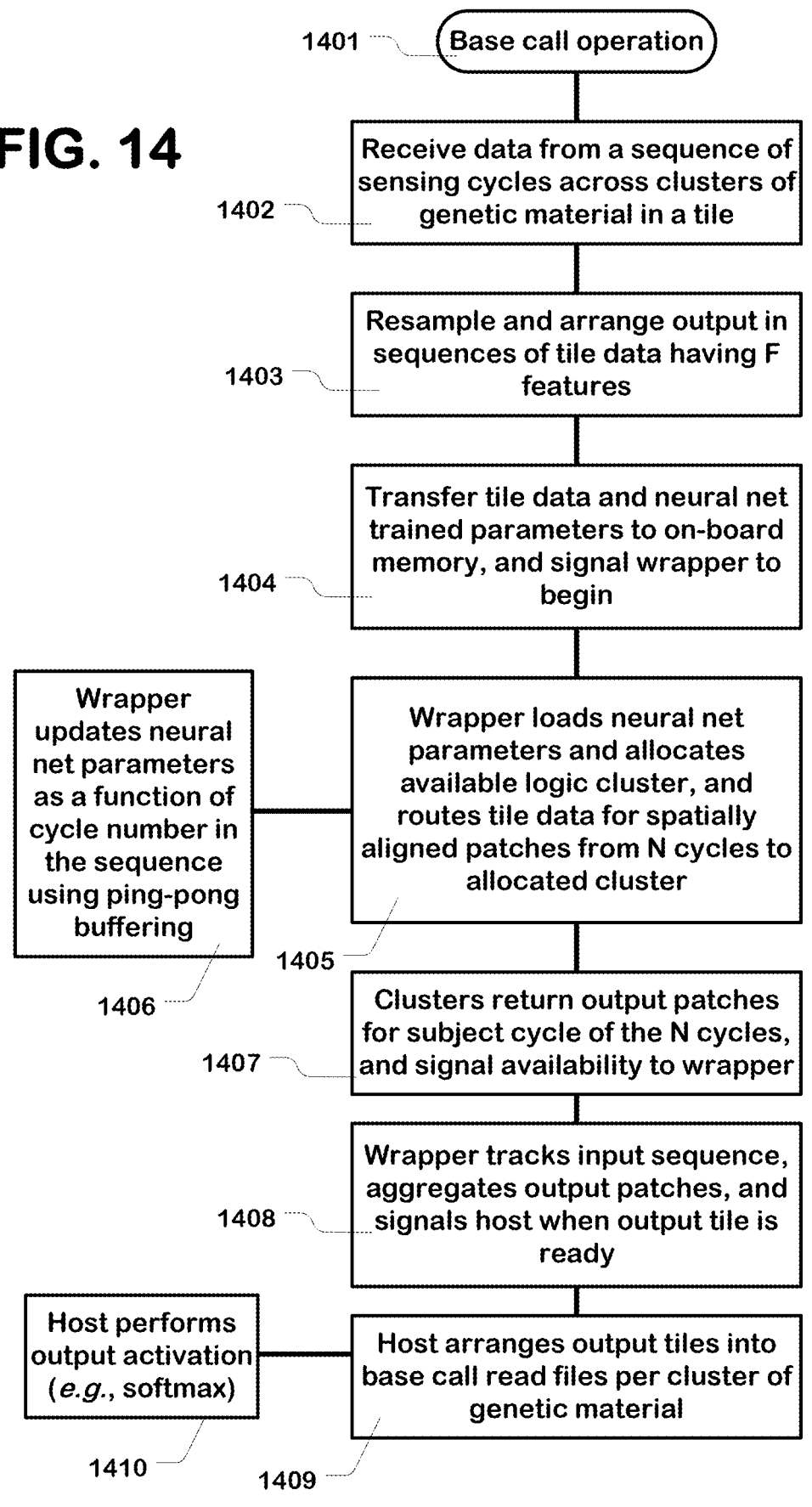

1401 — Base call operation

1402 — Receive data from a sequence of sensing cycles across clusters of genetic material in a tile 1403 — Resample and arrange output in sequences of tile data having F features 1404 — Transfer tile data and neural net trained parameters to on-board memory, and signal wrapper to begin 1406 — Wrapper updates neural net parameters as a function of cycle number in the sequence using ping-pong buffering 1405 — Wrapper loads neural net parameters and allocates available logic cluster, and routes tile data for spatially aligned patches from N cycles to allocated cluster 1407 — Clusters return output patches for subject cycle of the N cycles, and signal availability to wrapper 1408 — Wrapper tracks input sequence, aggregates output patches, and signals host when output tile is ready 1410 — Host performs output activation (e.g., softmax)

1409 — Host arranges output tiles into base call read files per cluster of genetic material

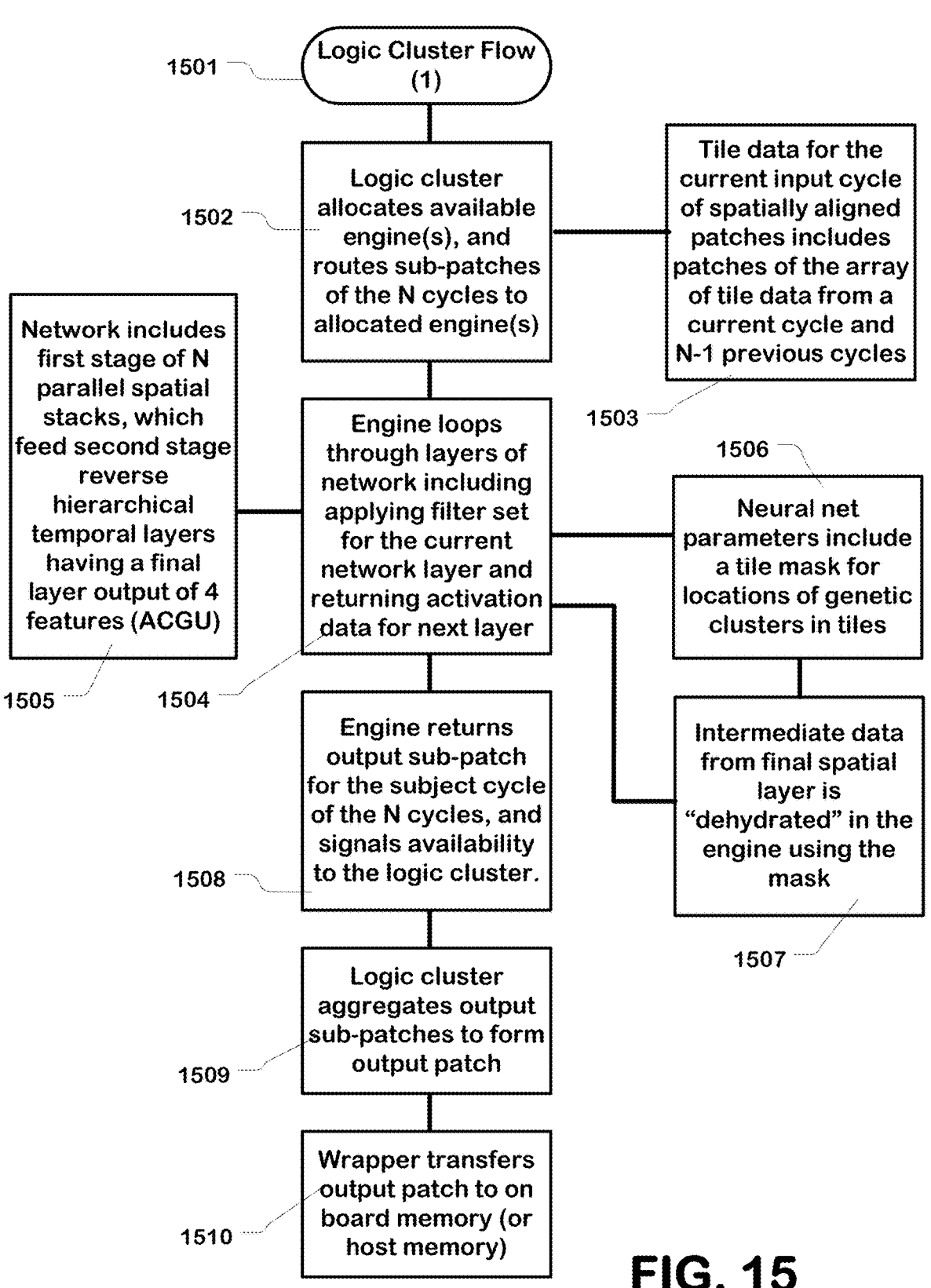

1501 — Logic Cluster Flow (1)

1502 — Logic cluster allocates available engine(s), and routes sub-patches of the N cycles to allocated engine(s)

1503 — Tile data for the current input cycle of spatially aligned patches includes patches of the array of tile data from a current cycle and N-1 previous cycles 1505 — Network includes first stage of N parallel spatial stacks, which feed second stage reverse hierarchical temporal layers having a final layer output of 4 features (ACGU)

1504 — Engine loops through layers of network including applying filter set for the current network layer and returning activation data for next layer 1506 — Neural net parameters include a tile mask for locations of genetic clusters in tiles 1507 — Intermediate data from final spatial layer is "dehydrated" in the engine using the mask 1508 — Engine returns output sub-patch for the subject cycle of the N cycles, and signals availability to the logic cluster.

1509 — Logic cluster aggregates output sub-patches to form output patch

1510 — Wrapper transfers output patch to on board memory (or host memory)

FIG. 15

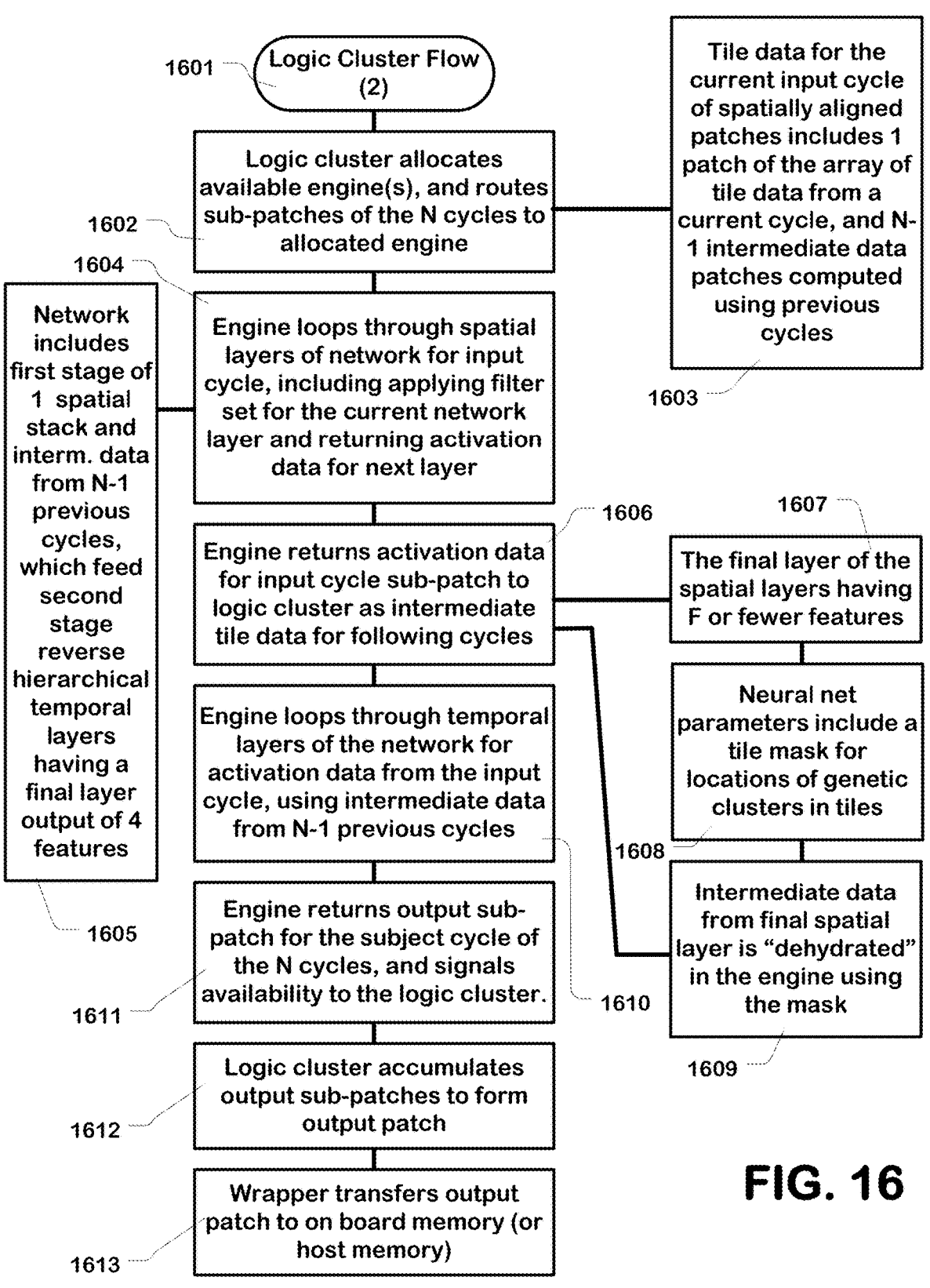

1601 — Logic Cluster Flow (2)

1602 — Logic cluster allocates available engine(s), and routes sub-patches of the N cycles to allocated engine 1603 — Tile data for the current input cycle of spatially aligned patches includes 1 patch of the array of tile data from a current cycle, and N-1 intermediate data patches computed using previous cycles 1604 — Engine loops through spatial layers of network for input cycle, including applying filter set for the current network layer and returning activation data for next layer 1605 — Network includes first stage of 1 spatial stack and interm. data from N-1 previous cycles, which feed second stage reverse hierarchical temporal layers having a final layer output of 4 features 1606 — Engine returns activation data for input cycle sub-patch to logic cluster as intermediate tile data for following cycles 1607 — The final layer of the spatial layers having F or fewer features 1608 — Neural net parameters include a tile mask for locations of genetic clusters in tiles 1610 — Engine loops through temporal layers of the network for activation data from the input cycle, using intermediate data from N-1 previous cycles 1609 — Intermediate data from final spatial layer is "dehydrated" in the engine using the mask 1611 — Engine returns output sub-patch for the subject cycle of the N cycles, and signals availability to the logic cluster.

1612 — Logic cluster accumulates output sub-patches to form output patch

1613 — Wrapper transfers output patch to on board memory (or host memory)

FIG. 16

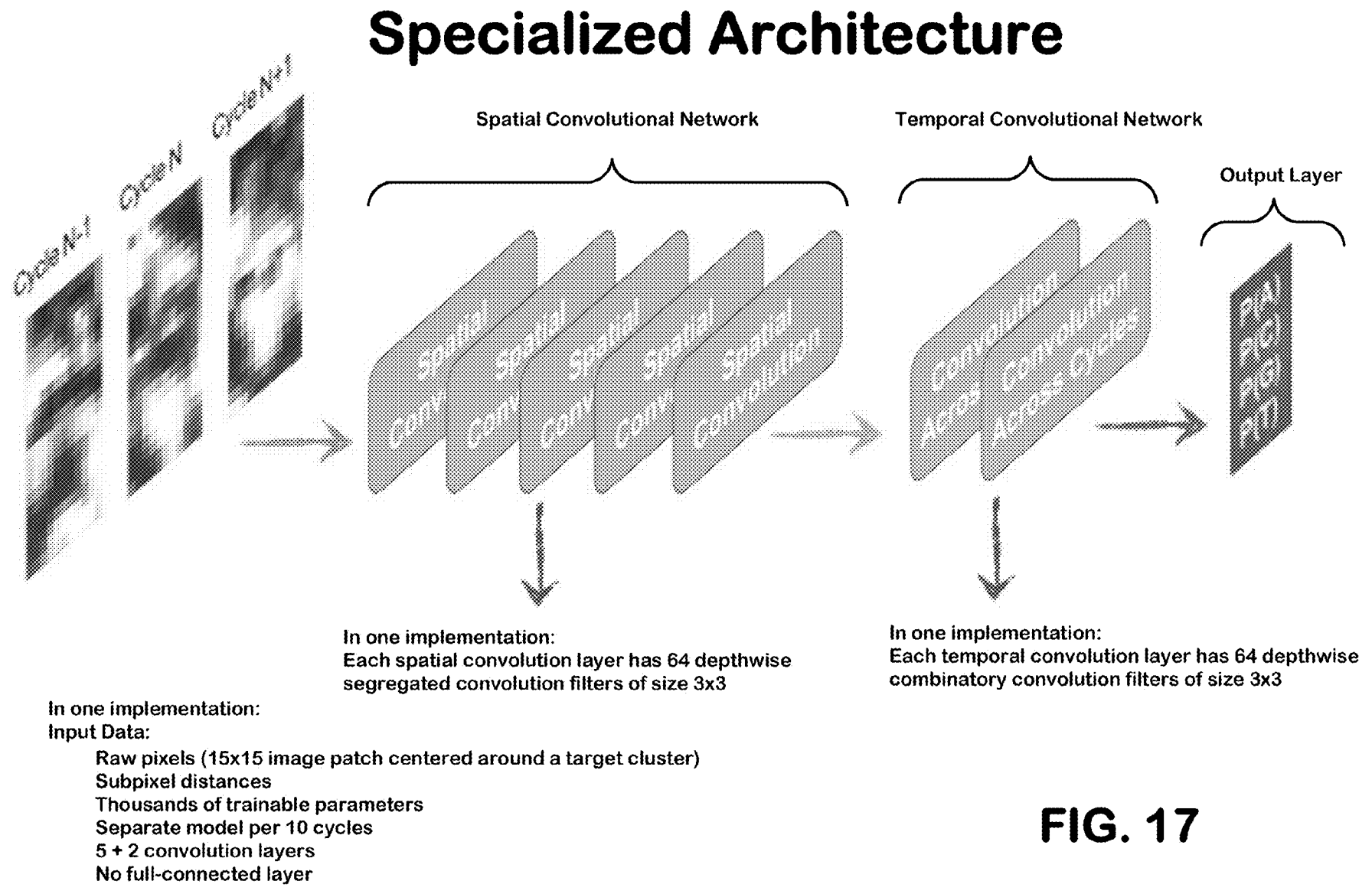

Specialized Architecture

Output Layer

Temporal Convolutional Network

Spatial Convolutional Network

In one implementation:
Each temporal convolution layer has 64 depthwise combinatory convolution filters of size 3x3

In one implementation:
Each spatial convolution layer has 64 depthwise segregated convolution filters of size 3x3

In one implementation:
Input Data:
Raw pixels (15x15 image patch centered around a target cluster)
Subpixel distances
Thousands of trainable parameters
Separate model per 10 cycles
5 + 2 convolution layers
No full-connected layer

FIG. 17

HARDWARE EXECUTION AND ACCELERATION OF ARTIFICIAL INTELLIGENCE-BASED BASE CALLER

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

PRIORITY APPLICATION

This application claims priority to and benefit of U.S. Provisional Patent Application No. 62/979,412, titled "MULTI-CYCLE CLUSTER BASED REAL TIME ANALYSIS SYSTEM," filed 20 Feb. 2020. The priority application is hereby incorporated by reference for all purposes as if fully set forth herein.

This application claims priority to and benefit of U.S. Provisional Patent Application No. 62/979,385, titled "KNOWLEDGE DISTILLATION-BASED COMPRESSION OF ARTIFICIAL INTELLIGENCE-BASED BASE CALLER," filed 20 Feb. 2020. The priority application is hereby incorporated by reference for all purposes as if fully set forth herein.

This application claims priority to and benefit of U.S. Provisional Patent Application No. 63/072,032, titled "DETECTING AND FILTERING CLUSTERS BASED ON ARTIFICIAL INTELLIGENCE-PREDICTED BASE CALLS," filed 28 Aug. 2020. The priority application is hereby incorporated by reference for all purposes as if fully set forth herein.

This application claims priority to and benefit of U.S. Provisional Patent Application No. 62/979,411, titled "DATA COMPRESSION FOR ARTIFICIAL INTELLIGENCE-BASED BASE CALLING," filed 20 Feb. 2020. The priority application is hereby incorporated by reference for all purposes as if fully set forth herein.

This application claims priority to and benefit of U.S. Provisional Patent Application No. 62/979,399, titled "SQUEEZING LAYER FOR ARTIFICIAL INTELLIGENCE-BASED BASE CALLING," filed 20 Feb. 2020. The priority application is hereby incorporated by reference for all purposes as if fully set forth herein.

INCORPORATIONS

The following are incorporated by reference as if fully set forth herein:

U.S. Provisional Patent Application No. 62/979,384, titled "ARTIFICIAL INTELLIGENCE-BASED BASE CALLING OF INDEX SEQUENCES," filed 20 Feb. 2020;

U.S. Provisional Patent Application No. 62/979,414, titled "ARTIFICIAL INTELLIGENCE-BASED MANY-TO-MANY BASE CALLING," filed 20 Feb. 2020;

U.S. Nonprovisional patent application Ser. No. 16/825, 987, titled "TRAINING DATA GENERATION FOR ARTIFICIAL INTELLIGENCE-BASED SEQUENCING," filed 20 Mar. 2020;

U.S. Nonprovisional patent application Ser. No. 16/825, 991 titled "ARTIFICIAL INTELLIGENCE-BASED GENERATION OF SEQUENCING METADATA," filed 20 Mar. 2020;

U.S. Nonprovisional patent application Ser. No. 16/826, 126, titled "ARTIFICIAL INTELLIGENCE-BASED BASE CALLING," filed 20 Mar. 2020;

U.S. Nonprovisional patent application Ser. No. 16/826, 134, titled "ARTIFICIAL INTELLIGENCE-BASED QUALITY SCORING," filed 20 Mar. 2020; and U.S. Nonprovisional patent application Ser. No. 16/826, 168, titled "ARTIFICIAL INTELLIGENCE-BASED SEQUENCING," filed 21 Mar. 2020.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions. A hallmark of convolutional neural networks is the use of convolution filters.

Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, an opportunity arises to use a principled deep learning-based framework for template generation and base calling.

In the era of high-throughput technology, amassing the highest yield of interpretable data at the lowest cost per effort remains a significant challenge. Cluster-based methods of nucleic acid sequencing, such as those that utilize bridge amplification for cluster formation, have made a valuable contribution toward the goal of increasing the throughput of nucleic acid sequencing. These cluster-based methods rely on sequencing a dense population of nucleic acids immobilized on a solid support, and typically involve the use of image analysis software to deconvolve optical signals generated in the course of simultaneously sequencing multiple clusters situated at distinct locations on a solid support.

However, such solid-phase nucleic acid cluster-based sequencing technologies still face considerable obstacles that limit the amount of throughput that can be achieved. For example, in cluster-based sequencing methods, determining the nucleic acid sequences of two or more clusters that are physically too close to one another to be resolved spatially, or that in fact physically overlap on the solid support, can pose an obstacle. For example, current image analysis software can require valuable time and computational resources for determining from which of two overlapping clusters an optical signal has emanated. As a consequence, compromises are inevitable for a variety of detection platforms with respect to the quantity and/or quality of nucleic acid sequence information that can be obtained.

High density nucleic acid cluster-based genomics methods extend to other areas of genome analysis as well. For example, nucleic acid cluster-based genomics can be used in sequencing applications, diagnostics and screening, gene expression analysis, epigenetic analysis, genetic analysis of polymorphisms, and the like. Each of these nucleic acid cluster-based genomics technologies, too, is limited when there is an inability to resolve data generated from closely proximate or spatially overlapping nucleic acid clusters.

Clearly there remains a need for increasing the quality and quantity of nucleic acid sequencing data that can be obtained rapidly and cost-effectively for a wide variety of uses, including for genomics (e.g., for genome characterization of any and all animal, plant, microbial or other biological species or populations), pharmacogenomics, transcriptomics, diagnostics, prognostics, biomedical risk assessment, clinical and research genetics, personalized medicine, drug efficacy and drug interactions assessments, veterinary medicine, agriculture, evolutionary and biodiversity studies, aquaculture, forestry, oceanography, ecological and environmental management, and other purposes.

The technology disclosed provides neural network-based methods and systems that address these and similar needs, including increasing the level of throughput in high-throughput nucleic acid sequencing technologies, and offers other related advantages.

The use of deep neural networks and other complex machine learning algorithms can require substantial resources in terms of hardware computing and storage capacity. Also, is desirable to minimize the time required to execute sensing and analysis operations so that the computation. It is desirable to achieve computation times that make results available to customers, effectively in real time.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 14 is a host runtime flowchart illustrating a base calling operation utilizing resources as described herein, like that of FIG. 1.

FIG. 15 is a logic cluster execution flowchart illustrating the data flow configuration for a logic cluster as described herein.

FIG. 16 is an alternative logic cluster execution flowchart illustrating the data flow configuration for a logic cluster as described herein.

FIG. 17 illustrates one implementation of a specialized architecture of the neural network-based base caller that is used to segregate processing of data for different sequencing cycles.

DETAILED DESCRIPTION

Figure 1:
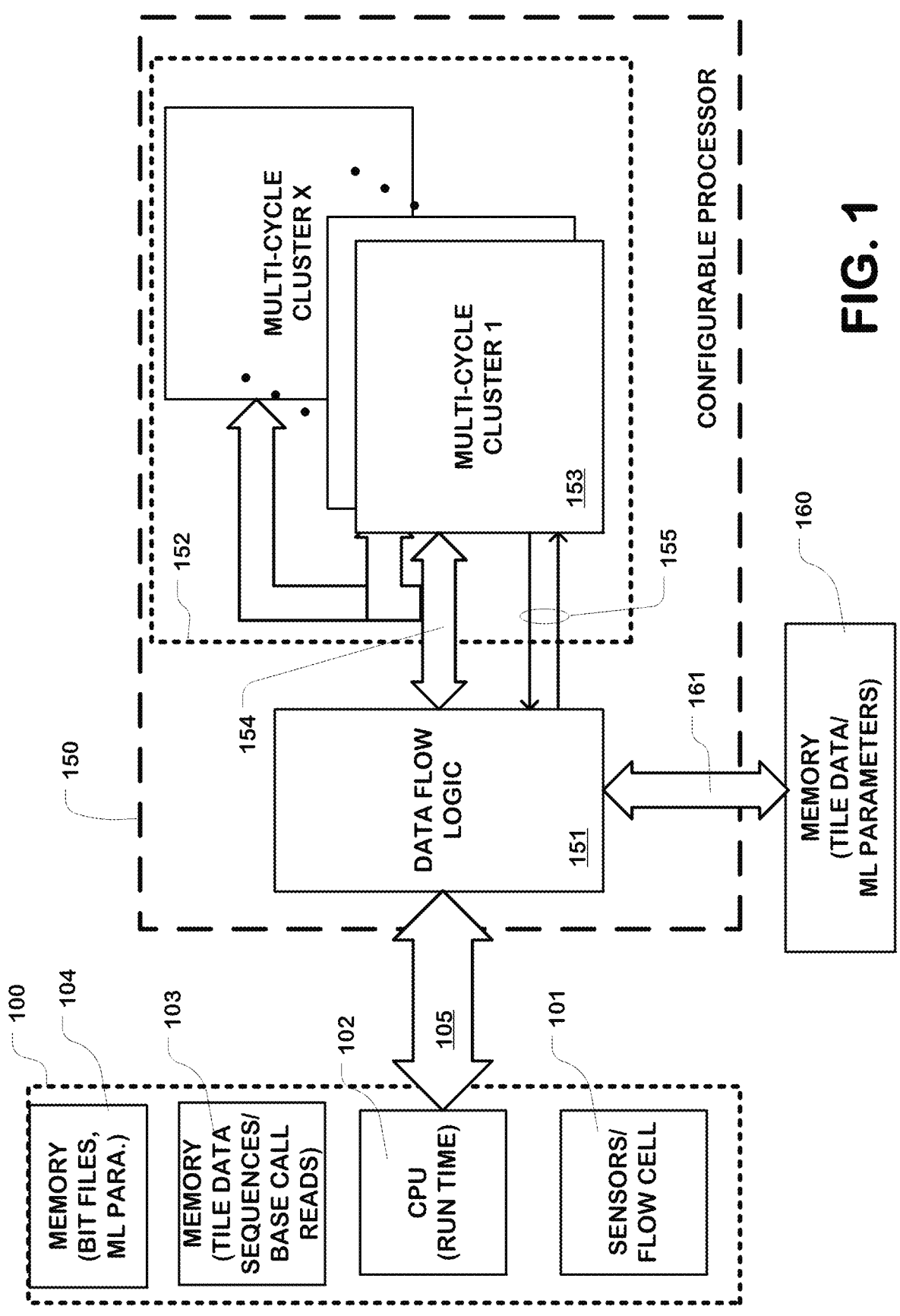
FIG. 1 is a simplified diagram of a base calling computation system that comprises a configurable processor.

A method implementation of the technology disclosed includes storing tile data in memory including sensor data for a tile from sensing cycles of a base calling operation; executing runs of a neural network using trained parameters to produce classification data for sensing cycles, a run of the neural network operating on a sequence of N arrays of tile data from respective sensing cycles of N sensing cycles, including a subject cycle, to produce the classification data for the subject cycle; and moving tile data and the trained parameters from memory to the neural network for runs of the neural network using input units including data for spatially aligned patches of the N arrays from respective sensing cycles of N sensing cycles.

Another method implementation of the technology disclosures includes storing tile data in memory including arrays of sensor data for tiles from sensing cycles of a base calling operation; and executing a neural network over the tile data using a plurality of execution clusters. Executing the neural network includes in this implementation providing input units of tile data to available execution clusters in the plurality of execution clusters, the input units including a number N of spatially aligned patches of arrays of tile data from respective sensing cycles, including a subject sensing cycle, and causing the execution clusters to apply the N spatially aligned patches to the neural network to produce output patches of classification data for the spatially aligned patch of the subject sensing cycle, where N is greater than 1. The output patches can include only data from pixels that correspond with clusters generating base call data, and so may have sizes and dimensions different from the input patches.

Also, the methods described herein can include image resampling in systems in which the input image orientations jitter around due to the camera movement/vibration. To compensate, the image data is resampled being provided as input into the network to ensure that there is a common basis across the images, to simplify the neural network's job. Resampling involves for example, applying an affine transform (translation, shear, rotation) to the image data. This resampling can be executed in software executed by a host processor. In other implementations, resampling can be executed in a configured gate array or other hardware.

The bit files, model parameters and runtime program described herein can be implemented separately or in any combination using a non-transitory computer readable storage medium (CRM) or media storing instructions, including configuration data and model parameters, executable by a processor to perform the methods described herein. Each of the features discussed in this particular implementation section for the method implementation apply equally to the CRM implementation. As indicated above, all the method features are not repeated here and should be considered repeated by reference.

Yet another implementation may include a system including memory and one or more processors operable to execute instructions, stored in the memory, to perform the method described above.

A system implementation of the technology disclosed includes memory accessible by the run time runtime program storing tile data including sensor data for a tile from sensing cycles of a base calling operation; a neural network processor having access to the memory, the neural network processor configured to execute runs of a neural network using trained parameters to produce classification data for sensing cycles, a run of the neural network operating on a sequence of N arrays of tile data from respective sensing cycles of N sensing cycles, including a subject cycle, to produce the classification data for the subject cycle; and data flow logic to move tile data and the trained parameters from the memory to the neural network processor for runs of the neural network using input units including data for spatially aligned patches of the N arrays from respective sensing cycles of N sensing cycles. The neural network processor and the data flow logic can be implemented using a configurable or a reconfigurable processor, such as an FPGA, or CGRA.

Another system implementation of the technology disclosed includes a host processor; memory accessible by the host processor storing tile data including arrays of sensor data for tiles from sensing cycles of a base calling operation; and a neural network processor having access to the memory, the neural network processor can include a plurality of execution clusters, the execution logic clusters in the plurality of execution clusters configured to execute a neural network; and data flow logic having access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1. The neural network processor and the data flow logic can be implemented using a configurable or a reconfigurable processor, such as an FPGA, or CGRA.

Each of the features discussed in this particular implementation section for the method implementation apply equally to the system implementation. As indicated above, all the method features are not repeated here and should be considered repeated by reference.

The technology disclosed, e.g., the disclosed base callers (e.g., FIG. 4 and FIG. 10) can be implemented on processors like Central Processing Units (CPUs), Graphics Processing Units (GPUs), Field Programmable Gate Arrays (FPGAs), Coarse-Grained Reconfigurable Architectures (CGRAs), Application-Specific Integrated Circuits (ASICs), Application Specific Instruction-set Processor (ASIP), and Digital Signal Processors (DSPs).

FIG. 1 is a simplified block diagram of the system for analysis of sensor data from a sequencing system, such as base call sensor outputs. (See also, FIG. 21). In the example of FIG. 1, the system includes a sequencing machine 100 and a configurable processor 150. The configurable processor 150 can execute a neural network-based base caller (e.g., 2158 of FIG. 21) in coordination with a runtime program executed by the central processing unit CPU 102. The sequencing machine 100 comprises base call sensors and flow cells 101. The flow cells can comprise one or more tiles in which clusters of genetic material are exposed to a sequence of analyte flows used to cause reactions in the clusters to identify the bases in the genetic material. The sensors sense the reactions for each cycle of the sequence in each tile of the flow cell to provide tile data. Examples of this technology are described in more detail below. Genetic sequencing is a data intensive operation, which translates base call sensor data into sequences of base calls for each cluster of genetic material sensed in during a base call operation.

The system in this example includes a central processing unit 102 which executes a runtime program to coordinate the base call operations, memory 103 to store sequences of arrays of tile data, base call reads produced by the base calling operation, and other information used in the base call operations. Also, in this illustration the system includes memory 104 to store a configuration file (or files), such as FPGA bit files, and model parameters for the neural network used to configure and reconfigure the configurable processor 150 and execute the neural network. The machine 100 can include a program for configuring a configurable processor and in some embodiments a reconfigurable processor to execute the neural network.

The sequencing machine 100 is coupled by a bus 105 to the configurable processor 150. The bus 105 can be implemented using a high throughput technology, such as in one example bus technology compatible with the PCIe standards (Peripheral Component Interconnect Express) currently maintained and developed by the PCI-SIG (PCI Special Interest Group). Also, in this example, a memory 160 is coupled to the configurable processor 150 by bus 161. The memory 160 can be on-board memory, disposed on a circuit board with the configurable processor 150. The memory 160 is used for high speed access by the configurable processor 150 of working data used in the base call operation. The bus 161 can also be implemented using a high throughput technology, such as bus technology compatible with the PCIe standards.

Configurable processors, including field programmable gate arrays FPGAS, coarse grained reconfigurable arrays CGRAs, and other configurable and reconfigurable devices, can be configured to implement a variety of functions more efficiently or faster than might be achieved using a general purpose processor executing a computer program. Configuration of configurable processors involves compiling a functional description to produce a configuration file, referred to sometimes as a bitstream or bit file, and distributing the configuration file to the configurable elements on the processor.

The configuration file defines the logic functions to be executed by the configurable processor, by configuring the circuit to set data flow patterns, use of distributed memory and other on-chip memory resources, lookup table contents, operations of configurable logic blocks and configurable execution units like multiply-and-accumulate units, configurable interconnects and other elements of the configurable array. A configurable processor is reconfigurable if the configuration file may be changed in the field, by changing the loaded configuration file. For example, the configuration file may be stored in volatile SRAM elements, in non-volatile read-write memory elements, and in combinations of the same, distributed among the array of configurable elements on the configurable or reconfigurable processor. A variety of commercially available configurable processors are suitable for use in a base calling operation as described herein. Examples include commercially available products such as Xilinx Alveo™ U200, Xilinx Alveo™ U250, Xilinx Alveo™ U280, Intel/Altera Stratix™ GX2800, Intel/Altera Stratix™ GX2800, and Intel Stratix™ GX10M. In some examples, a host CPU can be implemented on the same integrated circuit as the configurable processor.

Embodiments described herein implement the multi-cycle neural network using a configurable processor 150. The configuration file for a configurable processor can be implemented by specifying the logic functions to be executed using a high level description language HDL or a register transfer level RTL language specification. The specification can be compiled using the resources designed for the selected configurable processor to generate the configuration file. The same or similar specification can be compiled for the purposes of generating a design for an application-specific integrated circuit which may not be a configurable processor.

Alternatives for the configurable processor, in all embodiments described herein, therefore include a configured processor comprising an application specific ASIC or special purpose integrated circuit or set of integrated circuits, or a system-on-a-chip SOC device, configured to execute a neural network based base call operation as described herein.

In general, configurable processors and configured processors described herein, as configured to execute runs of a neural network, are referred to herein as neural network processors.

The configurable processor 150 is configured in this example by a configuration file loaded using a program executed by the CPU 102, or by other sources, which configures the array of configurable elements on the configurable processor 150 to execute the base call function. In this example, the configuration includes data flow logic 151 which is coupled to the buses 105 and 161 and executes functions for distributing data and control parameters among the elements used in the base call operation.

Also, the configurable processor 150 is configured with base call execution logic 152 to execute a multi-cycle neural network. The logic 152 comprises a plurality of multi-cycle execution clusters (e.g., 153) which, in this example, includes multi-cycle cluster 1 through multi-cycle cluster X. The number of multi-cycle clusters can be selected according to a trade-off involving the desired throughput of the operation, and the available resources on the configurable processor.

The multi-cycle clusters are coupled to the data flow logic 151 by data flow paths 154 implemented using configurable interconnect and memory resources on the configurable processor. Also, the multi-cycle clusters are coupled to the data flow logic 151 by control paths 155 implemented using configurable interconnect and memory resources for example on the configurable processor, which provide control signals indicating available clusters, readiness to provide input units for execution of a run of the neural network to the available clusters, readiness to provide trained parameters for the neural network, readiness to provide output patches of base call classification data, and other control data used for execution of the neural network.

The configurable processor is configured to execute runs of a multi-cycle neural network using trained parameters to produce classification data for sensing cycles of the base flow operation. A run of the neural network is executed to produce classification data for a subject sensing cycle of the base call operation. A run of the neural network operates on a sequence including a number N of arrays of tile data from respective sensing cycles of N sensing cycles, where the N sensing cycles provide sensor data for different base call operations for one base position per operation in time sequence in the examples described herein. Optionally, some of the N sensing cycles can be out of sequence if the needed according to a particular neural network model being executed. The number N can be any number greater than one. In some examples described herein, sensing cycles of the N sensing cycles represent a set of sensing cycles for at least one sensing cycle preceding the subject sensing cycle and at least one sensing cycle following the subject cycle in time sequence. Examples are described herein in which the number N is an integer equal to or greater than five.

The data flow logic is configured to move tile data and at least some trained parameters of the model parameters from the memory 160 to the configurable processor for runs of the neural network, using input units for a given run including tile data for spatially aligned patches of the N arrays. The input units can be moved by direct memory access operations in one DMA operation, or in smaller units moved during available time slots in coordination with the execution of the neural network deployed.

Tile data for a sensing cycle as described herein can comprise an array of sensor data having one or more features. For example, the sensor data can comprise two images which are analyzed to identify one of four bases at a base position in a genetic sequence of DNA, RNA, or other genetic material. The tile data can also include metadata about the images and the sensors. For example, in embodiments of the base calling operation, the tile data can comprise information about alignment of the images with the clusters such as distance from center information indicating the distance of each pixel in the array of sensor data from the center of a cluster of genetic material on the tile.

During execution of the multi-cycle neural network as described below, tile data can also include data produced during execution of the multi-cycle neural network, referred to as intermediate data, which can be reused rather than recomputed during a run of the multi-cycle neural network. For example, during execution of the multi-cycle neural network, the data flow logic can write intermediate data to the memory 160 in place of the sensor data for a given patch of an array of tile data. Embodiments like this are described in more detail below.

As illustrated, a system is described for analysis of base call sensor output, comprising memory (e.g., 160) accessible by the runtime program storing tile data including sensor data for a tile from sensing cycles of a base calling operation. Also, the system includes a neural network processor, such as configurable processor 150 having access to the memory. The neural network processor is configured to execute runs of a neural network using trained parameters to produce classification data for sensing cycles. As described herein, a run of the neural network is operating on a sequence of N arrays of tile data from respective sensing cycles of N sensing cycles, including a subject cycle, to produce the classification data for the subject cycle. The data flow logic 151 is provided to move tile data and the trained parameters from the memory to the neural network processor for runs of the neural network using input units including data for spatially aligned patches of the N arrays from respective sensing cycles of N sensing cycles.

Also, a system is described in which the neural network processor has access to the memory, and includes a plurality of execution clusters, the execution logic clusters in the plurality of execution clusters configured to execute a neural network. The data flow logic has access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

Figure 2:
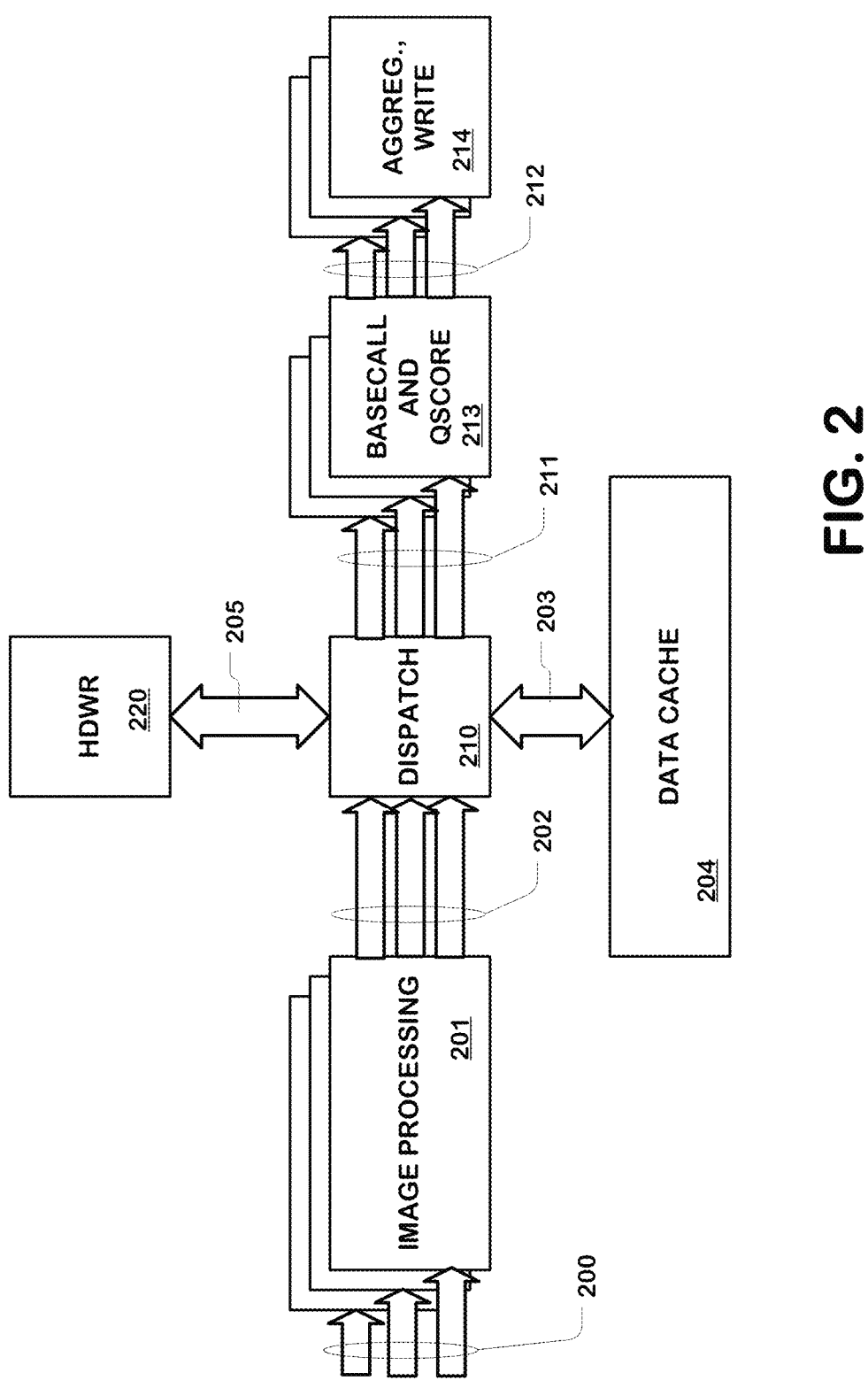
FIG. 2 is a simplified data flow diagram which can be executed by a system like that of FIG. 1.

FIG. 2 is a simplified diagram showing aspects of the base calling operation, including functions of a runtime program executed by a host processor. In this diagram, the output of image sensors from a flow cell are provided on lines 200 to image processing threads 201, which can perform processes on images such as resampling, alignment and arrangement in an array of sensor data for the individual tiles, and can be used by processes which calculate a tile cluster mask for each tile in the flow cell, which identifies pixels in the array of sensor data that correspond to clusters of genetic material on the corresponding tile of the flow cell. To compute a cluster mask, one example algorithm is based on a process to detect clusters which are unreliable in the early sequencing cycles using a metric derived from the softmax output, and then the data from those wells/clusters is discarded, and no output data is produced for those clusters. For example, a process can identify clusters with high reliability during the first N (e.g., 25) base-calls, and reject the others. Rejected clusters might be polyclonal or very weak intensity or obscured by fiducials. This procedure can be performed on the host CPU. In alternative implementations, this information would potentially be used to identify the necessary clusters of interest to be passed back to the CPU, thereby limiting the storage required for intermediate data (i.e., the 'dehydration' step described below could look at all pixels with wells, or it could be implemented more efficiently to only process pixels with wells/clusters that pass the filter).

The outputs of the image processing threads 201 are provided on lines 202 to a dispatch logic 210 in the CPU which routes the arrays of tile data to a data cache 204 on a high-speed bus 203, or on high-speed bus 205 to the multi-cluster neural network processor hardware 220, such as the configurable processor of FIG. 1, according to the state of the base calling operation. The hardware 220 returns classification data output by the neural network to the dispatch logic 210, which passes the information to the data cache 204, or on lines 211 to threads 213 that perform base call and quality score computations using the classification data, and can arrange the data in standard formats for base call reads. The outputs of the threads 213 that perform base calling and quality score computations are provided on lines 212 to threads 214 that aggregate the base call reads, perform other operations such as data compression, and write the resulting base call outputs to specified destinations for utilization by the customers.

In some embodiments, the host can include threads (not shown) that perform final processing of the output of the hardware 220 in support of the neural network. For example, the hardware 220 can provide outputs of classification data from a final layer of the multi-cluster neural network. The host processor can execute an output activation function, such as a softmax function, over the classification data to configure the data for use by the base call and quality score threads 213. Also, the host processor can execute input operations (not shown), such as resampling, batch normalization or other adjustments of the tile data prior to input to the hardware 220.

Figure 3:
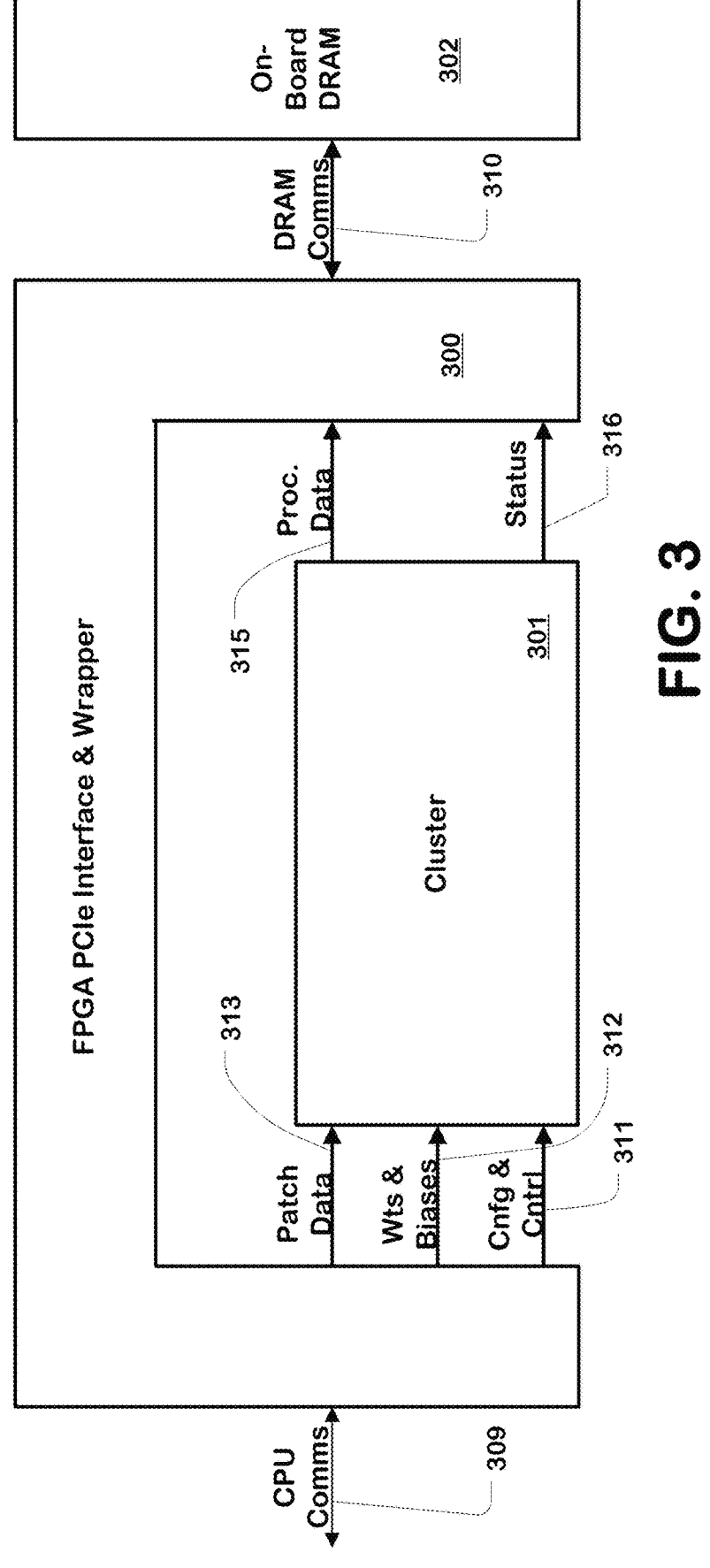
FIG. 3 illustrates a configuration architecture for components of a configurable or a reconfigurable array supporting base calling operations.

FIG. 3 is a simplified diagram of a configuration of a configurable processor such as that of FIG. 1. In FIG. 3, the configurable processor comprises in FPGA with a plurality of high speed PCIe interfaces. The FPGA is configured with a wrapper 300 which comprises the data flow logic described with reference to FIG. 1. The wrapper 300 manages the interface and coordination with a runtime program in the CPU across the CPU communication link 309 and manages communication with the on-board DRAM 302 (e.g. memory 160) via DRAM communication link 310. The data flow logic in the wrapper 300 provides patch data retrieved by traversing the arrays of tile data on the on-board DRAM 302 for the number N cycles to a cluster 301 and retrieves process data 315 from the cluster 301 for delivery back to the on-board DRAM 302. The wrapper 300 also manages transfer of data between the on-board DRAM 302 and host memory, for both the input arrays of tile data, and for the output patches of classification data. The wrapper transfers patch data on line 313 to the allocated cluster 301. The wrapper provides trained parameters, such as weights and biases on line 312 to the cluster 301 retrieved from the on-board DRAM 302. The wrapper provides configuration and control data on line 311 to the cluster 301 provided from, or generated in response to, the runtime program on the host via the CPU communication link 309. The cluster can also provide status signals on line 316 to the wrapper 300, which are used in cooperation with control signals from the host to manage traversal of the arrays of tile data to provide spatially aligned patch data, and to execute the multi-cycle neural network over the patch data using the resources of the cluster 301.

As mentioned above, there can be multiple clusters on a single configurable processor managed by the wrapper 300 configured for executing on corresponding ones of multiple patches of the tile data. Each cluster can be configured to provide classification data for base calls in a subject sensing cycle using the tile data of multiple sensing cycles described herein.

In examples of the system, model data, including kernel data like filter weights and biases can be sent from the host CPU to the configurable processor, so that the model can be updated as a function of cycle number. A base calling operation can comprise, for a representative example, on the order of hundreds of sensing cycles. Base calling operation can include paired end reads in some embodiments. For example, the model trained parameters may be updated once every 20 cycles (or other number of cycles), or according to update patterns implemented for particular systems and neural network models. In some embodiments including paired end reads in which a sequence for a given string in a genetic cluster on a tile includes a first part extending from a first end down (or up) the string, and a second part extending from a second end up (or down) the string, the trained parameters can be updated on the transition from the first part to the second part.

In some examples, image data for multiple cycles of sensing data for a tile can be sent from the CPU to the wrapper 300. The wrapper 300 can optionally do some pre-processing and transformation of the sensing data and write the information to the on-board DRAM 302. The input tile data for each sensing cycle can include arrays of sensor data including on the order of 4000×3000 pixels per sensing cycle per tile or more, with two features representing colors of two images of the tile, and one or two bytes per feature per pixel. For an embodiment in which the number N is three sensing cycles to be used in each run of the multi-cycle neural network, the array of tile data for each run of the multi-cycle neural network can consume on the order of hundreds of megabytes per tile. In some embodiments of the system, the tile data also includes an array of DFC data, stored once per tile, or other type of metadata about the sensor data and the tiles.

In operation, when a multi-cycle cluster is available, the wrapper allocates a patch to the cluster. The wrapper fetches a next patch of tile data in the traversal of the tile and sends it to the allocated cluster along with appropriate control and configuration information. The cluster can be configured with enough memory on the configurable processor to hold a patch of data including patches from multiple cycles in some systems, that is being worked on in place, and a patch of data that is to be worked on when the current patch of processing is finished using a ping-pong buffer technique or raster scanning technique in various embodiments.

When an allocated cluster completes its run of the neural network for the current patch and produces an output patch, it will signal the wrapper. The wrapper will read the output patch from the allocated cluster, or alternatively the allocated cluster will push the data out to the wrapper. Then the wrapper will assemble output patches for the processed tile in the DRAM 302. When the processing of the entire tile has been completed, and the output patches of data transferred to the DRAM, the wrapper sends the processed output array for the tile back to the host/CPU in a specified format. In some embodiments, the on-board DRAM 302 is managed by memory management logic in the wrapper 300. The runtime program can control the sequencing operations to complete analysis of all the arrays of tile data for all the cycles in the run in a continuous flow to provide real time analysis.

Figure 4:
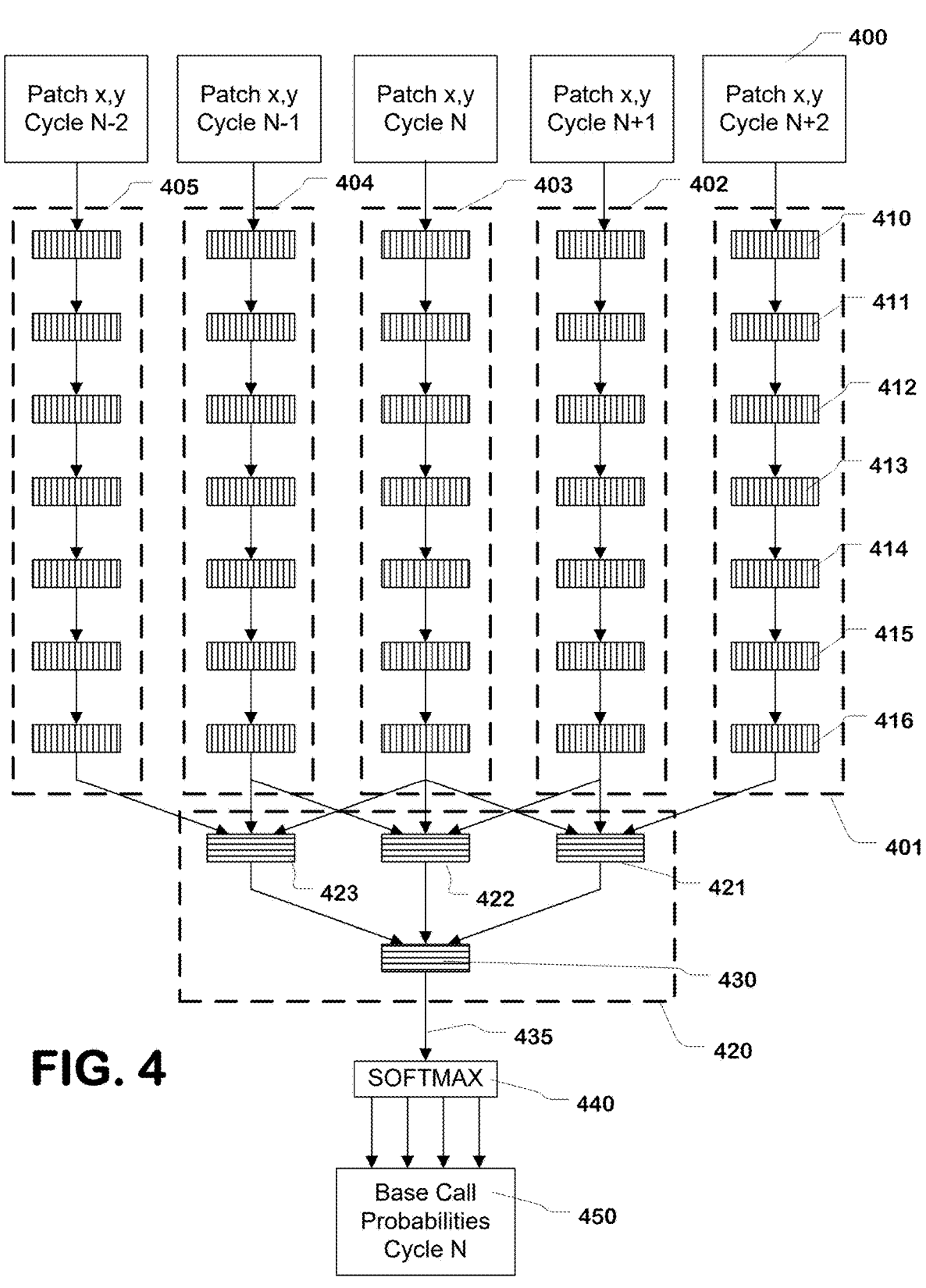
FIG. 4 is a diagram of a neural network architecture which can be executed using a configurable or a reconfigurable array configured as described herein.

FIG. 4 is a diagram of a multi-cycle neural network model which can be executed using the system described herein. The example shown in FIG. 4 can be referred to as a five-cycle input, one-cycle output neural network. The inputs to the multi-cycle neural network model include five spatially aligned patches (e.g., 400) from the tile data arrays of five sensing cycles of a given tile. Spatially aligned patches have the same aligned row and column dimensions (x,y) as other patches in the set, so that the information relates to the same clusters of genetic material on the tile in sequence cycles. In this example, a subject patch is a patch from the array of tile data for cycle N. The set of five spatially aligned patches includes a patch from cycle N–2 preceding the subject patch by two cycles, a patch from cycle N–1 preceding the subject patch by one cycle, a patch from cycle N+1 following the patch from the subject cycle by one cycle, and a patch from cycle N+2 following the patch from the subject cycle by two cycles.

The model includes a segregated stack 401 of layers of the neural network for each of the input patches. Thus, stack 401 receives as input, tile data for the patch from cycle N+2, and is segregated from the stacks 402, 403, 404, and 405 so they do not share input data or intermediate data. In some embodiments, all of the stacks 410-405 can have identical models, and identical trained parameters. In other embodiments, the models and trained parameters may be different in the different stacks. Stack 402 receives as input, tile data for the patch from cycle N+1. Stack 403 receives as input, tile data for the patch from cycle N. Stack 404 receives as input, tile data for the patch from cycle N–1. Stack 405 receives as input, tile data for the patch from cycle N–2. The layers of the segregated stacks each execute a convolution operation of a kernel including a plurality of filters over the input data for the layer. As in the example above, the patch 400 may include three features. The output of the layer 410 may include many more features, such as 10 to 20 features. Likewise, the outputs of each of layers 411 to 416 can include any number of features suitable for a particular implementation. The parameters of the filters are trained parameters for the neural network, such as weights and biases. The output feature set (intermediate data) from each of the stacks 401-405 is provided as input to an inverse hierarchy 420 of temporal combinatorial layers, in which the intermediate data from the multiple cycles is combined. In the example illustrated, the inverse hierarchy 420 includes a first layer including three combinatorial layers 421, 422, 423, each receiving intermediate data from three of the segregated stacks, and a final layer including one combinatorial layer 430 receiving intermediate data from the three temporal layers 421, 422, 423.

The output of the final combinatorial layer 430 is an output patch of classification data for clusters located in the corresponding patch of the tile from cycle N. The output patches can be assembled into an output array classification data for the tile for cycle N. In some embodiments, the output patch may have sizes and dimensions different from the input patches. In some embodiments, the output patch may include pixel-by-pixel data that can be filtered by the host to select cluster data.

The output classification data can then be applied to a softmax function 440 (or other output activation function) optionally executed by the host, or on the configurable processor, depending on the particular implementation. An output function different from softmax could be used (e.g., making a base call output parameter according to largest output, then use a learned nonlinear mapping using context/network outputs to give base quality).

Finally, the output of the softmax function 440 can be provided as base call probabilities for cycle N (450) and stored in host memory to be used in subsequent processing. Other systems may use another function for output probability calculation, e.g., another nonlinear model.

The neural network can be implemented using a configurable processor with a plurality of execution clusters so as complete evaluation of one tile cycle within the duration of the time interval, or close to the duration of the time interval, of one sensing cycle, effectively providing the output data in real time. Data flow logic can be configured to distribute input units of tile data and trained parameters to the execution clusters, and to distribute output patches for aggregation in memory.

Input units of data for a five-cycle input, one-cycle output neural network like that of FIG. 4 are described with reference to FIG. 5 and FIG. 6 for a base call operation using two-channel sensor data. For example, for a given base in a genetic sequence, the base call operation can execute two flows of analyte and two reactions that generate two channels of signals, such as images, which can be processed to identify which one of four bases is located at a current position in the genetic sequence for each cluster of genetic material. In other systems, a different number of channels of sensing data may be utilized.

Figure 5:
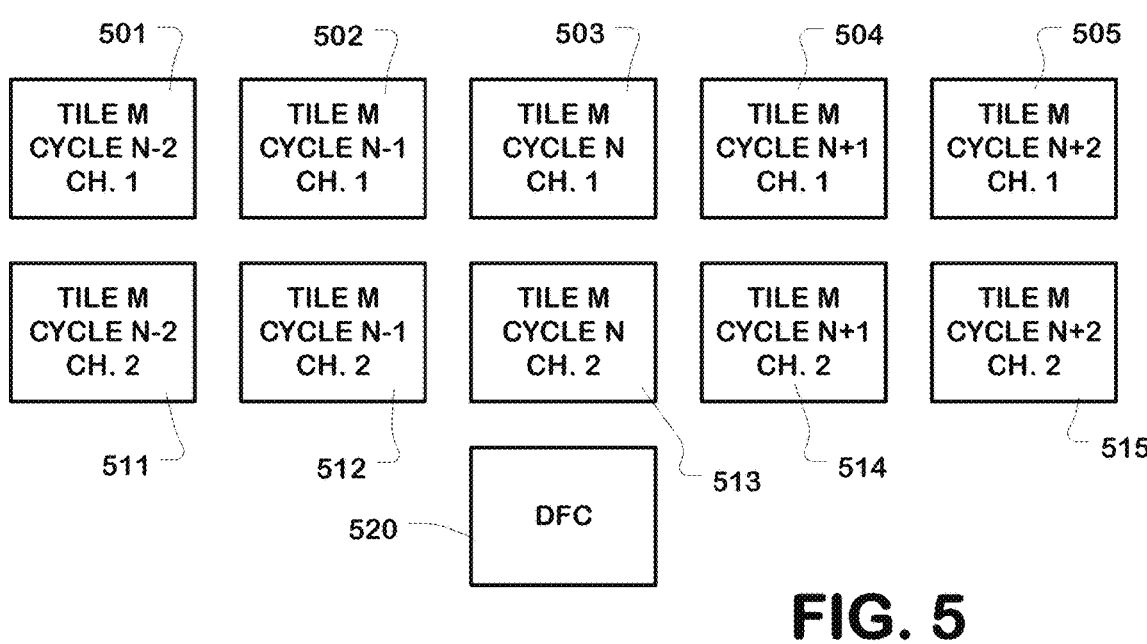
FIG. 5 is a simplified illustration of an organization of tiles of sensor data used by a neural network architecture like that of FIG. 4.

FIG. 5 shows arrays of tile data for five cycles for a given tile, tile M, used for the purposes of executing a five-cycle input, one-cycle output neural network. The five-cycle input tile data in this example can be written to the on-board DRAM, or other memory in the system which can be accessed by the data flow logic and, for cycle N–2, includes an array 501 for channel 1 and an array 511 for channel 2, for cycle N–1, an array 502 for channel 1 and an array 512 for channel 2, for cycle N, an array 503 for channel 1 and an array 513 for channel 2, for cycle N+1, an array 504 for channel 1 and an array 514 for channel 2, for cycle N+2, an array 505 for channel 1 and an array 515 for channel 2. Also an array 520 of metadata for the tile can be written once in the memory, in this case a DFC file, included for use as input to the neural network along with each cycle.

Figure 6:
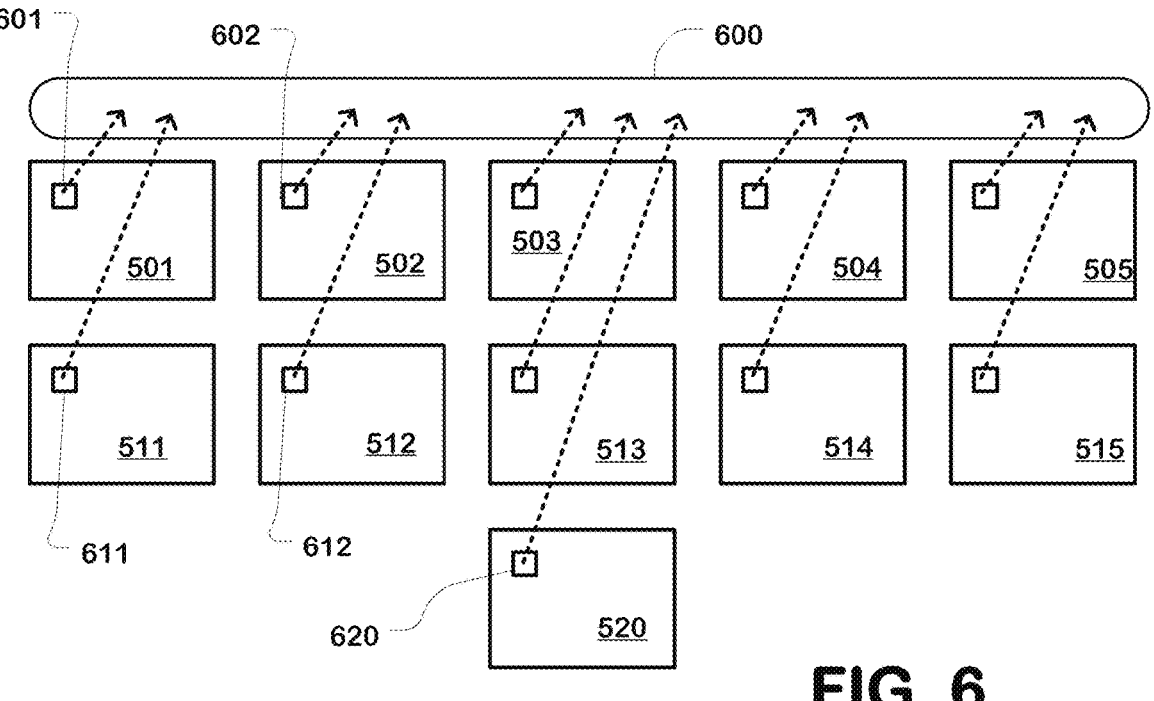
FIG. 6 is a simplified illustration of patches of tiles of sensor data used by a neural network architecture like that of FIG. 4.

The data flow logic composes input units, which can be understood with reference to FIG. 6, of tile data that includes spatially aligned patches of the arrays of tile data for each execution cluster configured to execute a run of the neural network over an input patch. An input unit for an allocated execution cluster is composed by the data flow logic by reading spatially aligned patches (e.g., 601, 602, 611, 612, 620) from each of the arrays 501-505, 511, 515, 520 of tile data for the five input cycles, and delivering them via data paths (schematically 600) to memory on the configurable processor configured for use by the allocated execution cluster. The allocated execution cluster executes a run of the five-cycle input/one-cycle output neural network, and delivers an output patch for the subject cycle N of classification data for the same patch of the tile in the subject cycle N.

Figure 7:
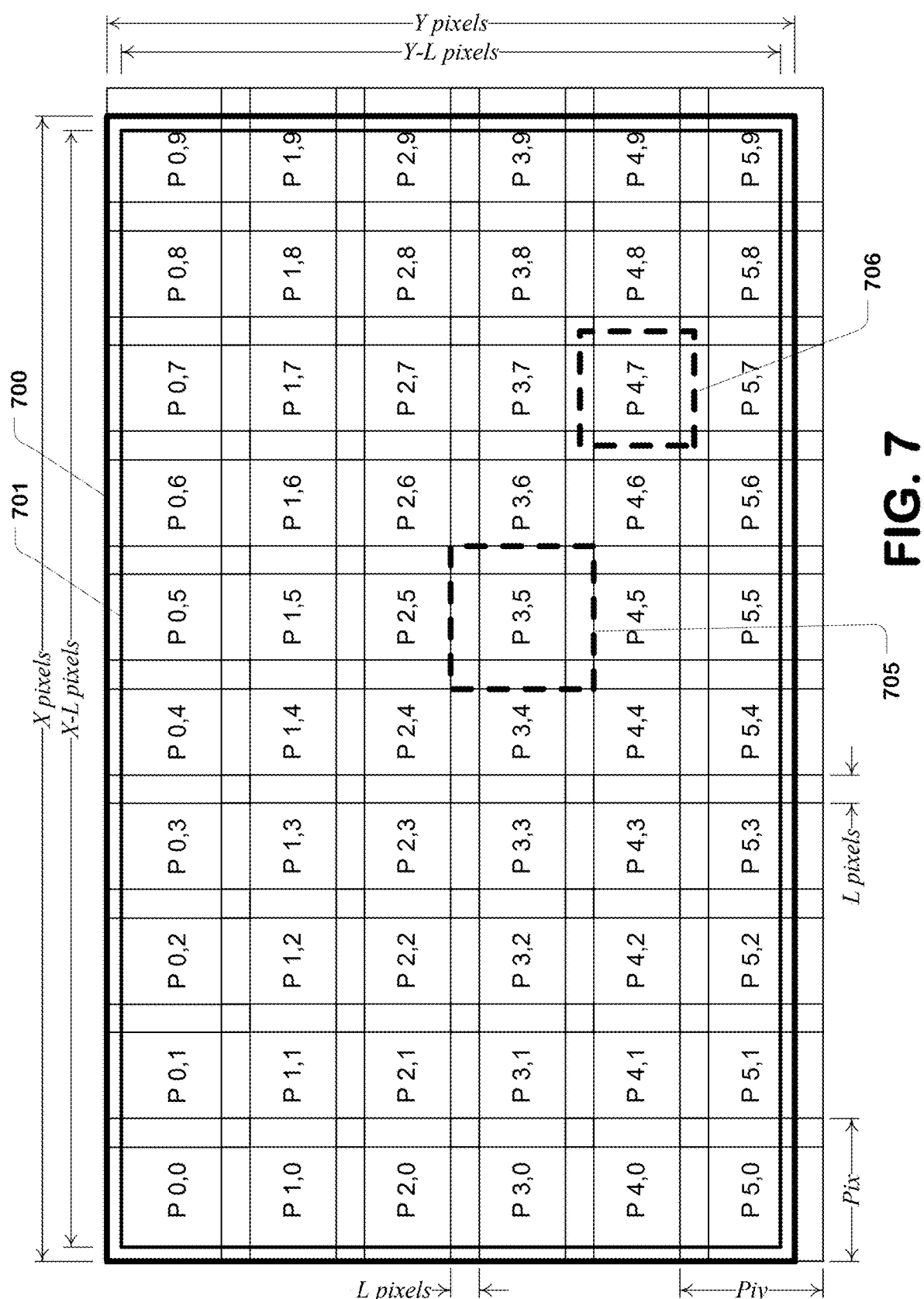
FIG. 7 illustrates a configuration of patches of an input tile used by a neural network architecture like that of FIG. 4.

FIG. 7 illustrates a mapping of patches over an array of tile data for a given tile. In this example, and input array 700 of tile data has a width of X pixels and a height of Y pixels. After convolving a kernel, such as a 3×3 kernel with a stride of one pixel, in a plurality of layers of the neural network, the output tile 701 can be reduced by two rows and two columns per layer of the neural network. The reduction by two rows/columns is caused in this example, by the kernel size of 3×3 and the type of (edge) padding in use and can be different in different configurations. So, for example, the output tile 701 of classification data will have a width of X-L pixels, for a neural network comprising L/2 layers of convolutions of this type. Likewise, the output tile of classification data will have a height of Y-L pixels for a neural network comprising L/2 layers. For example, taking a neural network having six layers, L can be 12 pixels. In the example shown in FIG. 7, the patch areas are not drawn to scale.

The input patches are formed in an overlapping manner to account for lost pixels that result from the convolutions over the patch dimensions. The sizes of the input patches can be chosen according to the particular implementation. In one example, an input patch may have a dimension of 76×76 pixels, with three channels of one or more bytes each. An output patch may have a dimension of 64×64 pixels. In an embodiment, base call operation output classifications for A/C/T/G base calls, and the output patch may include four channels of one or more bytes for each pixel representing confidence scores for the classifications. In the example of FIG. 4, the outputs on line 435 are unnormalized confidence scores for four base calls.

The data flow logic can address the array of tile data to patches in a raster scan fashion, or other scanning fashion to provide input patches (e.g., 705). For example, for the first available cluster, patch P0,0 can be provided. For a next available cluster, patch P0,1 can be provided. This sequence can be continued in a raster pattern until all of the patches of the tile are delivered to available clusters for processing.

Output patches (e.g., 706) can be written back in the same address space aligned with their subject input patches in some embodiments, accounting for any differences in the number of bytes per pixel used to encode the data. The output patches have an area (number of pixels) reduced relative to the input patches according to the number of convolution layers, and the nature of the convolutions executed.

Figure 8:
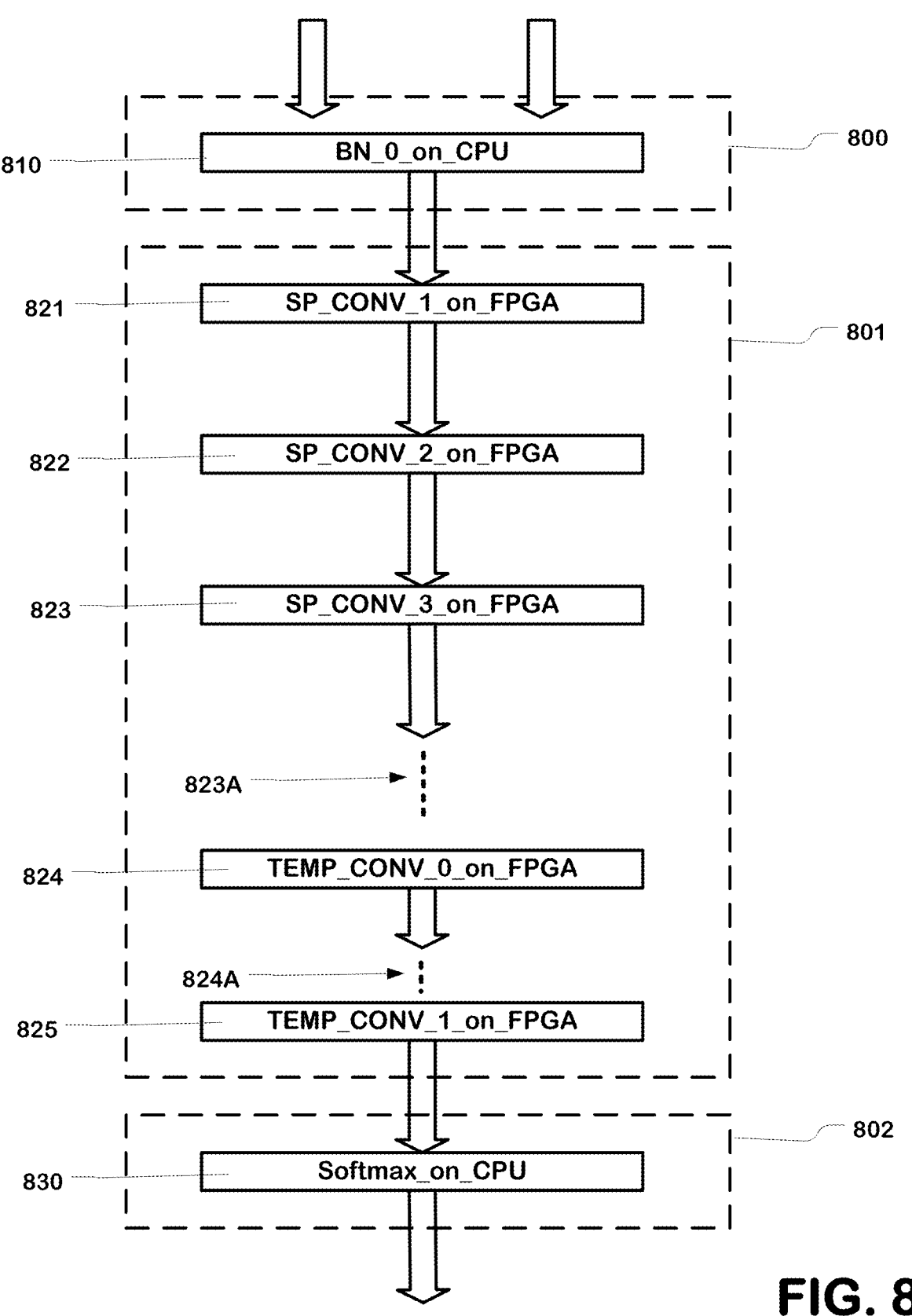
FIG. 8 illustrates part of a configuration for a neural network like that of FIG. 4 on a configurable or a reconfigurable array, such as a field programmable gate array (FPGA).

FIG. 8 is a simplified representation of a stack of a neural network usable in a system like that of FIG. 4 (e.g., 401 and 420). In this example, some functions of the neural network are executed on the host (e.g., 800, 802) and other portions of the neural network are executed on the configurable processor (801).

A first function can be batch normalization (layer 810) formed on the CPU. Batch normalization is a training technique that improves overall performance results by normalizing data on a per-batch basis, although other techniques can be used. Several parameters per layer are calculated and updated during training.

During inference, batch normalization parameters do not adapt and are fixed at long-term averages. Multiplication operations can be fused into adjacent layers to reduce the total operation count. This fusing is performed during fixed point model retraining, so the inference neural network can contain a single addition within each of the BN layers implemented in the configurable processor. The first Batch Normalization layer 810 is performed on the CPU in training. This is the only layer that is performed on the CPU. The output of the Batch Normalization calculation is quantized, and the outputs are transferred to the configurable processor for further processing. After training, batch normalization is replaced by a fixed scaling and bias addition. In the first layer, this scaling and bias addition occurs on the CPU. In an inference only implementation, batch normalization term does not really need to be used.

A number of spatial, segregated convolution layers are executed as a first set of convolution layers of the neural network, as discussed above on the configurable processor. In this example, the first set of convolution layers applies 2D convolutions spatially.

These convolutions can be efficiently implemented using a stack of 2D Winograd convolutions. The operations are applied on each patch in each cycle independently. The multiple-cycle structure is preserved through these layers. There are different ways to implement the convolution, this is an efficient way for digital logic and programmable processors.

As shown in FIG. 8, a first spatial convolution 821 is executed, followed by a second spatial convolution 822, followed by a third spatial convolution 823, and so on for a number L/2 of spatially segregated neural network layers in each stack (L is described with reference to FIG. 7). As indicated at 823A, the number of spatial layers can be any practical number, which for context may range from a few to more than 20 in different embodiments.

For SP_CONV_0, kernel weights are stored for example in a (1,6,6,3,L) structure since there are 3 input channels to this layer. In this example, the "6" in this structure is due to storing coefficients in the transformed Winograd domain (the kernel size is 3×3 in the spatial domain but expands in the transform domain).

For other SP_CONV layers, kernel weights are stored for this example in a (1,6,6 L) structure since there are K(=L) inputs and outputs for each of these layers.

The outputs of the stack of spatial layers are provided to temporal layers, including convolution layers 824, 825 executed on the FPGA. Layers 824 and 825 can be convolution layers applying 1D convolutions across cycles. As indicated at 824A, the number of temporal layers can be any practical number, which for context may range from a few to more than 20 in different embodiments.

The first temporal layer, TEMP_CONV_0 layer 824, reduces the number of cycle channels from 5 to 3, as illustrated in FIG. 4. The second temporal layer, layer 825, reduces the number of cycle channels from 3 to 1 as illustrated in FIG. 4, and reduces the number of feature maps to four outputs for each pixel, representing confidence in each base call.

The output of the temporal layers is accumulated in output patches and delivered to the host CPU to apply for example, a softmax function 830, or other function to normalize the base call probabilities.

Figure 9:
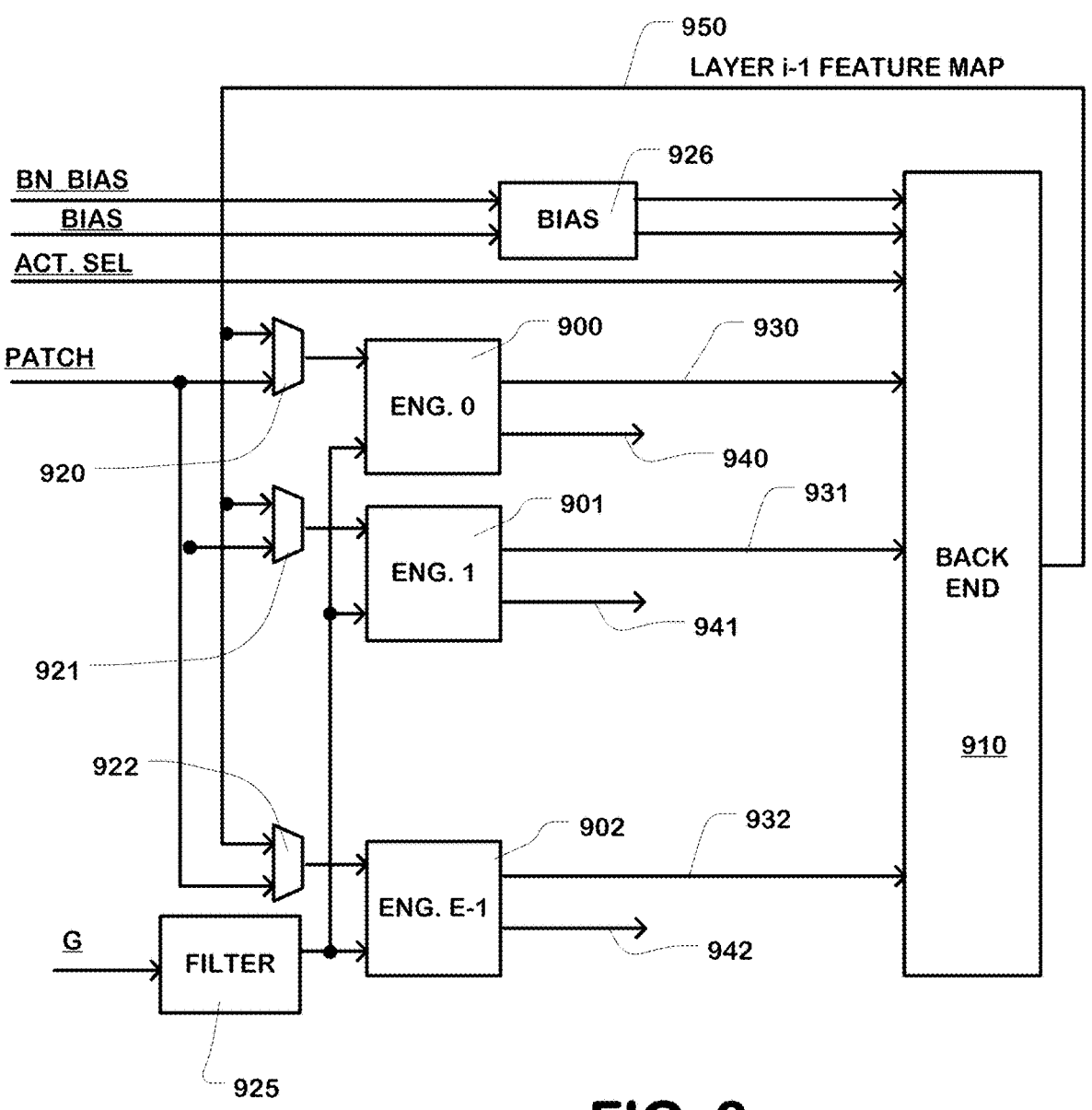
FIG. 9 illustrates a configuration of a multi-cycle machine learning cluster which can be used to execute a neural network like that of FIG. 4.

FIG. 9 is a block diagram of a configuration for an execution cluster suitable for execution of a multi-cycle neural network as described herein. In this example, the execution cluster includes a plurality of execution engines ENG. 0 to ENG. E−1 (e.g., 900, 901, 902). The number N can be any value selected according to design trade-offs. For practical examples, when the engines are implemented on a single FPGA, the number N may be in the range of 6 to 10 for each cluster although more or fewer engines may be configured. Thus, the execution cluster includes a set of computation engines having plural members, configured to convolve trained parameters over input data for multiple layers of the neural network, wherein input data for a first layer is from the input unit, and the data for subsequent layers is from activation data output from a previous layer.

The engines include a front end which provides current data, filter parameters and control to allocated engines, which engines execute loops of multiply-and-accumulate functions supporting the convolutions, and a backend, which includes the circuits for applying bias and other functions in support of the neural network. In this example, the front end includes a plurality of selectors 920, 921, 922 used to select the source of data for the allocated engines from input patch (PATCH) delivered by the data flow logic from an on-board DRAM or other memory source, or from activation data fed back from a previous layer on a line 950 from the backend 910. Also, the front end includes a filter store 925 which is connected to a source of filter parameters stored for use in the execution of the convolutions. Filter store 925 is coupled to each of the engines and provides suitable parameters according to the portion of the convolution to be executed in the particular engines. The output of the engines includes a first path 930, 931, 932 providing a result to the backend 910. Also, the output of the engines includes a second path 940, 941, 942 which is connected to the data flow logic in the wrapper for routing data back to on-board memory, or other memory utilized by the system. Also, the cluster includes a bias store 926 loaded with various biased values BN_BIAS and BIAS utilized in the execution of the neural network. The bias store 926 is operated to provide the particular bias values to the backend (910) processes according to the particular state of the neural network being executed.

Clusters in the plurality of clusters in the neural network processor can be configured to include kernel memory to store the trained parameters, and the data flow logic can be configured to provide instances of trained parameters to the kernel memory of execution clusters in the plurality of execution clusters for use in execution of the neural network. Weights used for the layers can be trained parameters which are changed for example as a function of sensing cycle, such as every X cycles where X can be a constant like 15 or 20, selected empirically. Also, the number X can be variable according to the characteristics of the sequencing system that provides the input tile data.

Figure 10:
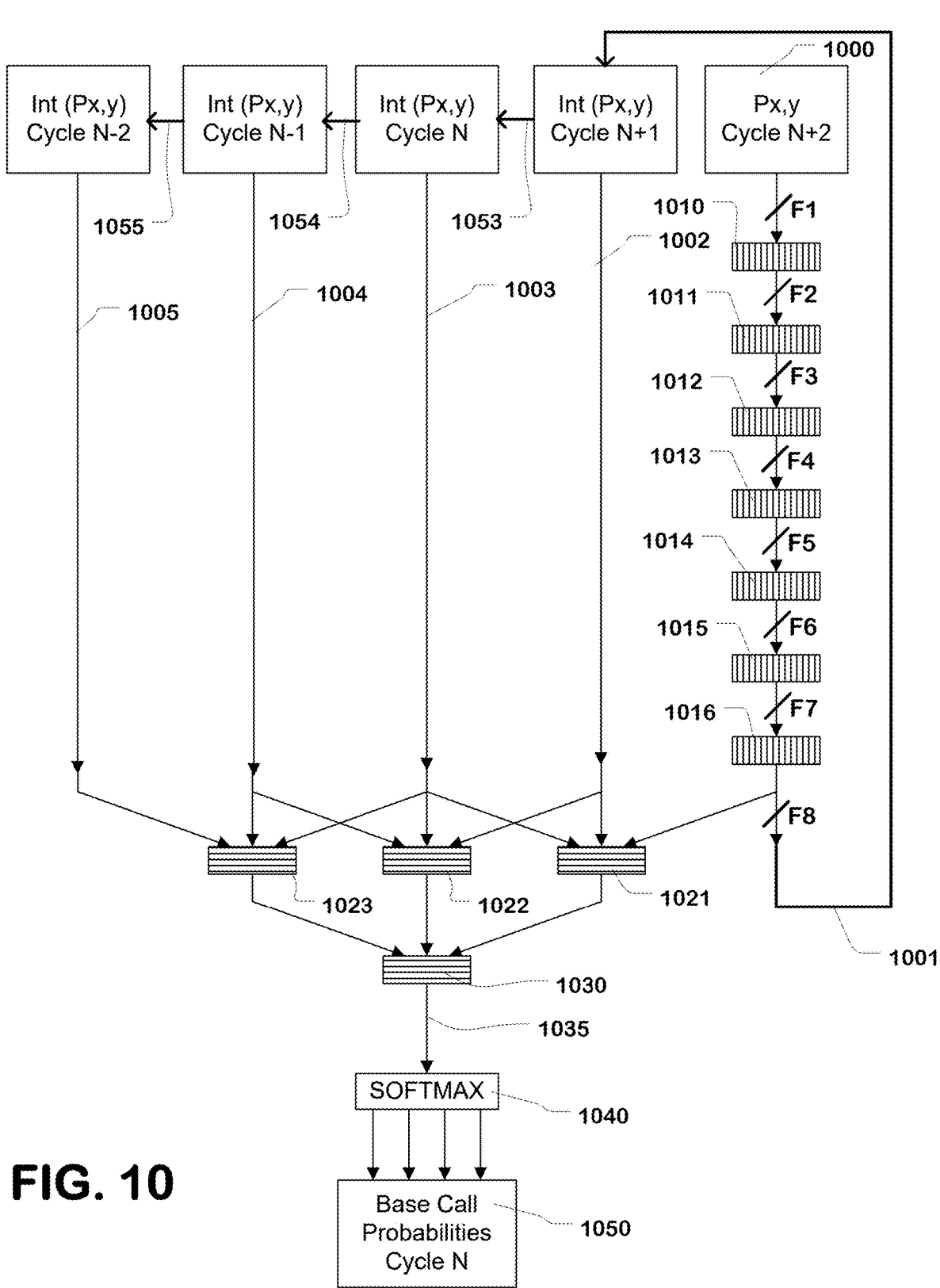
FIG. 10 is a diagram of an alternative neural network architecture which can be executed using a configurable or a reconfigurable array configured as described herein.

FIG. 10 is a diagram of a multi-cycle neural network model which can be equivalent to the model shown in FIG. 4 but executed reusing intermediate data to save computational resources. As shown in FIG. 10, the model is a five-cycle input, one-cycle output neural network. The inputs to the neural network include a current patch Px,y (1000) from the tile data arrays which includes sensor data from a current sensing cycle of a given tile. Also, the inputs include intermediate data Int(Px,y) from previous spatially aligned patches from cycles N–2, N–1, N and N+1.

The input patch 1000 from cycle N+2 is applied to a segregated stack of layers including layers 1010, 1011, 1012, 1013, 1014, 1015, 1016. The output of the final layer 1016 of the segregated stack is applied on line 1001 for use as the intermediate data for a subsequent run of the neural network and passed down for reuse multiple times as illustrated by lines 1053, 1054, 1055. This intermediate data can be written back to the on-board DRAM as tile data for the particular tile and the particular cycle, or other memory resources. In some embodiments, the intermediate data can be written over the same locations as the original array of sensor data of the tile data for the spatially aligned patch.

In FIG. 10, the input patch 1000 has a number of features F1 which are applied to the first layer 1010 of the neural network. The layer 1010 outputs a number of features F2 to the next layer 1011. The next layer outputs a number of features F3 and so on so succeeding layers output F4 features, F5 features, F6 features, F7 features and F8 features, respectively. In some embodiments, the number of features F1 can be 3, as discussed above with respect to the sensor data of the input patch. The number of features F2 through F8 can be 12 or more and be the same or different. In this case, the 12 (or more) features of the final layer 1016 can consume more memory than input patch 1000, because it includes more features. In other embodiments, the number of features F2 through F8 can vary.

In some memory-efficient embodiments, the number of features F8 can be reduced to preserve memory resources when used as intermediate data. For example, the number of features F8 can be 2 features or 3 features, so that it consumes the same or less memory space than the original input patch when it is stored as tile data for the subject cycle.

In the model shown in FIG. 10, the intermediate data for cycles N–2, N–1, N and N+1 are applied on lines 1002, 1003, 1004, 1005 as inputs to the temporal layers 1021, 1022, 1023 and in the manner discussed respect to FIG. 4. Also, the output of the layer 1016 of the segregated stack is applied as an input to the layer 1021 of the temporal layers. The final temporal layer 1030 receives as input outputs of the temporal layers 1021-1023. Output of the layer 1030 is applied on line 1035 to a softmax function 1040 or other activation function, the output of which is provided as base call probabilities 1050 for the subject cycle, cycle N.

Thus, for the neural network model of FIG. 10, the tile data for a sensing cycle in the memory includes sensor data for the current sensing cycle (N+2) and intermediate data fed back from the neural network for the earlier sensing cycles (N–2, N–1, N and N+1).

Figure 11:
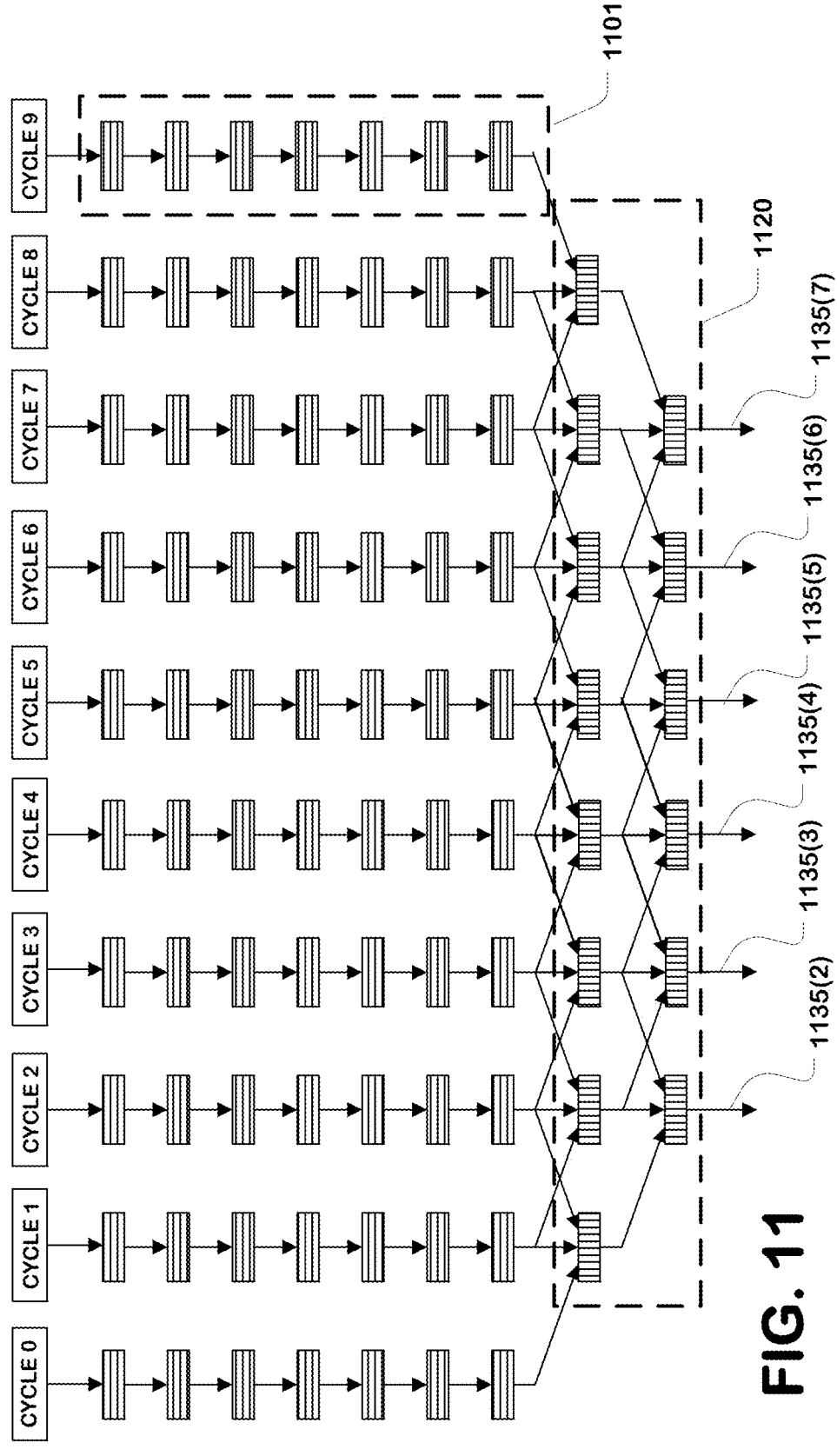
FIG. 11 is a diagram of another alternative neural network architecture which can be executed using a configurable or a reconfigurable array configured as described herein.

FIG. 11 illustrates an alternative implementation showing a 10-input, six-output neural network which can be executed for a base calling operation. In a system like FIG. 11, a save and reuse approach like that of FIG. 10 can be used to substantially improve efficiency. In this example, tile data for spatially aligned input patches from cycles 0 to 9 are applied to segregated stacks of spatial layers, such as stack 1101 for cycle 9. The outputs of the segregated stacks are applied to an inverse hierarchical arrangement of temporal stacks 1120, having outputs 1135(2) through 1135(7) providing base call classification data for subject cycles 2 through 7.

Figure 12:
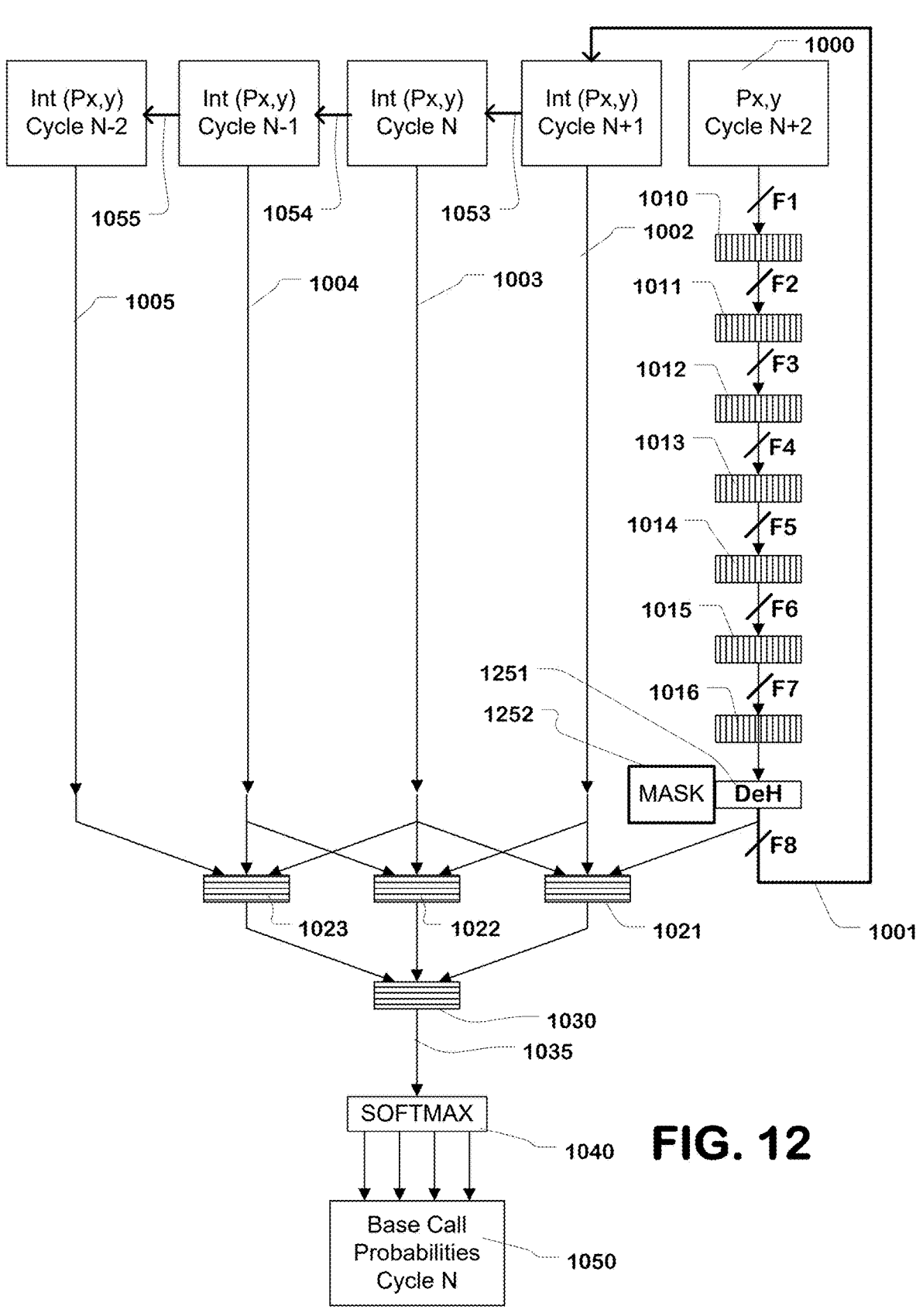
FIG. 12 is a diagram of yet another alternative neural network architecture which can be executed using a configurable or a reconfigurable array as described herein, utilizing a mask that can reduce memory and processing requirements for all the neural network embodiments described herein.

FIG. 12 illustrates an improvement of the model shown in FIG. 10 and includes like features having the same reference numbers. FIG. 12 is distinct from FIG. 10 in that it includes a "dehydration" filter layer 1251 and a tile cluster mask 1252 at the output of layer 1016. The tile cluster mask 1252 can be generated by preprocessing of the sensor data to identify pixels in the images that correspond to clusters of genetic material being sequenced. The tile cluster mask 1252 can be applied in a configurable processor including mask logic to apply the tile cluster mask to intermediate data in the neural network. The mask logic can include a "dehydration" filter layer to select only pixels that have data relevant to a base calling operation (e.g., reliable cluster data) and to rearrange the pixels in a smaller intermediate data array, and therefore can substantially reduce the size of the intermediate data, and the size of the data applied to the temporal layers.

The tile cluster mask 1252 can be generated for example as described in U.S. Patent Application Publication No. US 2012/0020537, by Garcia et al., which is incorporated by reference as if fully set forth herein, where the locations identified of features can be the locations of clusters of genetic materials.

The tile cluster mask 1252 can identify those pixels that correspond to unreliable clusters and can be used by the dehydration filter layer to discard/filter out such pixels, and thereby apply the temporal layers only on those pixels that correspond to reliable clusters. In one implementation, the base call classification scores are generated by an output layer. Examples of the output layer include a softmax function, a log-softmax function, an ensemble output average function, a multi-layer perceptron uncertainty function, a Bayes Gaussian distribution function, and a cluster intensity function. In one implementation, the output layer produces a per-cluster, per-cycle probability quadruple for each cluster and for each sequencing cycle.

The following discussion focuses on the per-cluster, per-cycle probability quadruples using the softmax function as an example of the output layer. We first explain the softmax function and then the per-cluster, per-cycle probability quadruples, which are used to identify unreliable clusters.

Softmax function is a preferred function for multi-class classification. The softmax function calculates the probabilities of each target class over all possible target classes. The output range of the softmax function is between zero and one and the sum of all the probabilities is equal to one. The softmax function computes the exponential of the given input value and the sum of exponential values of all the input values. The ratio of the exponential of the input value and the sum of exponential values is the output of the softmax function, referred to herein as "exponential normalization."

Formally, training a so-called softmax classifier is regression to a class probability, rather than a true classifier as it does not return the class but rather a confidence prediction of each class's probability. The softmax function takes a class of values and converts them to probabilities that sum to one. The softmax function squashes a n-dimensional vector of arbitrary real values to n-dimensional vector of real values within the range zero to one. Thus, using the softmax function ensures that the output is a valid, exponentially normalized probability mass function (nonnegative and summing to one).

Intuitively, the softmax function is a "soft" version of the maximum function. The term "soft" derives from the fact that the softmax function is continuous and differentiable. Instead of selecting one maximal element, it breaks the vector into parts of a whole with the maximal input element getting a proportionally larger value, and the other getting a less proportion of the value. The property of outputting a probability distribution makes the softmax function suitable for probabilistic interpretation in classification tasks.

Let us consider z as a vector of inputs to the softmax layer. The softmax layer units are the number of nodes in the softmax layer and therefore, the length of the z vector is the number of units in the softmax layer (if we have ten output units, then there are ten z elements).

For an n-dimensional vector $Z=[z_1, z_2, \ldots z_n]$, the softmax function uses exponential normalization (exp) to produce another n-dimensional vector $p(Z)$ with normalized values in the range $[0, 1]$ and that add to unity:

$$Z = \begin{bmatrix} z_1 \\ z_2 \\ \vdots \\ z_n \end{bmatrix} \text{ and, } p(Z) \rightarrow \begin{bmatrix} p_1 \\ p_2 \\ \vdots \\ p_n \end{bmatrix}$$

$$p_j = \frac{\exp^{z_j}}{\sum\limits_{k=1}^{n} \exp^{z_k}} \forall j \in 1, 2, \ldots, n$$

Softmax function is applied to three classes as $$z \mapsto \text{softmax}\left(\left[z; \frac{z}{10}; -2z\right]\right).$$

Note that the three outputs always sum to one. They thus define a discrete probability mass function.

A particular per-cluster, per-cycle probability quadruple identifies probabilities of a base incorporated in a particular cluster at a particular sequencing cycle being A, C, T, and G. When the output layer of the neural network-based base caller uses a softmax function, the probabilities in the per-cluster, per-cycle probability quadruple are exponentially normalized classification scores that sum to unity. An unreliable cluster identifier identifies unreliable clusters based on generating filter values from the per-cluster, per-cycle probability quadruple. In this application, the per-cluster, per-cycle probability quadruples are also referred to as base call classification scores or normalized base call classification scores or initial base call classification scores or normalized initial base call classification scores or initial base calls.

A filter calculator determines a filter value for each per-cluster, per-cycle probability quadruple based on the probabilities it identifies, thereby generating a sequence of filter values for each cluster. The sequence of filter values is stored as filter values.

The filter value for a per-cluster, per-cycle probability quadruple is determined based on an arithmetic operation involving one or more of the probabilities. In one implementation, the arithmetic operation used by the filter calculator is subtraction. In one implementation, the filter value for the per-cluster, per-cycle probability quadruple is determined by subtracting a second highest one of the probabilities from a highest one of the probabilities.

In another implementation, the arithmetic operation used by the filter calculator is division. For example, the filter value for the per-cluster, per-cycle probability quadruple is determined as a ratio of the highest one of the probabilities to the second highest one of the probabilities. In yet another implementation, the arithmetic operation used by the filter calculator is addition. In yet further implementation, the arithmetic operation used by the filter calculator is multiplication.

In one implementation, the filter calculator generates the filter values using a filtering function. In one example, the filtering function is a chastity filter that defines chastity as a ratio of a brightest base intensity divided by a sum of the brightest base intensity and a second brightest base intensity. In another example, the filtering function is at least one of a maximum log probability function, a minimum squared error function, average signal-to-noise ratio (SNR), and a minimum absolute error function.

The unreliable cluster identifier uses the filter values to identify some clusters in the plurality of clusters as unreliable clusters. Data identifying the unreliable clusters can be in computer readable format or medium. The unreliable clusters can be identified by instrument ID, the run number on the instrument, the flow cell ID, the lane number, the tile number, the X coordinate of the cluster, the Y coordinate of the cluster, and unique molecular identifiers (UMIs). The unreliable cluster identifier identifies those clusters in the plurality of clusters as unreliable clusters whose sequences of filter values contain "N" number of filter values below a threshold "M." In one implementation, the "N" ranges from 1 to 5. In another implementation, the "M" ranges from 0.5 to 0.99. In one implementation, the unreliable clusters identify those pixels that correspond to (i.e., depict intensity emissions of) the unreliable clusters.

Unreliable clusters are low-quality clusters that emit an amount of desired signal which is insignificant compared to background signal. The signal to noise ratio for unreliable clusters is substantially low, for example, less than one. In some implementations, unreliable clusters may not produce any amount of a desired signal. In other implementations, unreliable clusters may produce a very low amount of signal relative to background. In one implementation, the signal is an optical signal and is intended to include, for example, fluorescent, luminescent, scatter, or absorption signals. Signal level refers to an amount or quantity of detected energy or coded information that has a desired or predefined characteristic. For example, an optical signal can be quantified by one or more of intensity, wavelength, energy, frequency, power luminance or the like. Other signals can be quantified according to characteristics such as voltage, current, electric field strength, magnetic field strength, frequency, power, temperature, etc. Absence of signal in unreliable clusters is understood to be a signal level of zero or a signal level that is not meaningfully distinguished from noise.

There are many potential reasons for poor quality signals of unreliable clusters. If there has been a polymerase chain reaction (PCR) error in colony amplification such that a sizable proportion of the ~1000 molecules in an unreliable cluster contains a different base at a certain position, then one may observe a signal for two bases—this is interpreted as a sign of poor quality and referred to as phase error. Phase error occurs when individual molecules in an unreliable cluster do not incorporate a nucleotide in some cycle (e.g., because of incomplete remove of 3' terminators, termed phasing) and then lag behind the other molecules, or when an individual molecule incorporates more than one nucleotide in a single cycle (e.g., because of incorporation of nucleotides without effective 3'-blocking, termed prephasing). This results in the loss of synchrony in the readout of the sequence copies. The proportion of sequences in unreliable clusters that are affected by phasing and pre-phasing increases with cycle number, which is a major reason why the quality of reads tends to decline at high cycle numbers.

Unreliable clusters also result from fading. Fading is an exponential decay in signal intensity of unreliable clusters as a function of cycle number. As the sequencing run progress, the strands in unreliable clusters are washed excessively, exposed to laser emissions that create reactive species, and subject to harsh environmental conditions. All of these lead to a gradual loss of fragments in unreliable clusters, decreasing their signal intensity.

Unreliable clusters also result from underdeveloped colonies, i.e., small cluster sizes of unreliable clusters that produce empty or partially filled wells on a patterned flow cell. That is, in some implementations, the unreliable clusters are indicative of empty, polyclonal, and dim wells on the patterned flow cell. Unreliable clusters also result from overlapping colonies caused by unexclusive amplification. Unreliable clusters also result from under-illumination or uneven-illumination, for example, due to being located on the edges of a flow cell. Unreliable clusters also result from impurities on the flow cell that obfuscate emitted signal. Unreliable clusters also include polyclonal clusters when multiple clusters are deposited in the same well.

Figure 13:
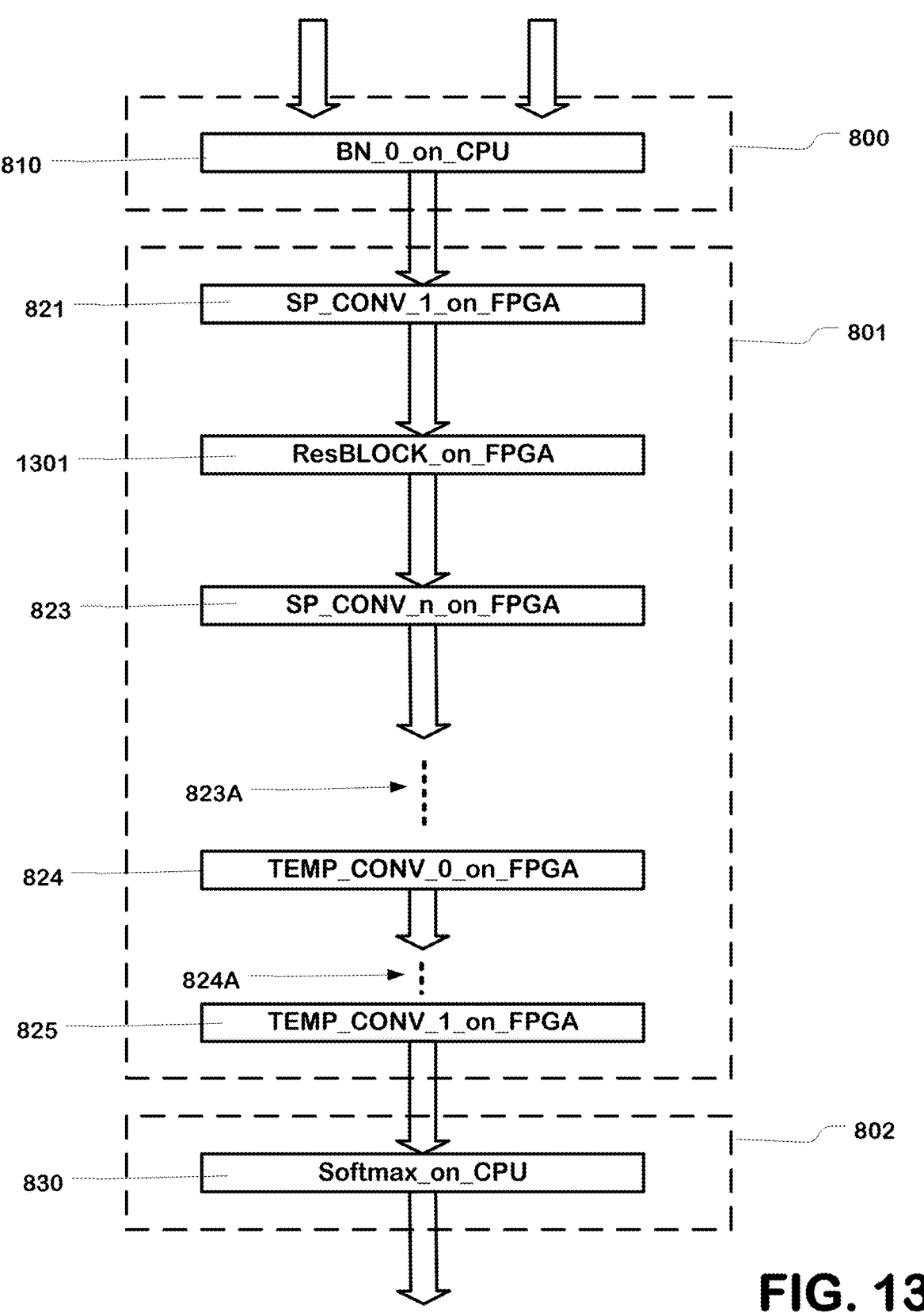
FIG. 13 illustrates an embodiment of the deep neural network to use a residual block stage, which can be implemented using a configurable or a reconfigurable array as described herein.

FIG. 13 illustrates an alternative implementation of the deep neural network which can be executed. FIG. 13 is in the form of FIG. 8 and includes the same reference numerals for like components. In FIG. 13, one or more of the spatial convolution layers in the segregated stack is replaced by a residual block structure 1301 (ResBLOCK). The residual block structure in one example configuration, can include a first convolutional layer and a second convolutional layer, which receive as input a sum of the input to the first convolutional layer and the output of the first convolutional layer. The second convolutional layer in the residual block 1301 may have no activation function after the addition.

FIG. 14 is a simplified flowchart for a base call operation using a system like that of FIG. 1. In this simplified process, a runtime program executed by the CPU 102 initiates a base call operation (1401). This can include instantiating one or more processing threads which can run on multiple cores of the host CPU. In the base call operation, the sensors and flow cell are executed in a sequence of cycles in which arrays of tile data are generated. The processing threads wait for and receive data from a sequence of sensing cycles (e.g., tile images) across clusters of genetic material in the tiles of the flow cell (1402). The output from the flow cell is processed for example between the sensing operation and the neural network by resampling so that each image has a common structure and common reference frame, e.g., fiducials are aligned, clusters/wells are aligned, DFC data is constant, and by arranging the data in sequences of arrays of tile data, where each sequence can include one array of tile data including a number F features for each sensing cycle (1403). This resampling and arrangement of the tile images is performed because the neural network performance is improved when the same pixel in each of its training inputs conveys the same information about the underlying signal coming from the flow cell. The processing thread transfers the arrays of tile data and neural network trained parameters to the memory 1060 via the wrapper (data flow logic 151) on the configurable processor. When sufficient data, such as N complete arrays of tile data including a subject tile and a plurality of adjacent tiles for N cycles, has been loaded in memory 140 (e.g., responsive to control signals like control triggers and/or control tokens (feed-forward single pulse) formed or issued on the bus), the processing thread can submit the jobs to the inference engine by issuing a signal the event to the wrapper, or the wrapper can detect the event, to begin a run of the neural network over a particular subject tile (1404). The wrapper loads the trained parameters for the neural network to the available logic clusters, allocates an available logic cluster and loads spatially aligned patches from the number N cycles (1405). The wrapper can update the neural network parameters as a function of cycle number in the sequence, using ping-pong buffering for example (1406). For example, the neural network model parameters (weights and biases) can be updated every 20 cycles in a particular implementation. Thus, the wrapper has access to the memory and to execution clusters in the plurality of execution clusters and includes logic to provide input units of tile data to available execution clusters in the plurality of execution clusters, and to cause the execution clusters to apply tile data of the spatially aligned patches from each of N cycles of the input units to the neural network to produce output patches of classification data for the subject cycle. The DRAM can be configured with enough allocated space to store supporting a five cycle inference engine, four cycle's worth of images for each tile on the flow cell. With pointer juggling, the fifth buffer needed for inference can live in the host processor memory allocated to the particular processing thread (The number of tiles is typically much greater than the number of instantiated processor threads).

After running the neural network over the allocated patch, the clusters return output patches for the subject cycle of the N cycles via the wrapper to the memory 140, and signal availability to the wrapper (1407). The wrapper tracks the sequence of patches to traverse the array of tile data, arranges the output patches, and signals the waiting processor thread in the host when the output tile or other unit of the tile data has been composed in memory 140 (1408). Thus, the wrapper can include logic to assemble the output patches from the plurality of execution clusters to provide an array of base call classification data for the subject cycle, and to store the array of base call classification data in memory. The composed output tile is either retrieved by the host, or pushed to the host by the wrapper, for further processing (1409). Optionally, as described above, the output tile can comprise classification data in an un-normalized form, such as four logits for each pixel, or for each pixel corresponding to a cluster. In this case, the host can execute a softmax or other type of normalizing function over the tile data, in preparation for composing base call files and quality scores (1410).

FIG. 15 is a simplified flowchart for one embodiment of a logic cluster flow in a system like that of FIG. 1 for a neural network like that of FIG. 4. A logic cluster flow is initiated by a wrapper as discussed in FIG. 16, and an input unit including N spatially aligned patches is moved to memory of the cluster (1501). The logic cluster allocates an available engine or engines, and routes spatially aligned sub-patches of the N spatially aligned patches to the allocated engines (1502). The tile data for the current input cycle of spatially aligned patches includes N patches of tile data from a current cycle (cycle N+2) and N-1 previous cycles (cycles N-2, N-1, N, and N+1) (1503). Each engine of the cluster can be configured with enough memory to hold the set of spatially aligned sub-patches of data that is currently being worked on in place, and a sub-patch of data that is to be worked on when the current batch processing is finished using for example a ping-pong input buffer structure or other memory management techniques.

The allocated engine loops through the filters applied in the layers of the network including applying a filter set for the current network layer and returning activation data for a next layer (1504). In this example, the neural network includes a first stage that comprises a number N segregated spatial stacks, which feeds a second stage which comprises a reverse hierarchical set of temporal layers. The last layer of the network generates an output of four features, each feature representing classification for each of the four bases A/C/G/T (adenine (A), cytosine (C), guanine (G), and thymine (T)) when being executed to classify DNA or A/C/G/U ((adenine (A), cytosine (C), guanine (G), and uracil (U)) when being executed to classify bases (1505).

In this example, the neural network parameters include a tile cluster mask to identify locations of genetic clusters in the tiles (1506). In one implementation, a template generation step identifies xy location coordinates of reliable clusters, for example, the one disclosed in U.S. Patent Application Publication No. US 2012/0020537, by Garcia et al. The intermediate data generated by the final spatial layer in the stack is reduced ("dehydrated") by the engine, in this example flow, by mask logic in the configurable processor using the mask to remove pixels that do not correspond to the locations of clusters in the tile, resulting in a smaller amount of activation data for the subsequent layers (1507).

The engine returns features of output sub-patch for the subject cycle (middle cycle), and signals availability to the logic cluster (1508). The logic cluster continues executing on the current patch, until all of the features of a current layer of the network for the patch are completed, and then traverses a next allocated patch assigning sub-patches to engines and assembling the output sub-patches until completion of the allocated patch (1509). Finally, the wrapper transfers the output patch to the memory for assembly into an output tile (1510).

FIG. 16 is a simplified flowchart for one embodiment of a logic cluster flow in a system like that of FIG. 1, for a neural network like that of FIG. 10. A logic cluster flow is initiated by a wrapper as discussed with reference to FIG. 16, and an input unit including N spatially aligned patches is moved to memory of the cluster (1601). The logic cluster allocates an available engine or engines, and routes spatially aligned sub-patches of the N spatially aligned patches to the allocated engines (1602). The spatially aligned patches include a patch the array of tile data for a current cycle (e.g., cycle N+2) that includes sensor data having F features (or channels), and N-1 patches of intermediate data computed using previous cycles (cycles N-2, N-1, N, and N+1) (1603). Each engine of the cluster can be configured with enough memory to hold the set of spatially aligned sub-patches of data that are currently being worked on in place, and the sub-patches to be worked on when the current sub-patch processing is finished using, for example, a ping-pong input buffer structure or other memory management techniques.

The allocated engine loops through the filters applied in the spatial layers, and the layers of the network for a segregated stack applied to the current cycle (cycle N+2), including for a given layer applying a filter set for the current network layer and returning activation data for next layer (1604). In this example, the neural network includes a first stage that comprises one segregated spatial stack for the current cycle, and a second stage which comprises a reverse hierarchical set of temporal layers, as shown in FIG. 10.

The engine returns activation data for the current input cycle sub-patch to the logic cluster at the end of the first stage for use as intermediate data in the following cycles (1606). This intermediate data can be stored back to the on-board memory in the location of the tile data for the responding cycle, replacing the sensor data, or in other locations. The final layer of the spatial layers has a number F or fewer features, for example, so that the amount of memory used for tile data for the cycles does not expand with the intermediate data (1607). Also, in this example, the neural network parameters include a tile cluster mask identifying locations of genetic clusters in the tile (1608). The intermediate data from the final spatial layer is "dehydrated" in the engine using the mask, or in another engine allocated by the cluster (1609). This reduces the size of the output sub-patch, which is used as intermediate data, and which is applied to the second stage.

After processing the segregated spatial stack for the current cycle, the engine loops through the temporal layers of the network using activation data from the current input cycle (cycle N+2), and intermediate data from the N-1 previous cycles (1610).

The engine returns features of the output sub-patch for the subject cycle (cycle N), and signals availability to the logic cluster (1611). The logic cluster accumulates output sub-patches to form an output patch (1612). Finally, the wrapper transfers the output patch to the memory for assembly into an output tile (1613).

FIG. 17 illustrates one implementation of the specialized architecture of the neural network-based base caller (e.g., FIG. 4 and FIG. 10) that is used to segregate processing of data for different sequencing cycles. The motivation for using the specialized architecture is described first.

The neural network-based base caller processes data for a current sequencing cycle, one or more preceding sequencing cycles, and one or more successive sequencing cycles. Data for additional sequencing cycles provides sequence-specific context. The neural network-based base caller learns the sequence-specific context during training and base call them. Furthermore, data for pre and post sequencing cycles provides second order contribution of pre-phasing and phasing signals to the current sequencing cycle.

Images captured at different sequencing cycles and in different image channels are misaligned and have residual registration error with respect to each other. To account for this misalignment, the specialized architecture comprises spatial convolution layers that do not mix information between sequencing cycles and only mix information within a sequencing cycle.

Spatial convolution layers use so-called "segregated convolutions" that operationalize the segregation by independently processing data for each of a plurality of sequencing cycles through a "dedicated, non-shared" sequence of convolutions. The segregated convolutions convolve over data and resulting feature maps of only a given sequencing cycle, i.e., intra-cycle, without convolving over data and resulting feature maps of any other sequencing cycle.

Consider, for example, that the input data comprises (i) current data for a current (time t) sequencing cycle to be base called, (ii) previous data for a previous (time t−1) sequencing cycle, and (iii) next data for a next (time t+1) sequencing cycle. The specialized architecture then initiates three separate data processing pipelines (or convolution pipelines), namely, a current data processing pipeline, a previous data processing pipeline, and a next data processing pipeline. The current data processing pipeline receives as input the current data for the current (time 1) sequencing cycle and independently processes it through a plurality of spatial convolution layers to produce a so-called "current spatially convolved representation" as the output of a final spatial convolution layer. The previous data processing pipeline receives as input the previous data for the previous (time t−1) sequencing cycle and independently processes it through the plurality of spatial convolution layers to produce a so-called "previous spatially convolved representation" as the output of the final spatial convolution layer. The next data processing pipeline receives as input the next data for the next (time t+1) sequencing cycle and independently processes it through the plurality of spatial convolution layers to produce a so-called "next spatially convolved representation" as the output of the final spatial convolution layer.

In some implementations, the current, previous, and next processing pipelines are executed in parallel.

In some implementations, the spatial convolution layers are part of a spatial convolutional network (or subnetwork) within the specialized architecture.

The neural network-based base caller further comprises temporal convolution layers that mix information between sequencing cycles, i.e., inter-cycles. The temporal convolution layers receive their inputs from the spatial convolutional network and operate on the spatially convolved representations produced by the final spatial convolution layer for the respective data processing pipelines.

The inter-cycle operability freedom of the temporal convolution layers emanates from the fact that the misalignment property, which exists in the image data fed as input to the spatial convolutional network, is purged out from the spatially convolved representations by the stack, or cascade, of segregated convolutions performed by the sequence of spatial convolution layers.

Temporal convolution layers use so-called "combinatory convolutions" that groupwise convolve over input channels in successive inputs on a sliding window basis. In one implementation, the successive inputs are successive outputs produced by a previous spatial convolution layer or a previous temporal convolution layer.

In some implementations, the temporal convolution layers are part of a temporal convolutional network (or subnetwork) within the specialized architecture. The temporal convolutional network receives its inputs from the spatial convolutional network. In one implementation, a first temporal convolution layer of the temporal convolutional network groupwise combines the spatially convolved representations between the sequencing cycles. In another implementation, subsequent temporal convolution layers of the temporal convolutional network combine successive outputs of previous temporal convolution layers.

The output of the final temporal convolution layer is fed to an output layer that produces an output. The output is used to base call one or more clusters at one or more sequencing cycles.

During a forward propagation, the specialized architecture processes information from a plurality of inputs in two stages. In the first stage, segregated convolutions are used to prevent mixing of information between the inputs. In the second stage, combinatory convolutions are used to mix information between the inputs. The results from the second stage are used to make a single inference for the plurality of inputs.

This is different than the batch mode technique where a convolution layer processes multiple inputs in a batch at the same time and makes a corresponding inference for each input in the batch. In contrast, the specialized architecture maps the plurality of inputs to the single inference. The single inference can comprise more than one prediction, such as a classification score (e.g., softmax or pre-softmax base-wise classification scores or base-wise regression scores) for each of the four bases (A, C, T, and G).

In one implementation, the inputs have temporal ordering such that each input is generated at a different time step and has a plurality of input channels. For example, the plurality of inputs can include the following three inputs: a current input generated by a current sequencing cycle at time step (t), a previous input generated by a previous sequencing cycle at time step (t−1), and a next input generated by a next sequencing cycle at time step (t+1). In another implementation, each input is respectively derived from the current, previous, and next inputs by one or more previous convolution layers and includes k feature maps.

In one implementation, each input can include the following five input channels: a red image channel (in red), a red distance channel (in yellow), a green image channel (in green), a green distance channel (in purple), and a scaling channel (in blue). In another implementation, each input can include k feature maps produced by a previous convolution layer and each feature map is treated as an input channel.

Figure 18:
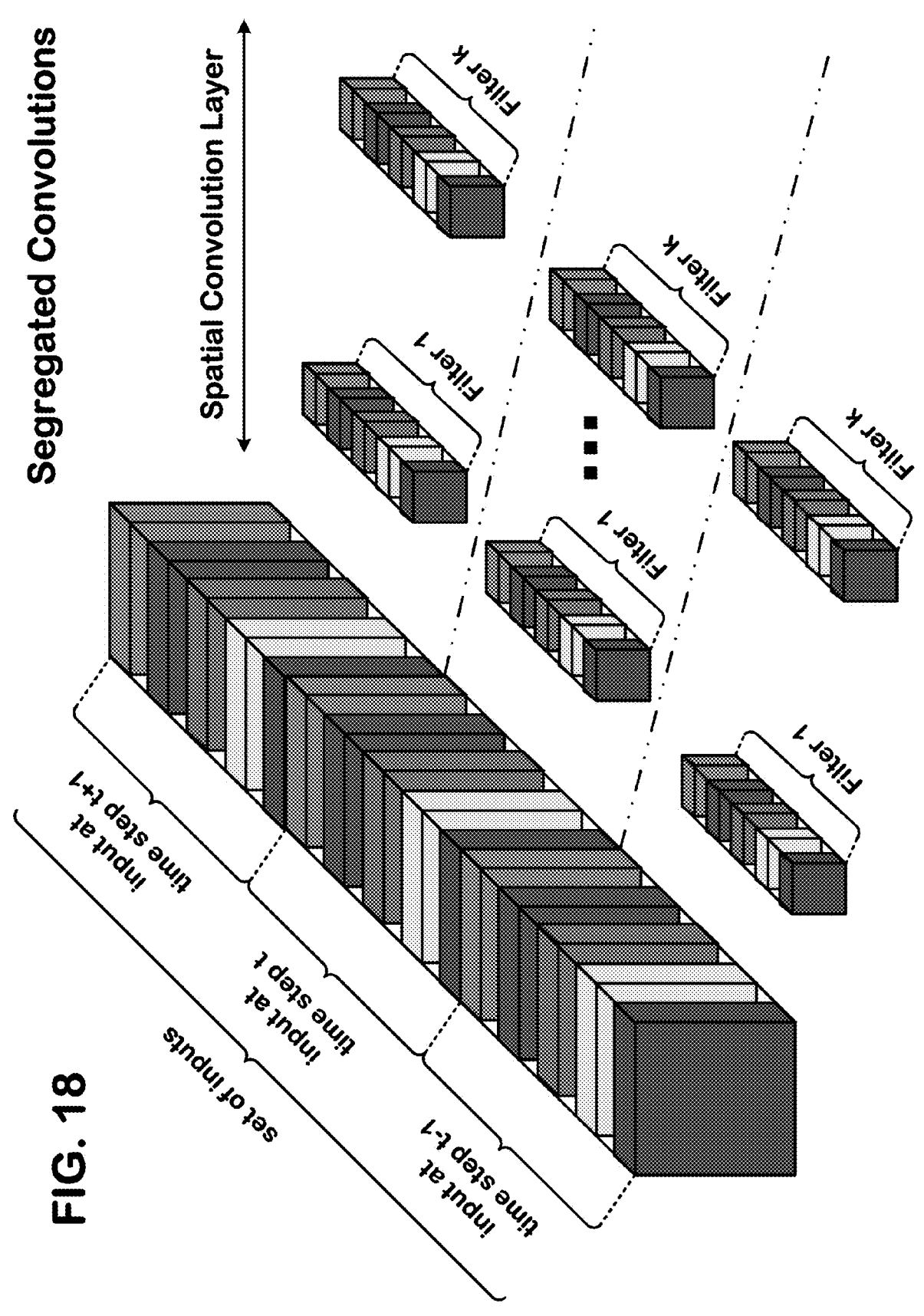
FIG. 18 depicts one implementation of segregated layers, each of which can include convolutions.

FIG. 18 depicts one implementation of segregated layers, each of which can include convolutions. Segregated convolutions process the plurality of inputs at once by applying a convolution filter to each input in parallel. With the segregated convolutions, the convolution filter combines input channels in a same input and does not combine input channels in different inputs. In one implementation, a same convolution filter is applied to each input in parallel. In another implementation, a different convolution filter is applied to each input in parallel. In some implementations, each spatial convolution layer comprises a bank of k convolution filters, each of which applies to each input in parallel.

Figure 19A:
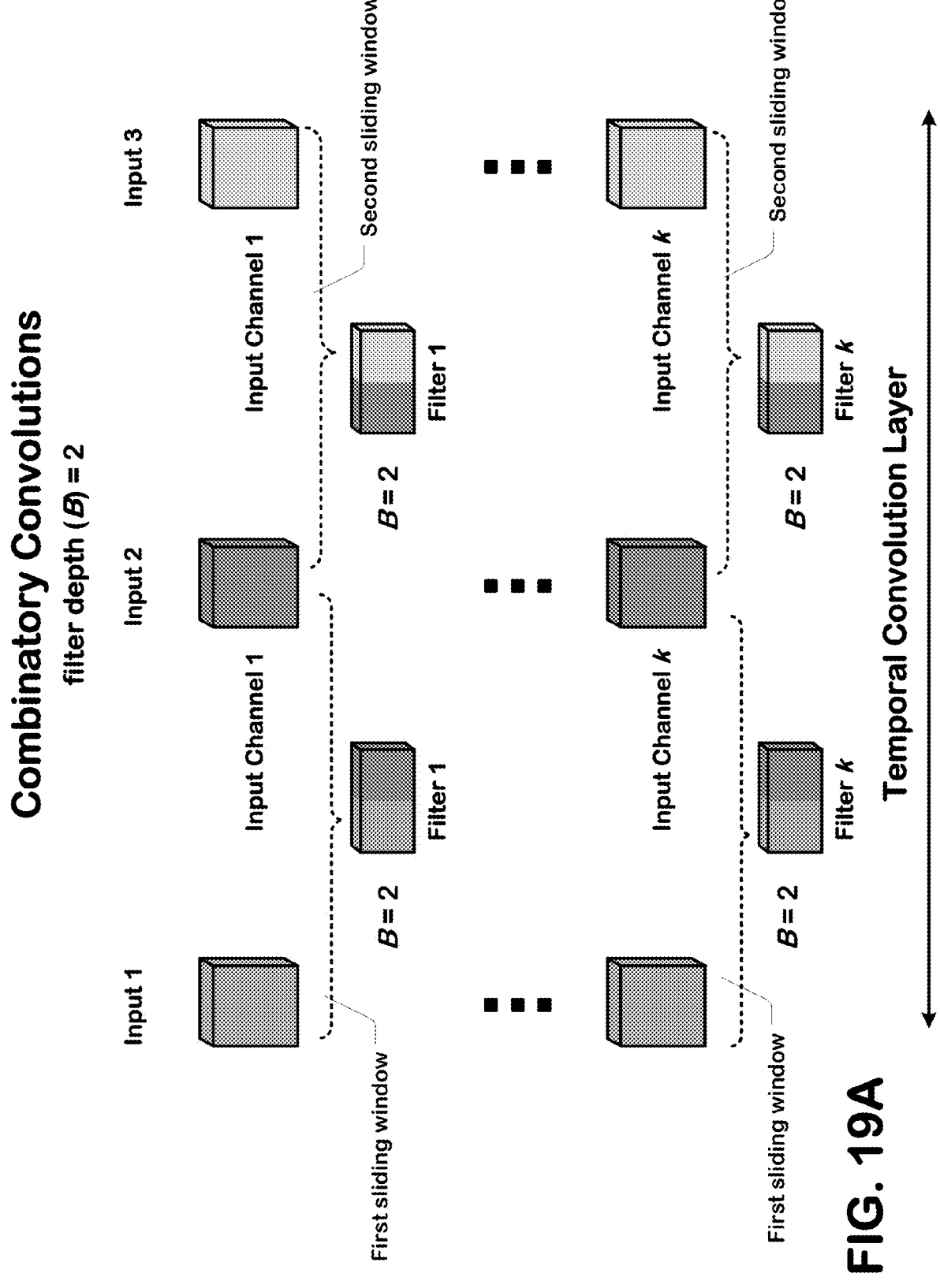
FIG. 19A depicts one implementation of combinatory layers, each of which can include convolutions.
Figure 19B:
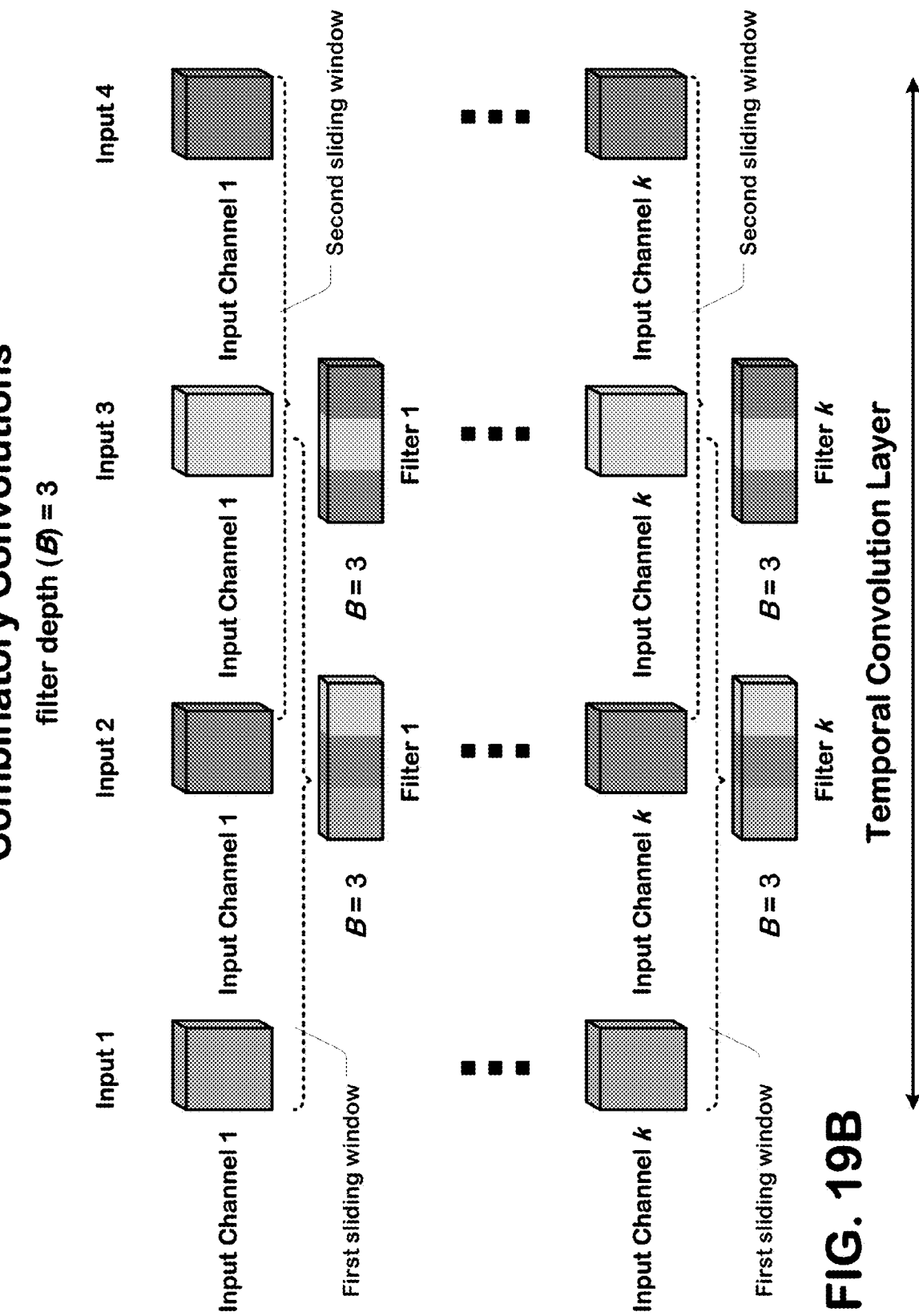
FIG. 19B depicts another implementation of the combinatory layers, each of which can include convolutions.

FIG. 19A depicts one implementation of combinatory layers, each of which can include convolutions. FIG. 19B depicts another implementation of the combinatory layers, each of which can include convolutions. Combinatory convolutions mix information between different inputs by grouping corresponding input channels of the different inputs and applying a convolution filter to each group. The grouping of the corresponding input channels and application of the convolution filter occurs on a sliding window basis. In this context, a window spans two or more successive input channels representing, for instance, outputs for two successive sequencing cycles. Since the window is a sliding window, most input channels are used in two or more windows.

In some implementations, the different inputs originate from an output sequence produced by a preceding spatial or temporal convolution layer. In the output sequence, the different inputs are arranged as successive outputs and therefore viewed by a next temporal convolution layer as successive inputs. Then, in the next temporal convolution layer, the combinatory convolutions apply the convolution filter to groups of corresponding channels in the successive inputs.

In one implementation, the successive inputs have temporal ordering such that a current input is generated by a current sequencing cycle at time step (t), a previous input is generated by a previous sequencing cycle at time step (t−1), and a next input is generated by a next sequencing cycle at time step (t+1). In another implementation, each successive input is respectively derived from the current, previous, and next inputs by one or more previous convolution layers and includes k feature maps.

In one implementation, each input can include the following five input channels: a red image channel (in red), a red distance channel (in yellow), a green image channel (in green), a green distance channel (in purple), and a scaling channel (in blue). In another implementation, each input can include k feature maps produced by a previous convolution layer and each feature map is treated as an input channel.

The depth B of the convolution filter is dependent upon the number of successive inputs whose corresponding input channels are groupwise convolved by the convolution filter on a sliding window basis. In other words, the depth B is equal to the number of successive inputs in each sliding window and the group size.

In FIG. 19A, corresponding input channels from two successive inputs are combined in each sliding window, and therefore B=2. In FIG. 19B, corresponding input channels from three successive inputs are combined in each sliding window, and therefore B=3.

In one implementation, the sliding windows share a same convolution filter. In another implementation, a different convolution filter is used for each sliding window. In some implementations, each temporal convolution layer comprises a bank of k convolution filters, each of which applies to the successive inputs on a sliding window basis.

Figure 20:
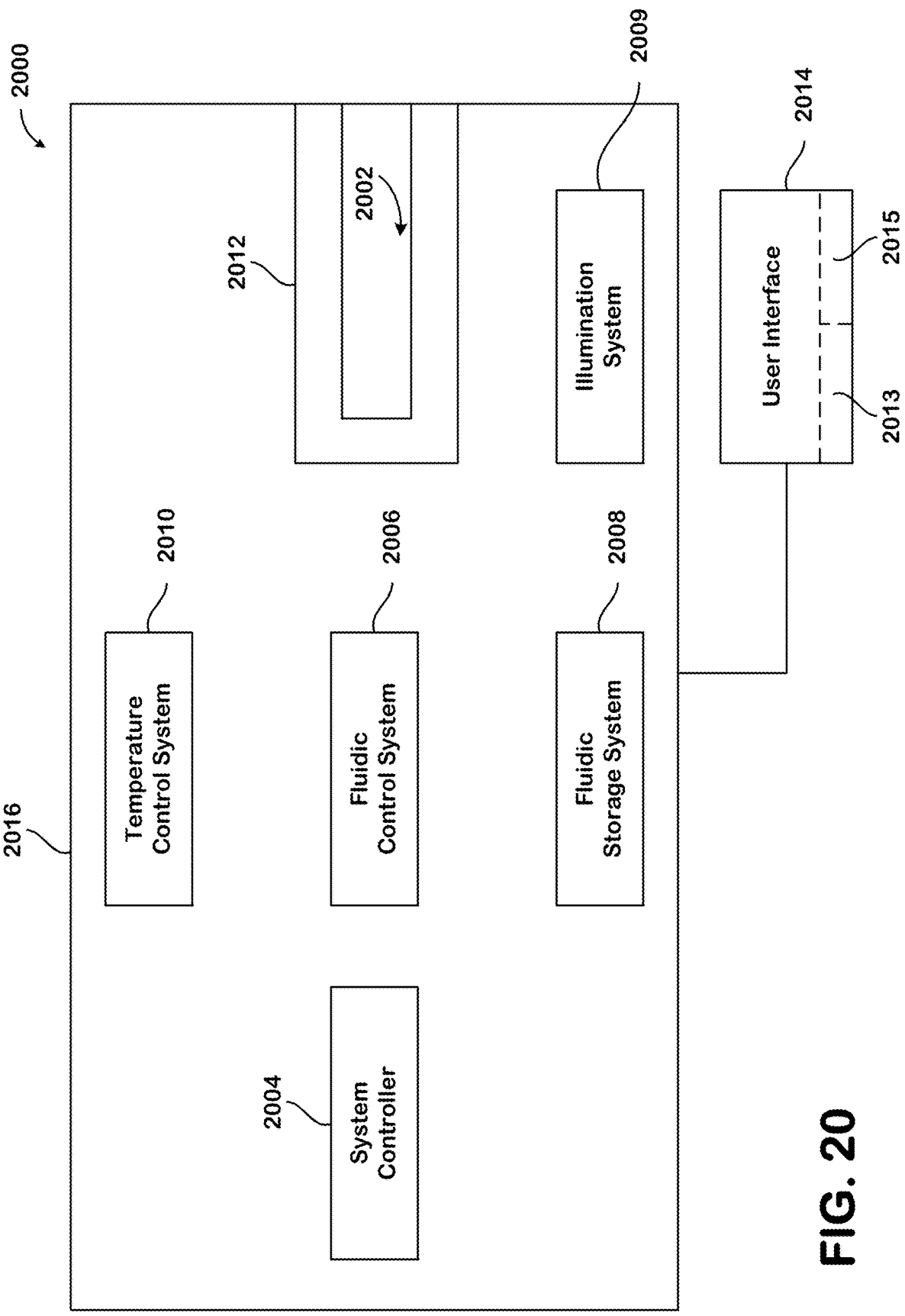
FIG. 20 is a block diagram of a base calling system in accordance with one implementation.

FIG. 20 is a block diagram of a base calling system 2000 in accordance with one implementation. The base calling system 2000 may operate to obtain any information or data that relates to at least one of a biological or chemical substance. In some implementations, the base calling system 2000 is a workstation that may be similar to a bench-top device or desktop computer. For example, a majority (or all)

of the systems and components for conducting the desired reactions can be within a common housing 2016.

In particular implementations, the base calling system 2000 is a nucleic acid sequencing system (or sequencer) configured for various applications, including but not limited to de novo sequencing, resequencing of whole genomes or target genomic regions, and metagenomics. The sequencer may also be used for DNA or RNA analysis. In some implementations, the base calling system 2000 may also be configured to generate reaction sites in a biosensor. For example, the base calling system 2000 may be configured to receive a sample and generate surface attached clusters of clonally amplified nucleic acids derived from the sample. Each cluster may constitute or be part of a reaction site in the biosensor.

The exemplary base calling system 2000 may include a system receptacle or interface 2012 that is configured to interact with a biosensor 2002 to perform desired reactions within the biosensor 2002. In the following description with respect to FIG. 20, the biosensor 2002 is loaded into the system receptacle 2012. However, it is understood that a cartridge that includes the biosensor 2002 may be inserted into the system receptacle 2012 and in some states the cartridge can be removed temporarily or permanently. As described above, the cartridge may include, among other things, fluidic control and fluidic storage components.

In particular implementations, the base calling system 2000 is configured to perform a large number of parallel reactions within the biosensor 2002. The biosensor 2002 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 2002 may include a solid-state imaging device (e.g., CCD or CMOS imager) and a flow cell mounted thereto. The flow cell may include one or more flow channels that receive a solution from the base calling system 2000 and direct the solution toward the reaction sites. Optionally, the biosensor 2002 can be configured to engage a thermal element for transferring thermal energy into or out of the flow channel.

The base calling system 2000 may include various components, assemblies, and systems (or sub-systems) that interact with each other to perform a predetermined method or assay protocol for biological or chemical analysis. For example, the base calling system 2000 includes a system controller 2004 that may communicate with the various components, assemblies, and sub-systems of the base calling system 2000 and also the biosensor 2002. For example, in addition to the system receptacle 2012, the base calling system 2000 may also include a fluidic control system 2006 to control the flow of fluid throughout a fluid network of the base calling system 2000 and the biosensor 2002; a fluid storage system 2008 that is configured to hold all fluids (e.g., gas or liquids) that may be used by the bioassay system; a temperature control system 2010 that may regulate the temperature of the fluid in the fluid network, the fluid storage system 2008, and/or the biosensor 2002; and an illumination system 2009 that is configured to illuminate the biosensor 2002. As described above, if a cartridge having the biosensor 2002 is loaded into the system receptacle 2012, the cartridge may also include fluidic control and fluidic storage components.

Also shown, the base calling system 2000 may include a user interface 2014 that interacts with the user. For example, the user interface 2014 may include a display 2013 to display or request information from a user and a user input device 2015 to receive user inputs. In some implementations, the display 2013 and the user input device 2015 are the same device. For example, the user interface 2014 may include a touch-sensitive display configured to detect the presence of an individual's touch and also identify a location of the touch on the display. However, other user input devices 2015 may be used, such as a mouse, touchpad, keyboard, keypad, handheld scanner, voice-recognition system, motion-recognition system, and the like. As will be discussed in greater detail below, the base calling system 2000 may communicate with various components, including the biosensor 2002 (e.g., in the form of a cartridge), to perform the desired reactions. The base calling system 2000 may also be configured to analyze data obtained from the biosensor to provide a user with desired information.

The system controller 2004 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are exemplary only, and are thus not intended to limit in any way the definition and/or meaning of the term system controller. In the exemplary implementation, the system controller 2004 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the base calling system 2000.

The set of instructions may include various commands that instruct the base calling system 2000 or biosensor 2002 to perform specific operations such as the methods and processes of the various implementations described herein. The set of instructions may be in the form of a software program, which may form part of a tangible, non-transitory computer readable medium or media. As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the base calling system 2000, processed in response to user inputs, or processed in response to a request made by another processing machine (e.g., a remote request through a communication link). In the illustrated implementation, the system controller 2004 includes an analysis module 2138. In other implementations, system controller 2004 does not include the analysis module 2138 and instead has access to the analysis module 2138 (e.g., the analysis module 2138 may be separately hosted on cloud).

The system controller 2004 may be connected to the biosensor 2002 and the other components of the base calling system 2000 via communication links. The system controller 2004 may also be communicatively connected to off-site systems or servers. The communication links may be hardwired, corded, or wireless. The system controller 2004 may receive user inputs or commands, from the user interface 2014 and the user input device 2015.

The fluidic control system 2006 includes a fluid network and is configured to direct and regulate the flow of one or more fluids through the fluid network. The fluid network may be in fluid communication with the biosensor 2002 and the fluid storage system 2008. For example, select fluids may be drawn from the fluid storage system 2008 and directed to the biosensor 2002 in a controlled manner, or the fluids may be drawn from the biosensor 2002 and directed toward, for example, a waste reservoir in the fluid storage system 2008. Although not shown, the fluidic control system 2006 may include flow sensors that detect a flow rate or pressure of the fluids within the fluid network. The sensors may communicate with the system controller 2004.

The temperature control system 2010 is configured to regulate the temperature of fluids at different regions of the fluid network, the fluid storage system 2008, and/or the biosensor 2002. For example, the temperature control system 2010 may include a thermocycler that interfaces with the biosensor 2002 and controls the temperature of the fluid that flows along the reaction sites in the biosensor 2002. The temperature control system 2010 may also regulate the temperature of solid elements or components of the base calling system 2000 or the biosensor 2002. Although not shown, the temperature control system 2010 may include sensors to detect the temperature of the fluid or other components. The sensors may communicate with the system controller 2004.

The fluid storage system 2008 is in fluid communication with the biosensor 2002 and may store various reaction components or reactants that are used to conduct the desired reactions therein. The fluid storage system 2008 may also store fluids for washing or cleaning the fluid network and biosensor 2002 and for diluting the reactants. For example, the fluid storage system 2008 may include various reservoirs to store samples, reagents, enzymes, other biomolecules, buffer solutions, aqueous, and non-polar solutions, and the like. Furthermore, the fluid storage system 2008 may also include waste reservoirs for receiving waste products from the biosensor 2002. In implementations that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 2009 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In implementations that use an illumination system, the illumination system 2009 may be configured to direct an excitation light to reaction sites. As one example, fluorophores may be excited by green wavelengths of light, as such the wavelength of the excitation light may be approximately 532 nm. In one implementation, the illumination system 2009 is configured to produce illumination that is parallel to a surface normal of a surface of the biosensor 2002. In another implementation, the illumination system 2009 is configured to produce illumination that is off-angle relative to the surface normal of the surface of the biosensor 2002. In yet another implementation, the illumination system 2009 is configured to produce illumination that has plural angles, including some parallel illumination and some off-angle illumination.

The system receptacle or interface 2012 is configured to engage the biosensor 2002 in at least one of a mechanical, electrical, and fluidic manner. The system receptacle 2012 may hold the biosensor 2002 in a desired orientation to facilitate the flow of fluid through the biosensor 2002. The system receptacle 2012 may also include electrical contacts that are configured to engage the biosensor 2002 so that the base calling system 2000 may communicate with the biosensor 2002 and/or provide power to the biosensor 2002. Furthermore, the system receptacle 2012 may include fluidic ports (e.g., nozzles) that are configured to engage the biosensor 2002. In some implementations, the biosensor 2002 is removably coupled to the system receptacle 2012 in a mechanical manner, in an electrical manner, and also in a fluidic manner.

In addition, the base calling system 2000 may communicate remotely with other systems or networks or with other bioassay systems 2000. Detection data obtained by the bioassay system(s) 2000 may be stored in a remote database.

Figure 21:
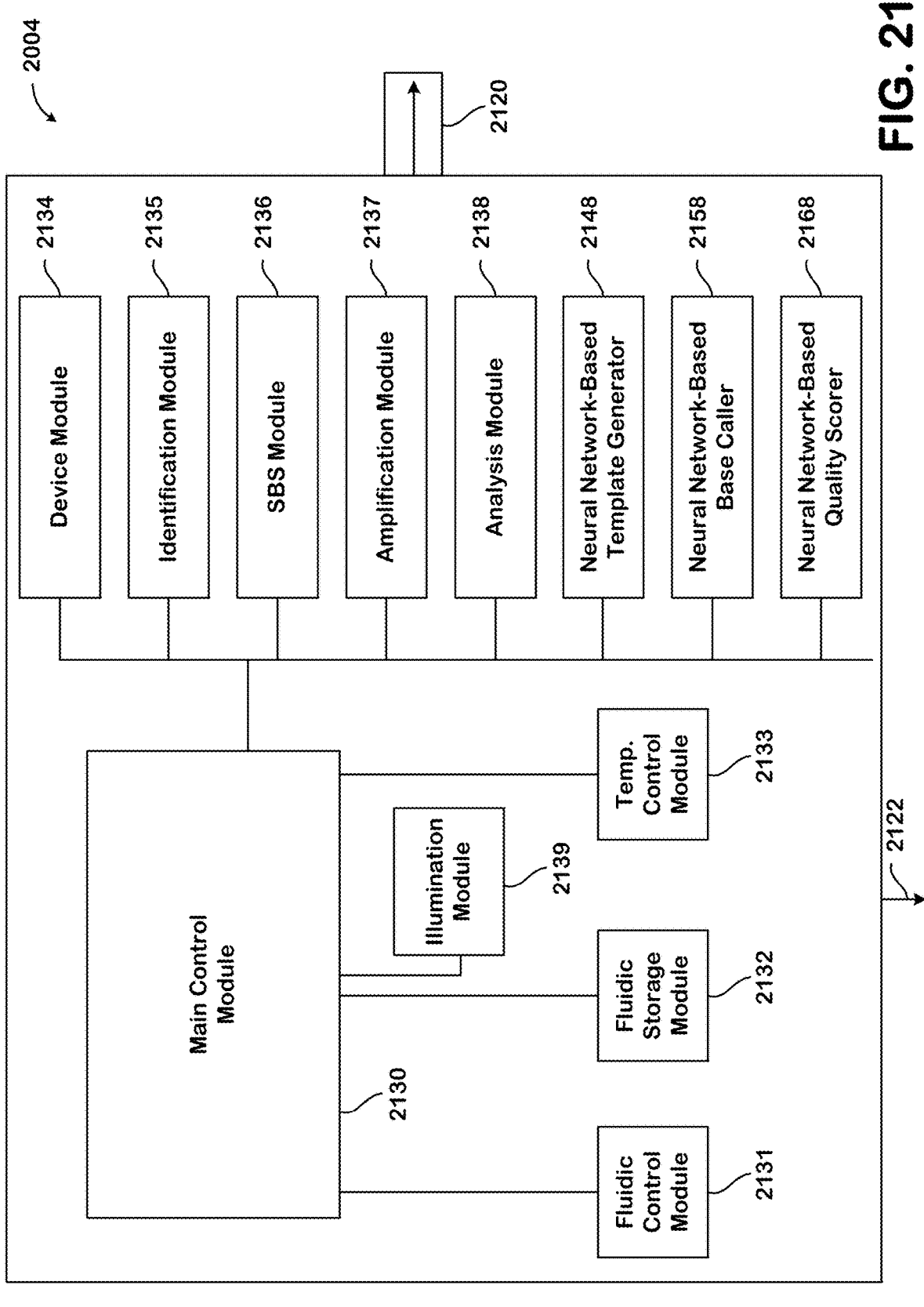
FIG. 21 is a block diagram of a system controller that can be used in the system of FIG. 20.

FIG. 21 is a block diagram of the system controller 2004 that can be used in the system of FIG. 20. In one implementation, the system controller 2004 includes one or more processors or modules that can communicate with one another. Each of the processors or modules may include an algorithm (e.g., instructions stored on a tangible and/or non-transitory computer readable storage medium) or sub-algorithms to perform particular processes. The system controller 2004 is illustrated conceptually as a collection of modules, but may be implemented utilizing any combination of dedicated hardware boards, DSPs, processors, etc. Alternatively, the system controller 2004 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 2120 may transmit information (e.g., commands) to or receive information (e.g., data) from the biosensor 2002 (FIG. 20) and/or the sub-systems 2006, 2008, 2010 (FIG. 20). In implementations, the communication port 2120 may output a plurality of sequences of pixel signals. A communication link 2120 may receive user input from the user interface 2014 (FIG. 20) and transmit data or information to the user interface 2014. Data from the biosensor 2002 or sub-systems 2006, 2008, 2010 may be processed by the system controller 2004 in real-time during a bioassay session. Additionally, or alternatively, data may be stored temporarily in a system memory during a bioassay session and processed in slower than real-time or off-line operation.

As shown in FIG. 21, the system controller 2004 may include a plurality of modules 2131-2139 that communicate with a main control module 2130. The main control module 2130 may communicate with the user interface 2014 (FIG. 20). Although the modules 2131-2139 are shown as communicating directly with the main control module 2130, the modules 2131-2139 may also communicate directly with each other, the user interface 2014, and the biosensor 2002. Also, the modules 2131-2139 may communicate with the main control module 2130 through the other modules.

The plurality of modules 2131-2139 include system modules 2131-2133, 2139 that communicate with the sub-systems 2006, 2008, 2010, and 2009, respectively. The fluidic control module 2131 may communicate with the fluidic control system 2006 to control the valves and flow sensors of the fluid network for controlling the flow of one or more fluids through the fluid network. The fluid storage module 2132 may notify the user when fluids are low or when the waste reservoir is at or near capacity. The fluid storage module 2132 may also communicate with the temperature control module 2133 so that the fluids may be stored at a desired temperature. The illumination module 2139 may communicate with the illumination system 2009 to illuminate the reaction sites at designated times during a protocol, such as after the desired reactions (e.g., binding events) have occurred. In some implementations, the illumination module 2139 may communicate with the illumination system 2009 to illuminate the reaction sites at designated angles.

The plurality of modules 2131-2139 may also include a device module 2134 that communicates with the biosensor 2002 and an identification module 2135 that determines identification information relating to the biosensor 2002. The device module 2134 may, for example, communicate with the system receptacle 2012 to confirm that the biosensor has established an electrical and fluidic connection with the base calling system 2000. The identification module 2135 may receive signals that identify the biosensor 2002. The identification module 2135 may use the identity of the biosensor 2002 to provide other information to the user. For example, the identification module 2135 may determine and then display a lot number, a date of manufacture, or a protocol that is recommended to be run with the biosensor 2002.

The plurality of modules 2131-2139 also includes an analysis module 2138 (also called signal processing module or signal processor) that receives and analyzes the signal data (e.g., image data) from the biosensor 2002. Analysis module 2138 includes memory (e.g., RAM or Flash) to store detection data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 2014 to display desired information to the user. In some implementations, the signal data may be processed by the solid-state imager (e.g., CMOS image sensor) before the analysis module 2138 receives the signal data.

The analysis module 2138 is configured to obtain image data from the light detectors at each of a plurality of sequencing cycles. The image data is derived from the emission signals detected by the light detectors and process the image data for each of the plurality of sequencing cycles through a neural network (e.g., a neural network-based template generator 2148, a neural network-based base caller 2158 (e.g., FIG. 4 and FIG. 10), and/or a neural network-based quality scorer 2168) and produce a base call for at least some of the analytes at each of the plurality of sequencing cycle.

Protocol modules 2136 and 2137 communicate with the main control module 2130 to control the operation of the sub-systems 2006, 2008, and 2010 when conducting predetermined assay protocols. The protocol modules 2136 and 2137 may include sets of instructions for instructing the base calling system 2000 to perform specific operations pursuant to predetermined protocols. As shown, the protocol module may be a sequencing-by-synthesis (SBS) module 2136 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g. as catalyzed by a polymerase enzyme) or ligation (e.g. catalyzed by a ligase enzyme). In a particular polymerase-based SBS implementation, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 2009 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for implementations that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (2008); WO 04/018497; U.S. Pat. No. 7,057,026; WO 91/06678; WO 07/123744; U.S. Pat. Nos. 7,329,492; 7,211,414; 7,315,019; 7,405,281, and US 2008/014708082, each of which is incorporated herein by reference.

For the nucleotide delivery step of an SBS cycle, either a single type of nucleotide can be delivered at a time, or multiple different nucleotide types (e.g., A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one implementation, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some implementations, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in U.S. Pat. App. Ser. Nos. 61/538,294 and 61/619,878, which are incorporated herein by reference in their entireties. U.S. application Ser. No. 13/624,200, which was filed on Sep. 21, 2012, is also incorporated by reference in its entirety.

The plurality of protocol modules may also include a sample-preparation (or generation) module 2137 that is configured to issue commands to the fluidic control system 2006 and the temperature control system 2010 for amplifying a product within the biosensor 2002. For example, the biosensor 2002 may be engaged to the base calling system 2000. The amplification module 2137 may issue instructions to the fluidic control system 2006 to deliver necessary amplification components to reaction chambers within the biosensor 2002. In other implementations, the reaction sites may already contain some components for amplification, such as the template DNA and/or primers. After delivering the amplification components to the reaction chambers, the amplification module 2137 may instruct the temperature control system 2010 to cycle through different temperature stages according to known amplification protocols. In some implementations, the amplification and/or nucleotide incorporation is performed isothermally.

The SBS module 2136 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module

2136 may instruct the fluidic control system 2006 to direct a flow of reagent and enzyme solutions through the biosensor 2002. Exemplary reversible terminator-based SBS methods which can be utilized with the apparatus and methods set forth herein are described in US Patent Application Publication No. 2007/0166705 A1, US Patent Application Publication No. 2006/0188901 A1, U.S. Pat. No. 7,057,026, US Patent Application Publication No. 2006/0240439 A1, US Patent Application Publication No. 2006/02814714709 A1, PCT Publication No. WO 05/065814, US Patent Application Publication No. 2005/014700900 A1, PCT Publication No. WO 06/064199 and PCT Publication No. WO 07/01470251, each of which is incorporated herein by reference in its entirety. Exemplary reagents for reversible terminator-based SBS are described in U.S. Pat. Nos. 7,541,444; 7,057,026; 7,414,14716; U.S. Pat. Nos. 7,427,673; 7,566,537; 7,592, 435 and WO 07/14835368, each of which is incorporated herein by reference in its entirety.

In some implementations, the amplification and SBS modules may operate in a single assay protocol where, for example, template nucleic acid is amplified and subsequently sequenced within the same cartridge.

The base calling system 2000 may also allow the user to reconfigure an assay protocol. For example, the base calling system 2000 may offer options to the user through the user interface 2014 for modifying the determined protocol. For example, if it is determined that the biosensor 2002 is to be used for amplification, the base calling system 2000 may request a temperature for the annealing cycle. Furthermore, the base calling system 2000 may issue warnings to a user if a user has provided user inputs that are generally not acceptable for the selected assay protocol.

In implementations, the biosensor 2002 includes millions of sensors (or pixels), each of which generates a plurality of sequences of pixel signals over successive base calling cycles. The analysis module 2138 detects the plurality of sequences of pixel signals and attributes them to corresponding sensors (or pixels) in accordance to the row-wise and/or column-wise location of the sensors on an array of sensors.

Each sensor in the array of sensors can produce sensor data for a tile of the flow cell, where a tile in an area on the flow cell at which clusters of genetic material are disposed during the based calling operation. The sensor data can comprise image data in an array of pixels. For a given cycle, the sensor data can include more than one image, producing multiple features per pixel as the tile data.

"Logic" (e.g., data flow logic), as used herein, can be implemented in the form of a computer product including a non-transitory computer readable storage medium with computer usable program code for performing the method steps described herein. The "logic" can be implemented in the form of an apparatus including a memory and at least one processor that is coupled to the memory and operative to perform exemplary method steps. The "logic" can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media). In one implementation, the logic implements a data processing function. The logic can be a general purpose, single core or multicore, processor with a computer program specifying the function, a digital signal processor with a computer program, configurable logic such as an FPGA with a configuration file, a special purpose circuit such as a state machine, or any combination of these. Also, a computer program product can embody the computer program and configuration file portions of the logic.

Figure 22:
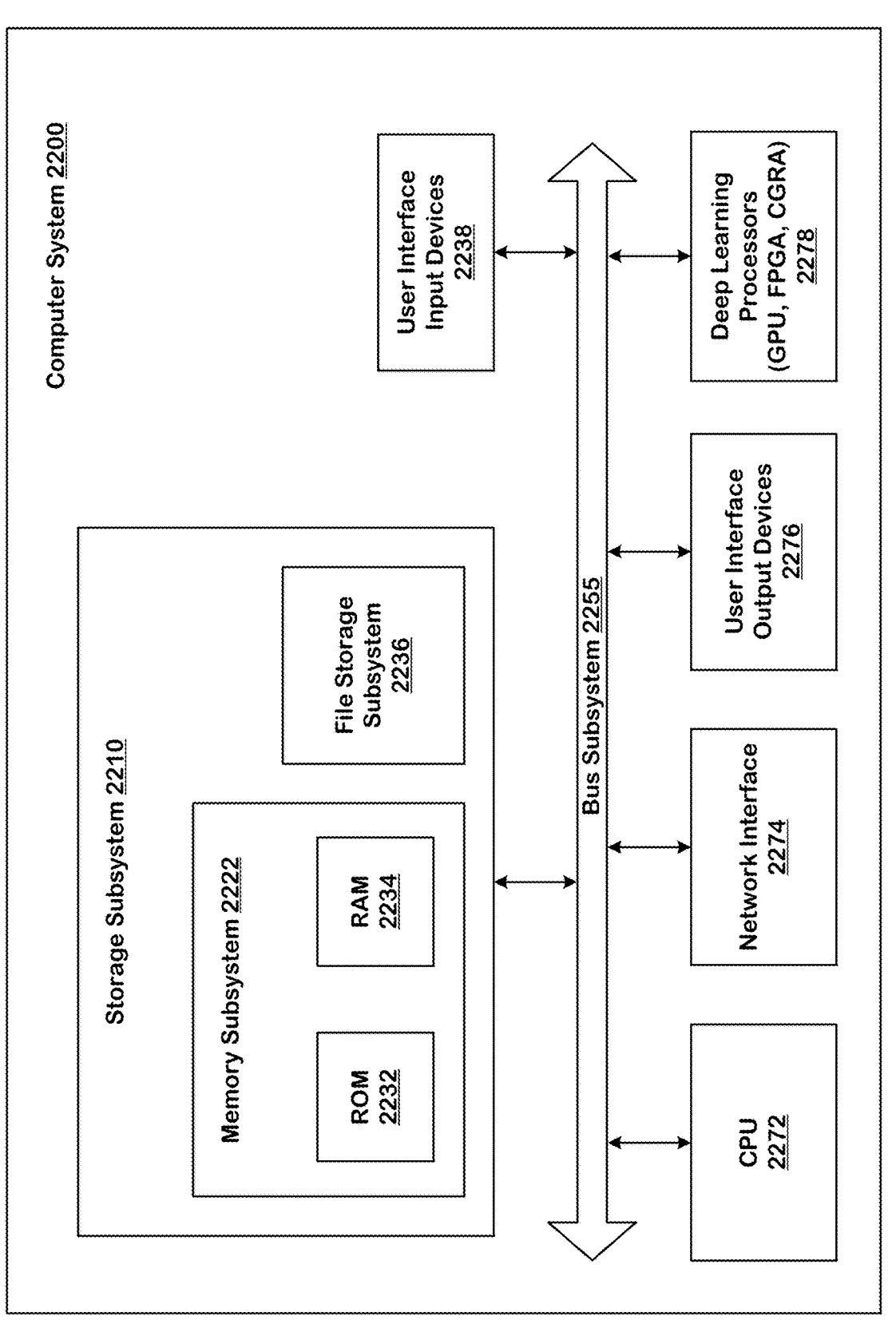
FIG. 22 is a simplified block diagram of a computer system that can be used to implement the technology disclosed.

FIG. 22 is a simplified block diagram of a computer 2200 system that can be used to implement the technology disclosed. Computer system 2200 includes at least one central processing unit (CPU) 2272 that communicates with a number of peripheral devices via bus subsystem 2255. These peripheral devices can include a storage subsystem 2210 including, for example, memory devices and a file storage subsystem 2236, user interface input devices 2238, user interface output devices 2276, and a network interface subsystem 2274. The input and output devices allow user interaction with computer system 2200. Network interface subsystem 2274 provides an interface to outside networks, including an interface to corresponding interface devices in other computer systems.

User interface input devices 2238 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2200.

User interface output devices 2276 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2200 to the user or to another machine or computer system.

Storage subsystem 2210 stores programming and data constructs that provide the functionality of some or all of the modules and methods described herein. These software modules are generally executed by deep learning processors 2278.

In one implementation, the neural networks are implemented using deep learning processors 2278 can be configurable and reconfigurable processors, field-programmable gate arrays (FPGAs), application-specific integrated circuits (ASICs), and/or coarse-grained reconfigurable architectures (CGRAs) and graphics processing units (GPUs) other configured devices. Deep learning processors 2278 can be hosted by a deep learning cloud platform such as Google Cloud Platform™, Xilinx™, and Cirrascale™ Examples of deep learning processors 14978 include Google's Tensor Processing Unit (TPU)™, rackmount solutions like GX4 Rackmount Series™, GX149 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, and others.

Memory subsystem 2222 used in the storage subsystem 2210 can include a number of memories including a main random access memory (RAM) 2232 for storage of instructions and data during program execution and a read only memory (ROM) 2234 in which fixed instructions are stored. A file storage subsystem 2236 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2236 in the storage subsystem 2210, or in other machines accessible by the processor.

Bus subsystem 2255 provides a mechanism for letting the various components and subsystems of computer system 2200 communicate with each other as intended. Although bus subsystem 2255 is shown schematically as a single bus, alternative implementations of the bus subsystem can use multiple busses.

Computer system 2200 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 2200 depicted in FIG. 22 is intended only as a specific example for purposes of illustrating the preferred implementations of the present invention. Many other configurations of computer system 2200 are possible having more or less components than the computer system depicted in FIG. 22.

CLAUSES

1. A system for analysis of base call sensor output, comprising:
    a host processor;
    memory accessible by the host processor storing tile data including arrays of sensor data for tiles from sensing cycles of a base calling operation; and
    a neural network processor having access to the memory, the neural network processor including:
        a plurality of execution clusters, the execution clusters in the plurality of execution clusters configured to execute a neural network; and
        data flow logic having access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

2. The system of clause 1, including logic to assemble the output patches from the plurality of execution clusters to provide base call classification data for the subject cycle, and to store the base call classification data in memory.

3. The system of clause 1, wherein an execution cluster in the plurality of execution clusters comprises a set of computation engines having plural members, configured to convolve trained parameters over input data for multiple layers of the neural network, wherein input data for a first layer is from the input unit, and the data for subsequent layers is from activation data output from a previous layer.

4. The system of clause 3, including memory storing plural versions of trained parameters for the neural network, and wherein clusters in the plurality of clusters in the neural network processor are configured to include kernel memory to store the trained parameters, and the data flow logic is configured to provide instances of trained parameters to the kernel memory of execution clusters in the plurality of execution clusters for use in execution of the neural network.

5. The system of clause 4, wherein the instances of trained parameters are applied as a function of cycle number in the sensing cycles of the base calling operation.

6. The system of clause 1, wherein an execution cluster in the plurality of execution clusters comprises a set of computation engines having plural members, the set of computation engines configured to apply a plurality of configurable filters for corresponding layers of the neural network to sub-patches from the input unit, and to sub-patches from activation data output from a layer of the neural network.

7. The system of clause 1, wherein the neural network executes for each spatially aligned patch of an input unit, a segregated stack of spatial layers, and provides data from the N spatially aligned patches output from the segregated stacks to one or more combinatorial layers.

8. The system of clause 7, wherein an execution cluster in the plurality of execution clusters is configured to execute N segregated stacks of spatial layers using sensor data of the N spatially aligned patches input to produce an output patch of classification data for the spatially aligned patch of the subject sensing cycle.

9. The system of clause 7, wherein an execution cluster in the plurality of execution clusters is configured to execute a segregated stack of spatial layers using sensor data of a current spatially aligned patch, to feedback intermediate data for the spatially aligned patch to the memory for use as tile data in input units for other cycles, and to provide the intermediate data from previous cycles and an output of the segregated stack for the current cycle to the one or more combinatorial layers to produce the output patch of the subject sensing cycle. In one implementation, the memory is on-chip or off-chip DRAM or on-chip memory like SRAM or BRAM, and the processing units of a processor execute the neural network. In such implementations, the intermediate data from previous cycles is sent from the memory to the on-chip processing elements (e.g., via DMA engines) for processing by, for example, by the combinatorial layers that are being executed by the chip as part of the neural network execution on the chip/processor.

10. The system of clause 1, wherein the number N is an integer equal to 5 or greater.

11. The system of clause 1, wherein logic circuits are configured to load input units in a sequence traversing the arrays of tile data for a plurality of sensing cycles, including writing a next input unit in the sequence to the neural network processor for an execution cluster during execution of the neural network by the execution cluster for a previous input unit.

12. The system of clause 1, including logic in the host processor to execute an activation function over the output patches.

13. The system of clause 1, including logic in the host processor to execute a softmax function over the output patches.

14. The system of clause 1, wherein the arrays of tile data include M features, where M is greater than one.

15. The system of clause 7, including a tile cluster mask stored in the memory for the tiles of a base calling operation, and the execution clusters are configured to remove data from intermediate data from at least one of the layers using the tile cluster mask.

16. A computer-implemented method for analysis of base call sensor output, comprising:

storing tile data in memory including arrays of sensor data for tiles from sensing cycles of a base calling operation; and executing a neural network over the tile data using a plurality of execution clusters, including:

providing input units of tile data to available execution clusters in the plurality of execution clusters, the input units including a number N of spatially aligned patches of arrays of tile data from respective sensing cycles, including a subject sensing cycle, and causing the execution clusters to apply the N spatially aligned patches to the neural network to produce output patches of classification data for the spatially aligned patch of the subject sensing cycle, where N is greater than 1.

17. The computer-implemented method of clause 16, including assembling the output patches from the plurality of execution clusters to provide base call classification data for the subject cycle, and storing the base call classification data in memory.

18. The computer-implemented method of clause 16, wherein an execution cluster in the plurality of execution clusters comprises a set of computation engines having plural members, configured to convolve trained parameters over input data for multiple layers of the neural network, wherein input data for a first layer is from the input unit, and the data for subsequent layers is from activation data output from a previous layer.

19. The computer-implemented method of clause 18, including storing plural versions of trained parameters for the neural network, and wherein clusters in the plurality of execution clusters in the neural network processor are configured to include kernel memory to store the trained parameters, and providing instances of trained parameters to the kernel memory of execution clusters in the plurality of execution clusters for use in execution of the neural network.

20. The computer-implemented method of clause 19, including applying the instances of trained parameters as a function of cycle number in the sensing cycles of the base calling operation.

21. The computer-implemented method of clause 16, wherein an execution cluster in the plurality of execution clusters comprises a set of computation engines having plural members, the set of computation engines configured to apply a plurality of configurable filters for corresponding layers of the neural network to sub-patches from the input unit, and to sub-patches from activation data output from a layer of the neural network.

22. The computer-implemented method of clause 16, wherein the neural network includes for each spatially aligned patch of an input unit, a segregated stack of spatial layers, and provides data from the N spatially aligned patches output from the segregated stacks to one or more combinatorial layers.

23. The computer-implemented method of clause 22, wherein an execution cluster in the plurality of execution clusters is configured to execute N segregated stacks of spatial layers using sensor data of the N spatially aligned patches input to produce an output patch of classification data for the spatially aligned patch of the subject sensing cycle.

24. The computer-implemented method of clause 22, wherein an execution cluster in the plurality of execution clusters is configured to execute a segregated stack of spatial layers using sensor data of a current spatially aligned patch, to feedback intermediate data for the spatially aligned patch to the memory for use as tile data in input units for other cycles, and to provide the intermediate data from previous cycles and an output of the segregated stack for the current cycle to the one or more combinatorial layers to produce the output patch of the subject sensing cycle.

25. The computer-implemented method of clause 16, wherein the number N is an integer equal to 5 or greater.

26. The computer-implemented method of clause 16, including loading input units in a sequence traversing the arrays of tile data for a plurality of sensing cycles, including writing a next input unit in the sequence to an execution cluster during execution of the neural network by the execution cluster for a previous input unit.

27. The computer-implemented method of clause 16, including executing an activation function over the output patches.

28. The computer-implemented method of clause 16, including executing a softmax function over the output patches.

29. The computer-implemented method of clause 16, wherein the arrays of tile data include M features, where M is greater than one.

30. The computer-implemented method of clause 16, including storing a tile cluster mask stored in the memory for the tiles of a base calling operation, and removing data from the intermediate data from at least one of the layers using the tile cluster mask.

31. A system for analysis of base call sensor output, comprising:

memory accessible by the runtime program storing tile data including sensor data for a tile from sensing cycles of a base calling operation;

a neural network processor having access to the memory, the neural network processor configured to execute runs of a neural network using trained parameters to produce classification data for sensing cycles, a run of the neural network operating on a sequence of N arrays of tile data from respective sensing cycles of N sensing cycles, including a subject cycle, to produce the classification data for the subject cycle; and data flow logic to move tile data and the trained parameters from the memory to the neural network processor for runs of the neural network using input units including data for spatially aligned patches of the N arrays from respective sensing cycles of N sensing cycles.

32. The system of clause 31, wherein the tile data for a sensing cycle in the memory includes one or both of sensor data for the sensing cycle and intermediate data fed back from the neural network for the sensing cycle.

33. The system of clause 31, wherein the memory stores a tile cluster mask identifying elements of the arrays of sensor data that represent locations of flow cell clusters in the tile, and the neural network processor including mask logic to apply the tile cluster mask to intermediate data in the neural network.

34. The system of clause 31, the data flow logic comprising elements of the neural network processor configured using configuration data.

35. The system of clause 31, including a host processing system including a runtime program, and the data flow logic including logic for coordination of the runs with the runtime program on the host.

36. The system of clause 31, including a host processing system including a runtime program, logic of the runtime program providing the tile data from the sensing cycles and the trained parameters for the neural network to the memory.

37. The system of clause 31, wherein the tile data for a sensing cycle in the memory includes one or both of sensor data for the sensing cycle and intermediate data fed back from the neural network for the sensing cycle.

38. The system of clause 31, wherein the sensor data of a sensing cycle includes data representing signals for detection of one base per flow cell cluster.

39. The system of clause 31, wherein the neural network processor is configured to form a plurality of execution clusters, the execution logic clusters in the plurality of execution clusters running the neural network over spatially aligned patches of the tile data; and wherein the data flow logic has access to the memory and to execution clusters in the plurality of execution clusters, to provide input units of tile data to available execution clusters in the plurality of execution clusters, and to cause the execution clusters to apply tile data of the N spatially aligned patches of the input units to the neural network to produce output patches of classification data for the subject cycle.

40. The system of clause 39, including logic to assemble the output patches from the plurality of execution clusters to provide base call classification data for the subject cycle, and to store the base call classification data in memory.

41. The system of clause 39, wherein an execution cluster in the plurality of execution clusters comprises a set of computation engines having plural members, configured to convolve trained parameters over input data for multiple layers of the neural network, wherein input data for a first layer is from the input unit, and the data for subsequent layers is from activation data output from a previous layer.

42. The system of clause 41, including memory storing plural versions of trained parameters for the neural network, and wherein clusters in the plurality of clusters in the neural network processor are configured to include kernel memory to store the trained parameters, and the data flow logic is configured to provide instances of trained parameters to the kernel memory of execution clusters in the plurality of execution clusters for use in execution of the neural network.

43. The system of clause 42, wherein the instances of trained parameters are applied as a function of cycle number in the sensing cycles of the base calling operation.

44. The system of clause 39, wherein an execution cluster in the plurality of execution clusters comprises a set of computation engines having plural members, the set of computation engines configured to apply a plurality of configurable filters for corresponding layers of the neural network to sub-patches from the input unit, and to sub-patches from activation data output from a layer of the neural network.

45. The system of clause 39, wherein an execution cluster in the plurality of execution clusters is configured to execute a segregated stack of spatial layers using sensor data of a current spatially aligned patch, to feedback intermediate data for the spatially aligned patch to the memory for use as tile data in other input units, and to provide the intermediate data from previous cycles and an output of the segregated stack for the current cycle to the one or more combinatorial layers to produce the output patch of the subject sensing cycle.

46. The system of clause 31, wherein the number N is an integer equal to 5 or greater.

47. The system of clause 31, wherein the logic circuits are configured to load input units in a sequence traversing the arrays of tile data for a plurality of sensing cycles, including writing a next input unit in the sequence to the neural network processor for an execution cluster during execution of the neural network by the execution cluster for a previous input unit.

48. The system of clause 31, including logic in the host processor to execute an activation function over the output patches.

49. The system of clause 31, including logic in the host processor to execution a softmax function over the output patches.

50. The system of clause 31, wherein the arrays of tile data include M features, where Mis greater than one.

51. The system of any of the preceding clauses in which the neural network processor is a reconfigurable processor.

52. The system of any of the preceding clauses in which the neural network processor is a configurable processor.

53. A computer-implemented method for analysis of base call sensor output, comprising: storing tile data in memory including sensor data for a tile from sensing cycles of a base calling operation;

executing runs of a neural network using trained parameters to produce classification data for sensing cycles, a run of the neural network operating on a sequence of N arrays of tile data from respective sensing cycles of N sensing cycles, including a subject cycle, to produce the classification data for the subject cycle; and moving tile data and the trained parameters from memory to the neural network for runs of the neural network using input units including data for spatially aligned patches of the N arrays from respective sensing cycles of N sensing cycles.

54. The computer-implemented method of clause 53, wherein the tile data for a sensing cycle in the memory includes one or both of sensor data for the sensing cycle and intermediate data fed back from the neural network for the sensing cycle.

55. The computer-implemented method of clause 53, including storing a tile cluster mask identifying elements of the arrays of sensor data that represent locations of flow cell clusters in the tile, and applying the tile cluster mask to intermediate data in the neural network.

56. The computer-implemented method of clause 53, the data flow logic comprising elements of the neural network processor configured using configuration data.

57. The computer-implemented method of clause 53, wherein the tile data for a sensing cycle in the memory includes one or both of sensor data for the sensing cycle and intermediate data fed back from the neural network for the sensing cycle.

58. The computer-implemented method of clause 53, wherein the sensor data of a sensing cycle includes data representing signals for detection of one base per flow cell cluster.

59. The computer-implemented method of clause 53, including using a plurality of execution clusters running the neural network over spatially aligned patches of the tile data; and providing input units of tile data to available execution clusters in the plurality of execution clusters, and causing the execution clusters to apply tile data of the N spatially aligned patches of the input units to the neural network to produce output patches of classification data for the subject cycle.

60. The computer-implemented method of clause 59, including assembling the output patches from the plurality of execution clusters to provide base call classification data for the subject cycle, and storing the base call classification data in memory.

61. The computer-implemented method of clause 59, wherein an execution cluster in the plurality of execution clusters comprises a set of computation engines having plural members, configured to convolve trained parameters over input data for multiple layers of the neural network, wherein input data for a first layer is from the input unit, and the data for subsequent layers is from activation data output from a previous layer.

62. The computer-implemented method of clause 61, including storing plural versions of trained parameters for the neural network, and wherein clusters in the plurality of clusters in the neural network processor are configured to include kernel memory to store the trained parameters, and providing instances of trained parameters to the kernel memory of execution clusters in the plurality of execution clusters for use in execution of the neural network.

63. The computer-implemented method of clause 62, wherein the instances of trained parameters are applied as a function of cycle number in the sensing cycles of the base calling operation.

64. The computer-implemented method of clause 59, wherein an execution cluster in the plurality of execution clusters comprises a set of computation engines having plural members, the set of computation engines configured to apply a plurality of configurable filters for corresponding layers of the neural network to sub-patches from the input unit, and to sub-patches from activation data output from a layer of the neural network.

65. The computer-implemented method of clause 59, wherein an execution cluster in the plurality of execution clusters is configured to execute a segregated stack of spatial layers using sensor data of a current spatially aligned patch, to feedback intermediate data for the spatially aligned patch to the memory for use as tile data in other input units, and to provide the intermediate data from previous cycles and an output of the segregated stack for the current cycle to the one or more combinatorial layers to produce the output patch of the subject sensing cycle.

66. The computer-implemented method of clause 53, wherein the number N is an integer equal to 5 or greater.

67. The computer-implemented method of clause 53, including loading input units in a sequence traversing the arrays of tile data for a plurality of sensing cycles, including writing a next input unit in the sequence to the neural network during execution of the neural network for a previous input unit.

68. The computer-implemented method of clause 53, wherein the arrays of tile data include M features, where M is greater than one.

69 The computer-implemented method of any of the preceding computer-implemented method clauses including configuring a configurable processor to execute the neural network.

70. The computer-implemented method of any of the preceding computer-implemented method clauses including configuring a reconfigurable processor to execute the neural network.

We claim as follows:

1. A system for analysis of base call sensor output, comprising:
   a host processor;
   memory accessible by the host processor storing tile data including arrays of sensor data for tiles from sensing cycles of a base calling operation, wherein the sensor data comprises pixel arrays from images of clusters of nucleic acids captured by a light detector of a sequencer; and
   a neural network processor having access to the memory, the neural network processor including:

a plurality of execution clusters, the execution clusters in the plurality of execution clusters configured to execute a neural network; and
   data flow logic having access to the memory and to execution clusters in the plurality of execution clusters to:
   provide input units of tile data comprising the pixel arrays to available execution clusters in the plurality of execution clusters, the input units including N spatially aligned patches of the pixel arrays from tile data from respective sensing cycles, including a subject sensing cycle;
   cause the execution clusters to apply the N spatially aligned patches to the neural network;
   identify locations of clusters of nucleic acids depicted by the images of clusters of nucleic acids;
   based on the identified locations of clusters of nucleic acids depicted by the images of clusters of nucleic acids, remove data for a subset of the clusters of nucleic acids from intermediate data; and
   produce, utilizing the neural network, output patches of classification data for a spatially aligned patch for the subject sensing cycle based on the intermediate data, where N is greater than 1.

2. The system of claim 1, including logic to assemble the output patches from the plurality of execution clusters to provide base call classification data for the subject sensing cycle, and to store the base call classification data in memory.

3. The system of claim 1, wherein an execution cluster in the plurality of execution clusters comprises a set of computation engines having plural members, configured to convolve trained parameters over input data for multiple layers of the neural network, wherein input data for a first layer is from an input unit, and data for subsequent layers is from activation data output from a previous layer.

4. The system of claim 3, including memory storing plural versions of trained parameters for the neural network, and wherein clusters in the plurality of execution clusters in the neural network processor are configured to include kernel memory to store the trained parameters, and the data flow logic is configured to provide instances of trained parameters to the kernel memory of execution clusters in the plurality of execution clusters for use in execution of the neural network.

5. The system of claim 4, wherein the instances of trained parameters are applied as a function of cycle number in the sensing cycles of the base calling operation.

6. The system of claim 1, wherein an execution cluster in the plurality of execution clusters comprises a set of computation engines having plural members, the set of computation engines configured to apply a plurality of configurable filters for corresponding layers of the neural network to sub-patches from an input unit, and to sub-patches from activation data output from a layer of the neural network.

7. The system of claim 1, wherein the neural network executes for each spatially aligned patch of an input unit, a segregated stack of spatial layers, and provides data from the N spatially aligned patches output from the segregated stacks of spatial layers to one or more combinatorial layers.

8. The system of claim 7, wherein an execution cluster in the plurality of execution clusters is configured to execute N segregated stacks of spatial layers using sensor data of the N spatially aligned patches input to produce an output patch of classification data for the spatially aligned patch for the subject sensing cycle.

9. The system of claim 7, wherein an execution cluster in the plurality of execution clusters is configured to execute a segregated stack of spatial layers using sensor data of a current spatially aligned patch, to feedback intermediate data for the current spatially aligned patch to the memory for use as tile data in input units for other cycles, and to provide the intermediate data from previous cycles and an output of the segregated stack of spatial layers for a current sensing cycle to the one or more combinatorial layers to produce an output patch for the subject sensing cycle.

10. The system of claim 7, including a tile cluster mask stored in the memory for the tiles of a base calling operation, and the execution clusters are configured to remove data from intermediate data from at least one of the spatial layers of the segregated stacks of spatial layers using the tile cluster mask.

11. The system of claim 1, wherein N is an integer equal to 5 or greater.

12. The system of claim 1, wherein logic circuits are configured to load input units in a sequence traversing the arrays of tile data for a plurality of sensing cycles, including writing a next input unit in the sequence to the neural network processor for an execution cluster during execution of the neural network by the execution cluster for a previous input unit.

13. The system of claim 1, including logic in the host processor to execute an activation function over the output patches.

14. The system of claim 1, wherein the execution clusters are configured to remove the data for the subset of the clusters of nucleic acids by removing data for the subset of the clusters of nucleic acids from intermediate data processed by at least one layer of the neural network.

15. The system of claim 1, wherein the arrays of tile data include M features, where M is greater than one.

16. A computer-implemented method for analysis of base call sensor output, comprising:

storing tile data in memory including arrays of sensor data for tiles from sensing cycles of a base calling operation, wherein the sensor data comprises pixel arrays from images of clusters of nucleic acids captured by a light detector of a sequencer; and executing a neural network over the tile data using a plurality of execution clusters, including:

providing input units of tile data comprising the pixel arrays to available execution clusters in the plurality of execution clusters, the input units including N spatially aligned patches of the pixel arrays from tile data from respective sensing cycles, including a subject sensing cycle;

causing the execution clusters to apply the N spatially aligned patches of the pixel arrays to the neural network;

identifying locations of clusters of nucleic acids depicted by the images of clusters of nucleic acids;

based on the identified locations of clusters of nucleic acids depicted by the images of clusters of nucleic acids, removing data for a subset of the clusters of nucleic acids from intermediate data; and producing, utilizing the neural network, output patches of classification data for a spatially aligned patch for the subject sensing cycle based on the intermediate data, where N is greater than 1.

17. The computer-implemented method of claim 16, including assembling the output patches from the plurality of execution clusters to provide base call classification data for the subject sensing cycle, and storing the base call classification data in memory.

18. The computer-implemented method of claim 16, wherein an execution cluster in the plurality of execution clusters comprises a set of computation engines having plural members, configured to convolve trained parameters over input data for multiple layers of the neural network, wherein input data for a first layer is from an input unit, and data for subsequent layers is from activation data output from a previous layer.

19. The computer-implemented method of claim 18, including storing plural versions of trained parameters for the neural network, and wherein clusters in the plurality of execution clusters are configured to include kernel memory to store the trained parameters, and providing instances of trained parameters to the kernel memory of execution clusters in the plurality of execution clusters for use in execution of the neural network.

20. A non-transitory computer-readable medium storing instructions that, when executed by at least one processor, cause a computing device to:

store tile data in memory including sensor data for a tile from sensing cycles of a base calling operation, wherein the sensor data comprises pixel arrays from images of clusters of nucleic acids captured by a light detector of a sequencer; and execute a neural network over the tile data using a plurality of execution clusters, including:

providing input units of tile data comprising the pixel arrays to available execution clusters in the plurality of execution clusters, the input units including N spatially aligned patches of the pixel arrays from tile data from respective sensing cycles, including a subject sensing cycle;

causing the execution clusters to apply the N spatially aligned patches of the pixel arrays to the neural network;

identifying locations of clusters of nucleic acids depicted by the images of clusters of nucleic acids;

based on the identified locations of clusters of nucleic acids depicted by the images of clusters of nucleic acids, remove data for a subset of the clusters of nucleic acids from intermediate data; and produce, utilizing the neural network, output patches of classification data for a spatially aligned patch for the subject sensing cycle based on the filtered intermediate data, where N is greater than 1.

* * * * *